(12) United States Patent
Burke et al.

(10) Patent No.: US 12,419,899 B2
(45) Date of Patent: Sep. 23, 2025

(54) ION CHANNEL PROSTHETIC COMPOSITIONS COMPRISING LIPID-COATED CRYSTALS OF AMPHOTERICIN B

(71) Applicants: The Board of Trustees of the University of Illinois, Urbana, IL (US); cystetic Medicines, Inc., San Carlos, CA (US)

(72) Inventors: Martin D. Burke, Champaign, IL (US); Agnieszka Lewandowska, Savoy, IL (US); Corinne Soutar, Urbana, IL (US); Jeffry G. Weers, Half Moon Bay, CA (US); Thomas Tarara, Burlingame, CA (US); Danforth P. Miller, San Carlos, CA (US)

(73) Assignees: The Board of Trustees of the University of Illinois, Urbana, IL (US); cystetic Medicines, Inc., San Carlos, CA (US)

( * ) Notice: Subject to any disclaimer, the term of this patent is extended or adjusted under 35 U.S.C. 154(b) by 0 days.

(21) Appl. No.: 18/891,739

(22) Filed: Sep. 20, 2024

(65) Prior Publication Data
US 2025/0009776 A1 Jan. 9, 2025

Related U.S. Application Data

(63) Continuation of application No. PCT/US2023/015762, filed on Mar. 21, 2023.
(Continued)

(51) Int. Cl.
*A61K 31/7048* (2006.01)
*A61K 9/00* (2006.01)
(Continued)

(52) U.S. Cl.
CPC ........ *A61K 31/7048* (2013.01); *A61K 9/0075* (2013.01); *A61K 9/127* (2013.01);
(Continued)

(58) Field of Classification Search
CPC .. A61K 31/7048; A61K 9/0075; A61K 9/127; A61K 9/1611
See application file for complete search history.

(56) References Cited

U.S. PATENT DOCUMENTS

| | | | |
|---|---|---|---|
| 5,049,389 | A | 9/1991 | Radhakrishnan |
| 5,874,104 | A | 2/1999 | Adler-Moore et al. |

(Continued)

FOREIGN PATENT DOCUMENTS

| | | |
|---|---|---|
| EP | 3439668 A1 | 2/2019 |
| JP | H01160915 A | 6/1989 |

(Continued)

OTHER PUBLICATIONS

Chorghade et al., "Amphotericin B induces epithelial voltage responses in people with cystic fibrosis," Journal of Cystic Fibrosis 20 (2021): 540-550.
(Continued)

*Primary Examiner* — Carlos A Azpuru
(74) *Attorney, Agent, or Firm* — Foley Hoag LLP; Dana M. Gordon; Austin C. Hachey

(57) ABSTRACT

Disclosed are pharmaceutical compositions, comprising: (i) amphotericin B or a pharmaceutically acceptable salt or hydrate thereof; (ii) cholesterol; (iii) phospholipids, comprising hydrogenated soy phosphatidylcholine and distearoylphosphatidylglycerol; and (iv) calcium chloride ($CaCl_2$)). Also disclosed are methods of using the pharmaceutical compositions for treating a disease or disorder (e.g., cystic fibrosis), increasing the pH of airway surface liquid, increasing bicarbonate secretion into airway surface liquid,
(Continued)

and increasing a subject's forced expiratory volume in one second.

26 Claims, 16 Drawing Sheets

Related U.S. Application Data

(60) Provisional application No. 63/321,965, filed on Mar. 21, 2022.

(51) Int. Cl.
*A61K 9/127* (2006.01)
*A61K 9/16* (2006.01)

(52) U.S. Cl.
CPC .......... *A61K 9/1611* (2013.01); *A61K 9/1617* (2013.01); *A61K 9/1682* (2013.01)

(56) References Cited

U.S. PATENT DOCUMENTS

| | | |
|---|---|---|
| 5,880,101 A | 3/1999 | Stankov |
| 5,965,156 A | 10/1999 | Proffitt et al. |
| 6,323,191 B1 | 11/2001 | Harris et al. |
| 6,406,713 B1 | 6/2002 | Janoff et al. |
| 6,770,290 B1 | 8/2004 | Proffitt et al. |
| 7,375,081 B2 | 5/2008 | Ikeda et al. |
| 7,452,524 B2 | 11/2008 | Hofmann et al. |
| 7,544,369 B2 | 6/2009 | Boni et al. |
| 8,003,081 B2 | 8/2011 | Hofmann et al. |
| 8,546,555 B2 | 10/2013 | Gould-Fogerite et al. |
| 8,883,748 B2 | 11/2014 | Verma et al. |
| 9,561,188 B2 | 2/2017 | Odidi et al. |
| 10,159,649 B2 | 12/2018 | Odidi et al. |
| 10,960,018 B2 | 3/2021 | Rowe et al. |
| 11,850,256 B2 | 12/2023 | Burke et al. |
| 12,090,164 B2 | 9/2024 | Burke et al. |
| 2004/0156792 A1 | 8/2004 | Tarara et al. |
| 2004/0176391 A1 | 9/2004 | Weers et al. |
| 2005/0129767 A1 | 6/2005 | Tsai et al. |
| 2006/0159625 A1 | 7/2006 | Tarara et al. |
| 2009/0220599 A1* | 9/2009 | Tsai ............... A61K 9/1075 424/475 |
| 2010/0210575 A1 | 8/2010 | Kwon et al. |
| 2011/0064794 A1* | 3/2011 | Deng ............... A61K 9/1075 977/773 |
| 2012/0015897 A1 | 1/2012 | Verma et al. |
| 2014/0109899 A1 | 4/2014 | Boucher et al. |
| 2014/0194365 A1 | 7/2014 | Feghali-Bostwick et al. |
| 2014/0363506 A1 | 12/2014 | Tarara et al. |
| 2015/0297725 A1* | 10/2015 | Mannino ......... A61K 9/1277 424/450 |
| 2016/0317564 A1 | 11/2016 | Weers |
| 2017/0014342 A1 | 1/2017 | Li et al. |
| 2019/0083517 A1 | 3/2019 | Burke et al. |
| 2020/0352970 A1 | 11/2020 | Burke et al. |
| 2021/0113600 A1 | 4/2021 | Burke et al. |
| 2021/0393661 A1 | 12/2021 | Burke et al. |
| 2024/0277743 A1 | 8/2024 | Burke et al. |
| 2025/0000886 A1 | 1/2025 | Burke et al. |
| 2025/0009775 A1 | 1/2025 | Burke et al. |

FOREIGN PATENT DOCUMENTS

| | | |
|---|---|---|
| JP | 2008/501782 A | 1/2008 |
| JP | 7041961 B2 | 3/2022 |
| WO | WO-2004/060351 A2 | 7/2004 |
| WO | WO-2004/060903 A2 | 7/2004 |
| WO | WO-2005/120497 A2 | 12/2005 |
| WO | WO-2008/127358 A2 | 10/2008 |
| WO | WO-2015/054148 A1 | 4/2015 |
| WO | WO-2016/073462 A1 | 5/2016 |
| WO | WO-2017/177228 A1 | 10/2017 |
| WO | WO-2019/075214 A2 | 4/2019 |
| WO | WO-2023/183297 A1 | 9/2023 |

OTHER PUBLICATIONS

Extended European Search Report for EP Application No. 17779973.1 dated Mar. 9, 2023.
International Search Report and Written Opinion for Application No. PCT/US23/15762 dated Jun. 21, 2023.
Proesmans et al., "Use of Nebulized Amphotericin B in the Treatment of Allergic Bronchopulmonary Aspergillosis in Cystic Fibrosis", International Journal of Pediatrics, vol. 2010, Jan. 2010, pp. 1-9.
Stone et al., "Liposomal Amphotericin B (AmBisome): A Review of the Pharmacokinetics, Pharmacodynamics, Clinical Experience and Future Directions", Drugs, vol. 76, No. 4, Mar. 1, 2016, pp. 485-500.
Weers, "Design of dry powder inhalers to improve patient outcomes: it's not just about the device", Expert Opinion on Drug Delivery 21.3: 365-380 (2024).
Weers, "Suboptimal inspiratory flow rates with passive dry powder inhalers: big issue or overstated problem?", Frontiers in Drug Delivery 2: 855234 (2022).
Adler-Moore et al., "Comparison between liposomal formulations of amphotericin B," Med Mycol, 54: 223-231 (2016).
Anderson et al., "Amphotericin Forms an Extramembranous and Fungicidal Sterol Sponge," Nat Chem Biol, 10(5): 400-406 (2014).
Boggs et al., "Going up in smoke? A review of nAChRs-based treatment strategies for improving cognition in schizophrenia," Curr Pharm Des, 20(31): 5077-5092 (2014).
Casciaro et al., "Role of nebulized amphotericin B in the management of allergic bronchopulmonary aspergillosis in cystic fibrosis: Case report and review of literature," Journal of Chemotherapy, 27(5): 307-311 (2014).
Chuealee, "Amphotericin B incorporated in liquid crystals for fungal infection treatment," A Thesis, Prince of Songkia University, (2009).
Cioffi et al., "Restored Physiology in Protein-Deficient Yeast by a Small Molecule Channel," Journal of The American Chemical Society, 137:10096-10099 (2015).
Cioffi et al., "Supporting Information for: Restored physiology in protein-deficient yeast by a small molecule channel," S1-S14 (2015).
Cioffi, "67—Functional complementation of a deficient protein with a small molecule restores cell physiology," 246th ACS National Meeting and Exposition, Sep. 8-12, 2013, Indianapolis, Indiana (2013).
Cohen, "Amphotericin B Membrane Action: Role for Two Types of Ion Channels in Eliciting Cell Survival and Lethal Effects," J Membrane Biol 238:1-20 (2010).
De Amorim et al., "Characterization of CFTR nonsense mutations using novel CTFR minigenes" (University of Lisbon, Dissertation) (Year: 2013).
De Boeck et al., "Progress in therapies for cystic fibrosis," Lancet Respir Med 4: pp. 662-674 (2016).
Dworakowska et al., "Ion channels-related diseases," Acta BioChimica Polonica, 47(3):685-703 (2000).
Extended European Search Report for EP Application No. 15857452.5 dated May 15, 2018.
Extended European Search Report for EP Application No. 18865483.4 dated May 12, 2021.
Feil et al., "Update on the Pharmacotherapy of Cerebellar Ataxia and Nystagmus," Cerebellum 15:38-42 (2016).
Folkesson et al., "Transepithelial Water Permeability in Microperfused Distal Airways," J Clin Invest, 97(3):664-671 (1996).
Gilead Sciences, "AmBisome (Amphotericin B) Liposome for injection," downloaded from the internet <https://www.gilead.com/~/media/files/pdfs/medicines/other/ambisome_pi.pdf?la=en>. (2018).
Gray et al., "Amphotericin Primarily Kills Yeast by Simply Binding Ergosterol," PNAS, 109(7): 2234-2239 (2012).

(56) References Cited

OTHER PUBLICATIONS

Grillo et al., "574—Restoring growth in protein deficient yeast with a small molecule," 248th ACS National Meeting and Exposition, Aug. 10-14, 2014, San Francisco, CA (2014).
Heijman et al., "Ion channels as part of macromolecular multiprotein complexes," Herzschrittmacherther Elektrophysiol, 29(1):30-35 (2018).
Hennequin et al., "In vitro susceptibilities to amphotericin B, itraconazole, and miconazole of filamentous fungi isolated from patients with cystic fibrosis," Antimicrob Agents Chemother, 41(9):2064-2066 (1997).
Hsu et al., "Characterization of the effects of amphotericin B on ion channels in MDCK cells using the patch-clamp technique," Biochim Biophys Acta 1329:26-38 (1997).
Hubner et al., "Ion Channel Diseases," Human Molecular Genetics, 11(20):2435-2445 (2002).
International Preliminary Report on Patentability for International Application No. PCT/US17/26806 dated Oct. 9, 2018.
International Search Report and Written Opinion for International Application No. PCT/US15/58806 dated Jan. 28, 2016.
International Search Report and Written Opinion for International Application No. PCT/US17/026806 dated Jun. 28, 2017.
International Search Report and Written Opinion for International Application No. PCT/US18/55435 dated Dec. 26, 2018.
Issa et al., "Spinocerebellar ataxia type 13 mutant potassium channel alters neuronal excitability and causes locomotor deficits in zebrafish," The Journal of Neuroscience, 31(18):6831-6841 (2011).
Juang et al., "Disease-targeted sequencing of ion channel genes identifies de novo muttions in patients with non familial brugada syndrome," Scientific Reports, 4(3850) (2014).
Kim, "Channelopathies," Korean J Pediatr, 57(1):1-18 (2014).
Lewis et al., "Comparative analysis of amphotericin B lipid complex and liposomal amphotericin B kinetics of lung accumulation and fungal clearance in a murine model of acute invasive pulmonary aspergillosis," Antimicrob Agents Chemother, 51(4):1253-1258 (2007).
Livraghi et al., "Modelling Dysregulated Na+ Absorption in Airway Epithelial Cells with Mucosal Nystatin Treatment," Am J Respir Cell Mol Biol, 38: 423-434 (2007).
Martínez-Mármol et al., "Targeting potassium channels: New advances in cardiovascular therapy", *Recent Patents on Cardiovascular Drug Discovery* (*Discontinued*) 3(2): 105-118 (2008).
Moss et al, "Long QT syndrome: from channels to cardiac arrhythmias," The Journal of Clinical Investigation, 115(8):2018-2024 (2005).

Perry et al., "Getting to the heart of hERG K+ channel gating", *The Journal of physiology* 593(12): 2575-2585 (2015).
Rabaste et al., "Modifications of pH and K+ gradients in Candida albicans blastospores induced by Amphotericin B. A 31P NMR and K+ atomic absorption study," Biochimica et Biophysica Acta, 1268:50-58 (1995).
Rajakulendran et al., "Episodic ataxia type 1: A neuronal potassium channelopathy," Neurotherapeutics, 4(2):258-266 (2007).
Siempos et al., "Nebulised corticosteroid and amphotericin B: an alternative treatment for ABPA?," European Respiratory Journal, 31(4): 908-909 (2008).
Stanke et al., "Classification of CFTR mutation classes," Lancet Respir Med 4: 1 page (2016).
Strupp et al., "Treatment of episodic ataxia type 2 with the potassium channel blocker 4-aminopyridine," Neurol 62(9):1623-1625 (2004).
Supplementary European Search Report for EP Application No. 17779973.1 dated Nov. 18, 2019.
Thakur, "Correction of electrolyte imbalance prevents cardiac arrhythmia during amphotericin B administration," Natl. Med. J. India, 8(1):13-14 (1995).
Tiddens et al., "Inhaled antibiotics: dry or wet?," European Respiratory Journal, 44: 1308-1318 (2014).
Tong et al., "Astrocyte Kir4. 1 ion channel deficits contribute to neuronal dysfunction in Huntington's disease model mice," Nat Neurosci, 17(5):694-703 (2014).
Tudor et al., "Amphotericin B® treatment causes QT prolongation in lung transplant-patients," Int Care Med Exp 3(1):A213 (2015).
Veit et al., "Some gating potentiators, including VX-770, diminish F508-CFTR functional expression" Sci Transl Med, 6(246): 33 pages (2014).
Wakabayashi et al., "Mucolipidosis type IV: An update," Molecular Genetics and Metabolism, 104:206-213 (2011).
American Chemical Society, Molecule of the Week Archive, "Amphotericin B," Aug. 12, 2019. Available at: https://www.acs.org/molecule-of-the-week/archive/a/amphotericin-b.html.
Chishimba et al., "Efficacy and safety of nebulised amphotericin B (NAB) in severe asthma with fungal sensitisation (SAFS) and allergic bronchopulmonary aspergillosis (ABPA)," Journal of Asthma 52.3 (2015): 289-295.
Dubois et al., "The physiologic effects of inhaled amphotericin B," Chest 108.3 (1995): 750-753.

\* cited by examiner

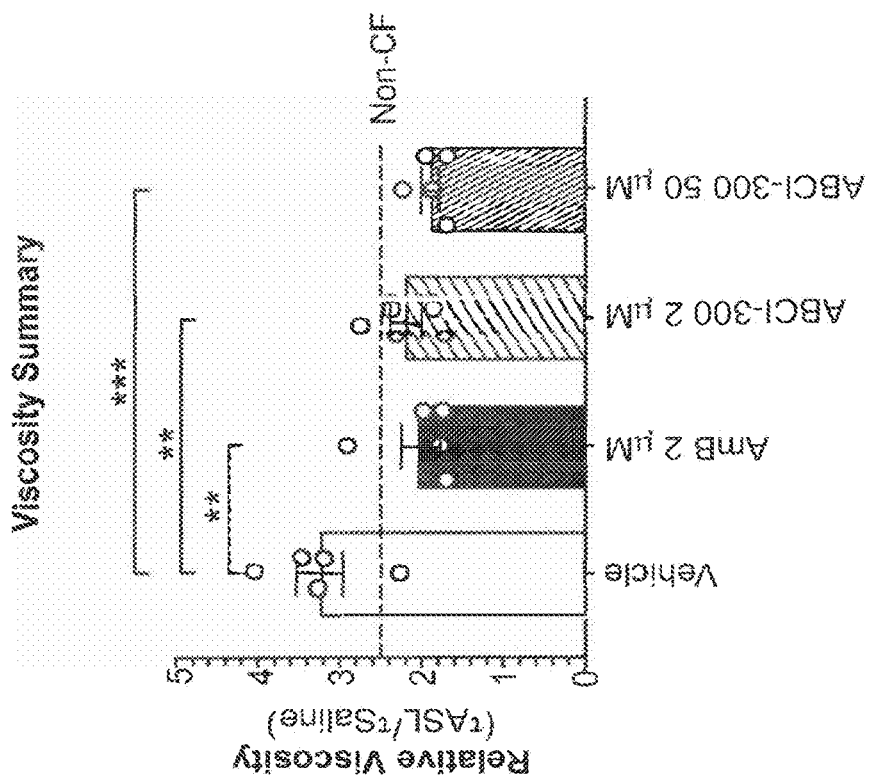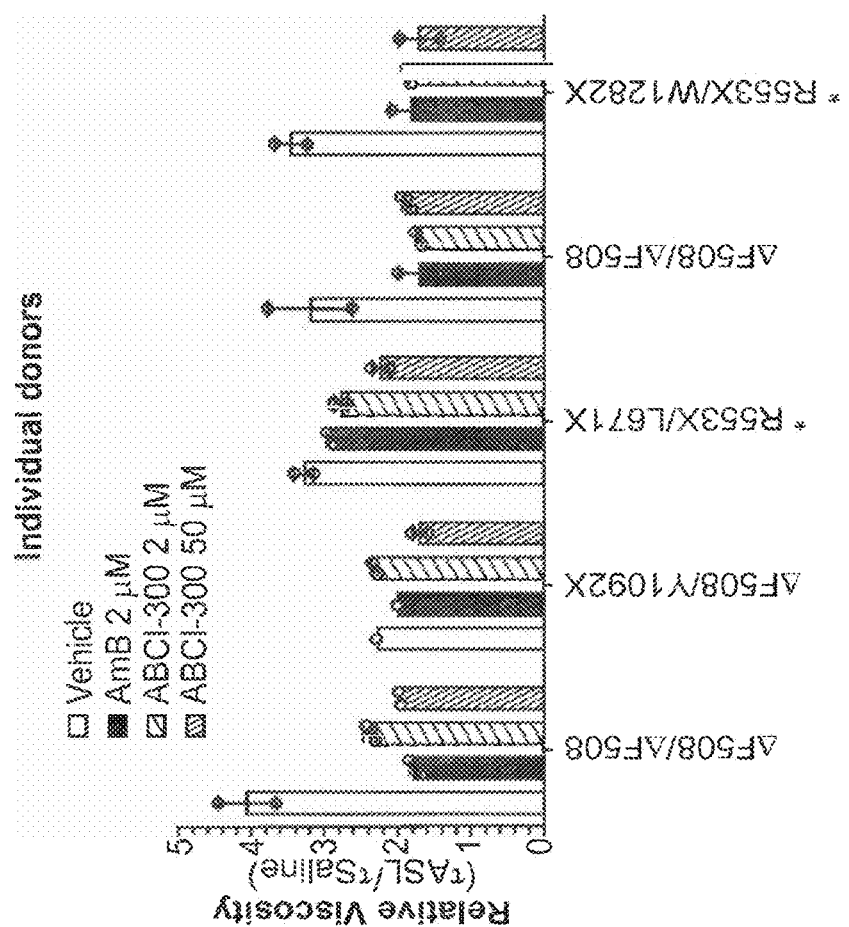
FIG. 10

*nonsense mutations

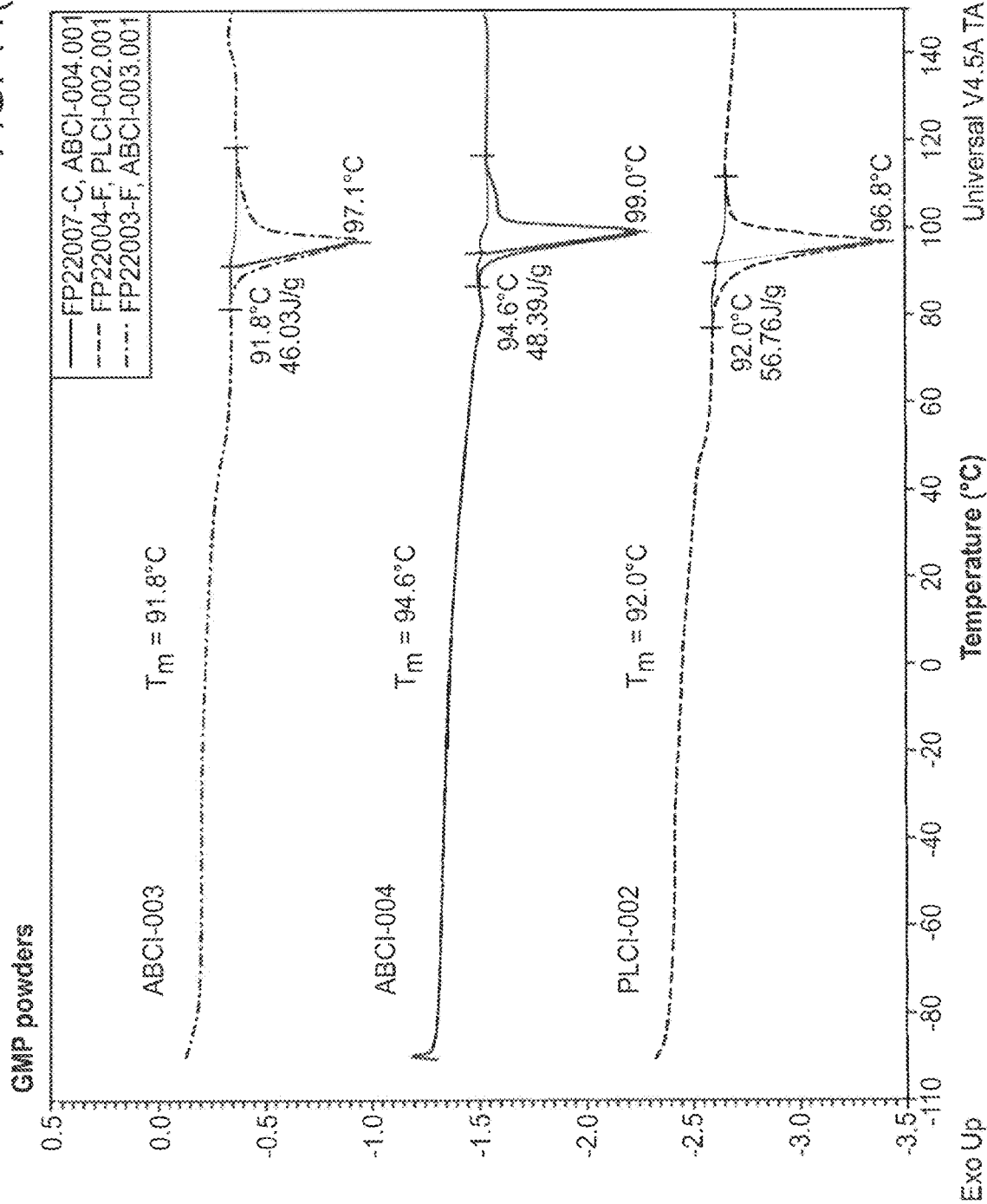

ION CHANNEL PROSTHETIC COMPOSITIONS COMPRISING LIPID-COATED CRYSTALS OF AMPHOTERICIN B

RELATED APPLICATIONS

This application is a Continuation of International Patent Application No. PCT/US23/15762, filed Mar. 21, 2023; which claims the benefit of priority to U.S. Provisional Application No. 63/321,965, filed Mar. 21, 2022.

BACKGROUND

Cystic fibrosis (CF) is a progressive, genetic disease that causes persistent lung infections and limits the ability to breathe over time. The symptoms of CF are caused by a defective protein, known as the cystic fibrosis transmembrane conductance regulator (CFTR) protein. Researchers are investigating potential therapies to restore proper function to the CFTR protein or correct its production process so that a normal protein is made. While current CFTR modulators and correctors improve lung function in approximately 90% of CF patients, there are about 10% of patients with Class I or other mutations for which no effective treatment is available.

Burke and co-workers recently proposed an alternative strategy: the development of small molecule prosthetics for the CFTR protein. To this end, they repurposed the antifungal drug amphotericin B (AmB), which self assembles with cholesterol (Chol) to form monovalent ion channels. Complexes of AmB and Chol were manufactured by flash nanoprecipitation in water from a solution in organic solvents (US 2019/0083517; US 2020/0352970). The resulting nanoparticles were subsequently lyophilized. Burke et al. claimed that ion channels formed from Chol and AmB (Chol/AmB=1.0 to 50.0 mol/mol) were able to restore bicarbonate secretion, increase airway surface liquid (ASL) pH, and improve host defense in CF cell lines (e.g., CuFi-1, CuFi-4 cell lines from the U. Iowa) independent of the genetic mutation. They also demonstrated that the range of concentrations over which AmB is effective in restoring ASL pH was increased if AmB was pre-complexed with cholesterol. That is, neat AmB was only effective at low AmB concentrations, while the AmB:Chol complex maintained activity across a broad range of AmB concentrations.

The benefits of AmB were further established in differentiated primary cultures of human airway epithelia from CF patients with different CFTR mutations, including some that yield no CFTR. The increases in ASL pH were also observed in a CFTR-null pig model.

Finally, intranasal administration of Fungizone®, a commercial parenteral composition of AmB, was able to change the nasal potential difference in people with CF, including those not treatable with current therapies. The improvements in nasal potential difference observed was comparable to that seen with modulators, such as ivacaftor.

The establishment of AmB/Chol ion channels in CF patients requires delivery of these materials to the apical side of airway epithelial cells, i.e., administration via oral inhalation. Similar challenges are observed in subjects with non-cystic fibrosis bronchiectasis (NCFBE) and chronic obstructive pulmonary disease (COPD).

SUMMARY

In certain aspects, provided herein is a pharmaceutical composition, comprising: (i) amphotericin B (AmB) or a pharmaceutically acceptable salt or hydrate thereof; (ii) cholesterol (Chol); (iii) phospholipids (PL), comprising hydrogenated soy phosphatidylcholine (HSPC) and distearoylphosphatidylglycerol (DSPG); and (iv) calcium chloride ($CaCl_2$)).

In further aspects, provided herein is a method of treating a disease or disorder, comprising administering to a subject in need thereof a therapeutically effective amount of the pharmaceutical composition; wherein the administration is pulmonary.

In further aspects, provided herein is a method of increasing the pH of airway surface liquid, comprising administering to a subject in need thereof an effective amount of the pharmaceutical composition, thereby increasing the pH of airway surface liquid in the subject; wherein the administration is pulmonary.

In further aspects, provided herein is a method of increasing bicarbonate secretion into airway surface liquid, comprising administering to a subject in need thereof an effective amount of the pharmaceutical composition, thereby increasing the bicarbonate secretion into airway surface liquid in the subject; wherein the administration is pulmonary.

In further aspects, provided herein is a method of increasing a subject's forced expiratory volume in one second (FEV1), comprising administering to the subject an effective amount of the pharmaceutical composition, thereby increasing the subject's FEV1; wherein the administration is pulmonary.

BRIEF DESCRIPTION OF THE DRAWINGS

FIG. 10 displays a plot showing decreases in ASL viscosity following administration of ABCI-003 to primary cultured airway epithelial cells from individuals with CF, including those with nonsense mutations.

DETAILED DESCRIPTION

Figure 1:
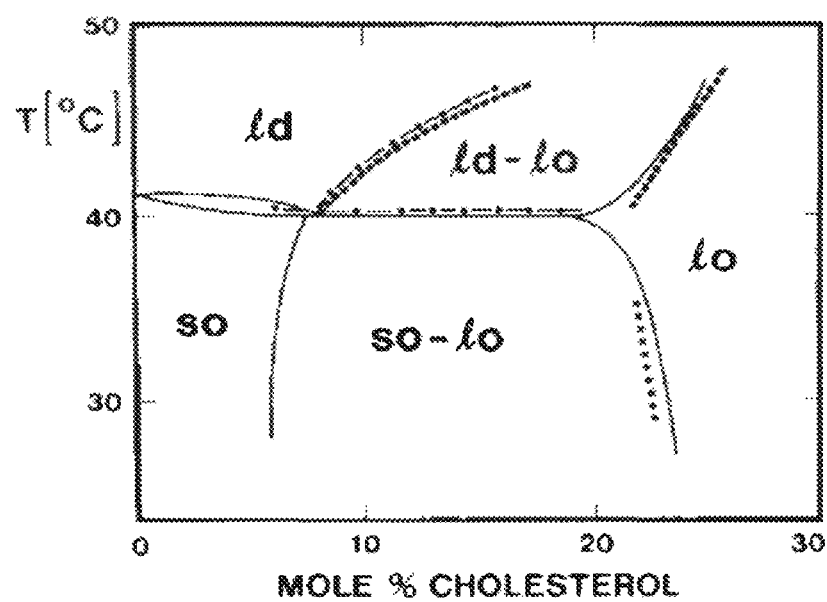
FIG. 1 displays a phase diagram of fully hydrated dipalmitoylphosphatidylcholine-cholesterol mixtures.

It was surprisingly discovered that AmB and Chol need not be complexed to achieve the benefits summarized above. Indeed, the two components can be phase separated into separate domains in core-shell particles.

It was also surprisingly discovered that Chol/AmB ratios much less than 1.0 mol/mol are able to maintain improvements in host defense including improvements in bicarbonate secretion, ASL pH, ASL viscosity, and/or ASL antimicrobial activity.

Compositions

In some aspects, provided is a pharmaceutical composition, comprising:
  (i) amphotericin B (AmB) or a pharmaceutically acceptable salt or hydrate thereof;
  (ii) cholesterol (Chol);
  (iii) phospholipids; and
  (iv) calcium chloride ($CaCl_2$)).

In further aspects, provided is a pharmaceutical composition, comprising:
  (i) amphotericin B (AmB), or a pharmaceutically acceptable salt or hydrate thereof;
  (ii) cholesterol (Chol);
  (iii) phospholipids, comprising hydrogenated soy phosphatidylcholine (HSPC), distearoylphosphatidylcholine (DSPC), or dipalmitoylphosphatidylcholine (DPPC); and distearoylphosphatidylglycerol (DSPG); and
  (iv) calcium chloride ($CaCl_2$)).

In further aspects, provided is a pharmaceutical composition, comprising:
  (i) amphotericin B (AmB), or a pharmaceutically acceptable salt or hydrate thereof;
  (ii) cholesterol (Chol);
  (iii) phospholipids, comprising hydrogenated soy phosphatidylcholine (HSPC) and distearoylphosphatidylglycerol (DSPG); and
  (iv) calcium chloride ($CaCl_2$)).

In certain embodiments, the pharmaceutical composition comprises about 0.5% to about 25% w/w AmB.

In certain embodiments, the pharmaceutical composition comprises about 1% to about 22% w/w AmB.

In certain embodiments, the pharmaceutical composition comprises about 2% to about 16% w/w AmB.

In certain embodiments, the pharmaceutical composition comprises about 14% w/w AmB.

In certain embodiments, the pharmaceutical composition comprises about 0.1% to about 8% w/w Chol.

In certain embodiments, the pharmaceutical composition comprises about 0.5% to about 3% w/w Chol.

In certain embodiments, the pharmaceutical composition comprises about 0.3% to about 6% w/w Chol.

In certain embodiments, the pharmaceutical composition comprises about 0.5% to about 3% w/w Chol.

In certain embodiments, the pharmaceutical composition comprises about 1% to about 10% w/w $CaCl_2$).

In certain embodiments, the pharmaceutical composition comprises about 4% to about 7% w/w $CaCl_2$).

In certain embodiments, the pharmaceutical composition comprises about 60% to about 95% w/w phospholipids.

In certain embodiments, the pharmaceutical composition comprises about 70% to about 90% w/w phospholipids.

In certain embodiments, the pharmaceutical composition comprises about 75% to about 90% w/w phospholipids.

In certain embodiments, the weight ratio of Chol to phospholipids is about 0.001:1 to about 0.1:1.

In certain embodiments, the weight ratio of Chol to phospholipids is about 0.005:1 to about 0.05:1.

In certain embodiments, the weight ratio of soy phosphatidylcholine (HSPC) to distearoylphosphatidylglycerol (DSPG) is about 2:1 to about 19:1.

In certain embodiments, the weight ratio of soy phosphatidylcholine (HSPC) to distearoylphosphatidylglycerol (DSPG) is about 7:1 to about 12:1.

In certain embodiments, the weight ratio of soy phosphatidylcholine (HSPC) to distearoylphosphatidylglycerol (DSPG) is about 1:1 to about 3:1.

In certain embodiments, the molar ratio of Chol to AmB is about 0.05:1 to about 1.2:1.

In certain embodiments, the molar ratio of Chol to AmB is about 0.4:1 to about 1.2:1.

In certain embodiments, the molar ratio of Chol to AmB is about 0.05:1 to about 0.4:1.

In certain embodiments, the molar ratio of Chol to AmB is about 0.4:1.

In certain embodiments, the molar ratio of phospholipids to $CaCl_2$) is about 4:1 to about 2:1.

In certain embodiments, the molar ratio of phospholipids to $CaCl_2$) is about 2:1.

In certain embodiments, the AmB has a crystallinity greater than about 75%.

In certain embodiments, the AmB has a crystallinity greater than about 85%.

In certain embodiments, the AmB has a crystallinity greater than about 95%.

In certain embodiments, the pharmaceutical composition comprising, consisting essentially of, or consisting of:
  (i) about 14.0% w/w amphotericin B (AmB);
  (ii) about 2.3% w/w cholesterol (Chol);
  (iii-a) about 70.3% w/w hydrogenated soy phosphatidylcholine (HSPC);
  (iii-b) about 7.8% w/w distearoylphosphatidylglycerol (DSPG); and
  (iv) about 5.52% w/w calcium chloride ($CaCl_2$)).

In certain embodiments, the pharmaceutical composition comprising, consisting essentially of, or consisting of:
  (i) about 14.0% w/w amphotericin B (AmB);
  (ii) about 6.81% w/w cholesterol (Chol);
  (iii-a) about 51.2% w/w hydrogenated soy phosphatidylcholine (HSPC);
  (iii-b) about 22.8% w/w distearoylphosphatidylglycerol (DSPG); and
  (iv) about 5.2% w/w calcium chloride ($CaCl_2$)).

In certain embodiments, the pharmaceutical composition comprising, consisting essentially of, or consisting of:
  (i) about 3.4% w/w amphotericin B (AmB);
  (ii) about 0.57% w/w cholesterol (Chol);
  (iii-a) about 80.72% w/w hydrogenated soy phosphatidylcholine (HSPC);
  (iii-b) about 8.97% w/w distearoylphosphatidylglycerol (DSPG); and
  (iv) about 6.34% w/w calcium chloride ($CaCl_2$)).

In certain embodiments, the pharmaceutical composition comprising:
  (i) a Chol/AmB ratio of about 0.4 to 1.2 mol/mol;
  (ii) a Chol/PL ratio of less than about 0.05 w/w;
  (iii) a HSPC/DSPG ratio of about 2.3 to about 9.0 w/w; and
  (iv) a PL/$Ca^{2+}$ ratio of about 2:1 mol/mol.

In certain embodiments, the AmB and Chol are not complexed; and the AmB is not encapsulated in liposomes.

In certain embodiments, the AmB is coated with a porous shell of phospholipids and Chol.

In certain embodiments, the pharmaceutical composition is formulated as a dry powder.

In certain embodiments, the tapped density of the powder particles is about 0.03 to about 0.4 g/mL.

In certain embodiments, the tapped density of the powder particles is about 0.06 to about 0.2 g/mL.

In certain embodiments, the Carr's index of the powder particles is about 20 to about 32.

In certain embodiments, the main transition temperature ($T_m$) of the shell is at least 70° C., at least 80° C., or at least 90° C. In certain embodiments, the main transition temperature ($T_m$) of the shell is about 50° C. to about 100° C., about 70° C. to about 100° C., about 80° C. to about 100° C., or about 85° C. to about 95° C.

In certain embodiments, the water content of the powder is about 1.5 to about 6% w/w.

In certain embodiments, the composition is formulated for pulmonary administration or airway administration.

In certain embodiments, the composition is formulated for aerosol administration.

In certain embodiments, the composition is formulated for aerosol administration as a dry powder.

In certain embodiments, a dry powder composition of engineered particles is provided that includes a plurality of AmB drug particles coated with a porous shell of phospholipids (PL) and Chol, wherein the crystallinity of AmB is at least 75%, at least 80%, at least 85%, at least 90% or at least 95%.

In certain embodiments, the mass median diameter, $X_{50}$, of the powder particles is about 0.5 μm to about 5.0 μm, about 1.0 μm to about 4.0 μm, or about 1.5 μm to about 3.5 μm.

In certain embodiments, the powder particles have an $X_{90}$ of about 1.5 μm to about 10.0 μm, such as about 2.0 μm to about 8.0 μm.

In certain embodiments, the mass median aerodynamic diameter (MMAD) of the powder particles is about 1.5 μm to about 4.0 μm.

In certain embodiments, the mass median aerodynamic diameter (MMAD) of the powder particles is about 2.0 μm to about 3.5 μm.

In certain embodiments, a carrier-free dry powder composition of AmB, Chol, and PL is provided, wherein AmB is not encapsulated in the lipids, and the AmB and lipids are phase separated in their own domains.

In certain embodiments, a dry powder composition of engineered particles is provided that includes a plurality of AmB drug particles coated with a porous shell of PL and Chol, wherein the Chol/AmB ratio is about 0.05 to about 1.2 mol/mol, such as about 0.2 to about 0.6 mol/mol.

In certain embodiments, a dry powder composition of engineered particles is provided that includes a plurality of AmB drug particles coated with a porous shell of PL and Chol, wherein the Chol/PL is less than 0.10 w/w, or less than 0.05 w/w.

In certain embodiments, a dry powder composition of engineered particles is provided that includes a plurality of AmB drug particles coated with a porous shell comprising PL and Chol. In some embodiments, the PL comprises hydrogenated soy phosphatidylcholine (HSPC), distearoylphosphatidylcholine (DSPC), dipalmitoylphosphatidylcholine (DPPC), distearoylphosphatidylglycerol (DSPG), or a combination thereof.

In certain embodiments, a dry powder composition of engineered particles is provided that includes a plurality of AmB drug particles coated with a porous shell of PL and Chol, wherein the PL comprises a mixture of (1) HSPC or DSPC, and (2) DSPG in a w/w ratio of about 2.3 w/w (i.e., 7/3 w/w) and about 19.0 w/w (i.e., 95/5 w/w), such as about 8 w/w to about 18 w/w.

In certain embodiments, a dry powder composition of engineered particles is provided that includes a plurality of AmB drug particles coated with a porous shell of PL, Chol, and calcium chloride ($CaCl_2$)), wherein the PL/Ca ratio is about 2.0 mol/mol to about 4.0 mol/mol, about 2.0 mol/mol to about 3.0 mol/mol, or about 2.0 mol/mol. The PL/Ca ratio should not decrease below about 2.0 mol/mol.

In certain embodiments, a dry powder composition of engineered particles is provided that includes a plurality of AmB drug particles coated with a porous shell of PL, Chol, and calcium chloride ($CaCl_2$)), wherein the percentage of AmB in the composition is less than 60% w/w, such as less than 30% or less than 20% w/w. In some embodiments, the drug loading is about 0.5% to about 25% w/w, and the nominal Chol/AmB ratio is about 0.05 to about 1.2 mol/mol.

In certain embodiments, a dry powder composition of engineered particles is provided (ABCI-003) that includes spray-dried core-shell particles of fine crystalline AmB particles (about 14.0% w/w) coated with a porous shell of PL and Chol, wherein the Chol/AmB ratio is about 0.4 mol/mol, the Chol/PL ratio is about 0.03 w/w, the PL/Ca ratio is about 2 mol/mol, and the ratio of PC/PG in the PL is about 9.0 w/w.

In certain embodiments, a dry powder composition of engineered particles is provided (ABCI-004) that includes spray-dried core-shell particles of fine crystalline AmB particles (about 3.4% w/w) coated with a porous shell of PL and Chol, where the Chol/AmB ratio is about 0.4 mol/mol, the Chol/PL ratio is about 0.006 w/w, the PL/Ca ratio is about 2 mol/mol, and the ratio of PC/PG in the PL is about 9.0 w/w.

In certain embodiments, a dry powder composition of engineered particles is provided (FIG. 2) that includes spray-dried core-shell particles of fine crystalline AmB particles (14.0% w/w) coated with a porous shell of PL and Chol, where the Chol/AmB ratio is about 0.4 to about 1.2 mol/mol, the Chol/PL ratio is less than 0.05 w/w, the PL/Ca ratio is about 2 mol/mol, and the ratio of PC/PG in the PL is between about 2.3 and about 9.0 w/w.

In certain embodiments, the maximum Chol/AmB ratio is about 1.2 mol/mol, but this high ratio may be acceptable only for lower drug loadings (e.g., no more than 10.0% w/w) where the lipids are maintained in a highly ordered so phase. Decreases in the Chol/AmB to 0.4 mol/mol may allow higher drug loadings (e.g., no more than 22% w/w) within the so phase.

Figure 2:
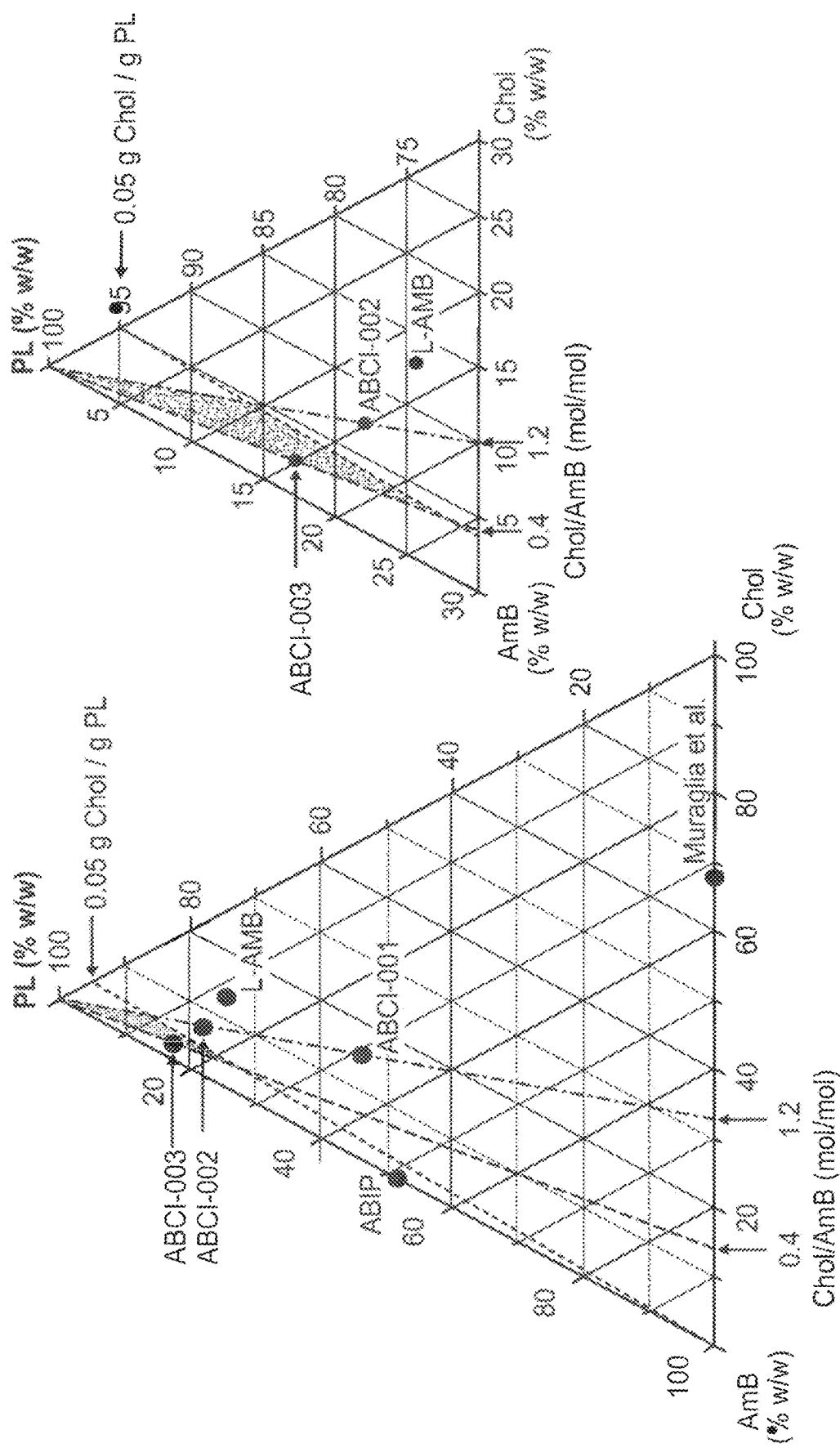
FIG. 2 displays a ternary phase diagram showing various AmB/lipid compositions. The shaded triangle represents optimized lipid-coated crystal compositions of amphotericin B.

In some embodiments, the compositions described herein occupy the shaded triangle in FIG. 2. Two sides of the triangle represent lines for nominal Chol/AmB ratios of 0.4 and 1.2 mol/mol, while the third side represents a Chol/PL ratio (Chol/PL=0.05 w/w) that may result in elimination of a Chol-rich phase in DSC thermograms (Example 4).

In certain embodiments, the compositions described herein include an HSPC/DSPG ratio of about 2.3 to about 9.0 w/w, and a PL/$Ca^{2+}$ ratio of about 2.0 mol/mol.

In certain embodiments, selection of the compositions described herein is driven by maintenance of the lipids in a single phase (i.e., the gel phase (so) with a $T_m$ that is more than 50° C. above an accelerated storage temperature of 40° C. (Example 4)). In some embodiments, selection of the compositions described herein is driven by maximal increases in ASL pH that are maintained across a wide range of AmB concentrations (Example 11). In certain embodiments, selection of the compositions described herein is driven by decreased hygroscopicity relative to compositions with HSPC/DSPG <9.0 (Example 5). In some embodiments, selection of the compositions described herein is driven by increased manufacturing yield (Example 9). In certain embodiments, selection of the compositions described herein is driven by improved powder flowability (Example 9). In some embodiments, selection of the compositions described herein is driven by improved aerosol performance relative to powders containing the lo phase (Example 9). In certain embodiments, selection of the compositions described herein is driven by excellent performance in restoring host defense in cell-based assays, both in CuFi-1 cells and in primary cultures from CF patients, even those with nonsense mutations (Example 10). In some embodiments, selection of the compositions described herein is driven by no red blood cell hemolysis even at low Chol/AmB molar ratios (Example 15).

In certain embodiments, a dry powder composition of engineered particles is provided that includes a plurality of AmB drug particles coated with a porous shell of PL, Chol, and calcium chloride ($CaCl_2$)), wherein the nominal dose is about 0.01 mg to about 50 mg, about 0.1 mg to about 10.0 mg, about 0.5 mg, about 1.0 mg, about 2.0 mg, about 4.0 mg, or about 6.0 mg.

In certain embodiments, a dry powder composition of engineered particles is provided that includes a plurality of AmB drug particles coated with a porous shell of PL, Chol, and calcium chloride ($CaCl_2$)), wherein the mass median diameter ($X_{50}$) of the particles is about 1.0 to about 5.0 µm, such as about 1.5 to about 4.0 µm.

In certain embodiments, a dry powder composition of engineered particles is provided that includes a plurality of AmB drug particles coated with a porous shell of PL, Chol, and calcium chloride ($CaCl_2$)), wherein the $X_{90}$ of the particles is about 3 µm to about 10 µm, such as about 3.5 µm to about 7 µm.

In certain embodiments, a dry powder composition of engineered particles is provided that includes a plurality of AmB drug particles coated with a porous shell of PL, Chol, and calcium chloride ($CaCl_2$)), wherein the tapped density of the particles is about 0.03 to about 0.40 g/mL, such as about 0.06 to about 0.20 g/mL.

In certain embodiments, a dry powder composition of engineered particles is provided that includes a plurality of AmB drug particles coated with a porous shell of PL, Chol, and calcium chloride ($CaCl_2$)), wherein the water content in the powder is about 1.0% to about 10.0%, preferably about 2.0% to about 5.0%.

In certain embodiments, a dry powder composition of engineered particles is provided that includes a plurality of AmB drug particles coated with a porous shell of PL, Chol, and calcium chloride ($CaCl_2$)), wherein the mass median aerodynamic diameter (MMAD) is about 1.0 µm to about 6.0 µm, such as about 2.0 µm to about 4.0 µm, when administered from a portable dry powder inhaler.

In certain embodiments, a dry powder composition of engineered particles is provided that includes a plurality of AmB drug particles coated with a porous shell of PL, Chol, and calcium chloride ($CaCl_2$)), wherein the fine particle fraction less than 5 µm expressed as a percentage of the nominal dose is at least 30% w/w, at least 50%, or at least 60% w/w, when administered with a portable dry powder inhaler.

In certain embodiments, a dry powder composition of engineered particles is provided that includes a plurality of crystalline AmB drug particles coated with a porous shell of PL, Chol, and calcium chloride ($CaCl_2$)), wherein the powder is produced by spray drying a liquid feedstock comprising fine AmB crystals suspended in an oil-in-water emulsion stabilized by a monolayer of the mixture of lipids described herein.

In certain embodiments, a dry powder composition of engineered particles is provided that includes a plurality of crystalline AmB drug particles coated with a porous shell of PL, Chol, and calcium chloride ($CaCl_2$)), wherein the lipids have a main transition temperature ($T_m$) of at least 80° C., such as at least 90° C.

In certain embodiments, a dry powder composition of engineered particles is provided that includes a plurality of crystalline AmB drug particles coated with a porous shell of PL, Chol, and calcium chloride ($CaCl_2$)), wherein the powder is produced by spray drying a liquid feedstock at an outlet temperature that is less than the lowest $T_m$ of the lipids. In some embodiments, the outlet temperature is at least 50° C., at least 60° C., or at least 70° C.

In certain embodiments, a dry powder composition of engineered particles is provided that includes a plurality of crystalline AmB drug particles coated with a porous shell of PL, Chol, and calcium chloride ($CaCl_2$)), wherein the powder is produced by spray drying a liquid feedstock at an outlet temperature that is less than the lowest $T_m$ of the lipids. In some embodiments, the outlet temperature is at least 60° C., or at least 70° C.

In certain embodiments, a dry powder composition of engineered particles is provided that includes a plurality of crystalline AmB drug particles coated with a porous shell of PL, Chol, and calcium chloride ($CaCl_2$)), wherein the powder is produced by spray drying a liquid feedstock at a total gas flow on a PSD-1 scale spray dryer of about 70 to about 100 scfm.

In certain embodiments, the dry powder composition of engineered particles comprising AmB drug particles coated with a porous shell of PL, Chol, and calcium chloride ($CaCl_2$)), is filled with a drum filler.

In certain embodiments, the powder fill mass is about 1.0 mg to about 40 mg in a size 3 or size 2 capsule, such as about 3 mg to about 20 mg, or about 10 mg to about 15 mg.

In certain embodiments, the powder fill mass has good precision (e.g., RSD <3%) and accuracy for the target fill mass.

Methods

In certain aspects, provided is a method of treating a disease or disorder, comprising administering to a subject in need thereof a therapeutically effective amount of a pharmaceutical composition according to any one of the embodiments described herein; wherein the administration is pulmonary. In certain embodiments, the disease or disorder comprises cystic fibrosis, non-cystic fibrosis bronchiectasis (NCFBE), or chronic obstructive pulmonary disease (COPD). In certain embodiments, the disease or disorder is cystic fibrosis.

Provided is a method for restoring the host defense characteristics of ASL (e.g., increases in bicarbonate secretion, pH, antimicrobial activity, and/or reductions in viscosity), comprising administering to a subject in need thereof an effective amount of a pharmaceutical composition according to any one of the embodiments described herein, thereby improving lung function and quality of life.

Also provided is a method of increasing the pH of airway surface liquid, comprising administering to a subject in need thereof an effective amount of a pharmaceutical composition according to any one of the embodiments described herein, thereby increasing the pH of airway surface liquid in the subject; wherein the administration is pulmonary.

Also provided is a method of increasing bicarbonate secretion into airway surface liquid, comprising administering to a subject in need thereof an effective amount of a pharmaceutical composition according to any one of the embodiments described herein, thereby increasing bicarbonate secretion into airway surface liquid in the subject; wherein the administration is pulmonary.

Also provided is a method of increasing forced expiratory volume in one second (FEV1), comprising administering to a subject in need thereof an effective amount of a pharmaceutical composition according to any one of the embodiments described herein, thereby increasing the subject's FEV1; wherein the administration is pulmonary.

In some embodiments, a subject's FEV1 is said to be increased when it is measurably greater than the same subject's FEV1 measured prior to or distant in time from treatment according to a method of the present disclosure.

In certain embodiments, the subject's FEV1 is increased by about 3% to about 20%, about 5% to about 15%, or about 6% to about 10%.

In certain embodiments, the subject has CF.

In certain embodiments, the pharmaceutical composition is administered to an airway of the subject.

In certain embodiments, the pharmaceutical composition is administered to the bronchial airways of the subject.

In certain embodiments, the pharmaceutical composition is administered as an aerosol.

In certain embodiments, the pharmaceutical composition is administered as a dry powder aerosol.

In certain embodiments, the subject is a human.

In certain embodiments, the subject is an adult human.

In certain embodiments, the subject is a human less than 12 years old.

In certain embodiments, the subject is a human at least 12 years old.

In certain embodiments, the subject is a human at least 4 years old.

In certain embodiments, the CF is refractory to treatment with ivacaftor; or the combination of elexacaftor, tezacaftor, and ivacaftor.

In certain embodiments, a subject with CF has Class 1 or other mutations that are not treated effectively with current modulators, including combination therapies. This includes nonsense mutations or other mutations where no functional CFTR protein is produced.

In certain embodiments, the subject has two mutations in the CF transmembrane conductance regulator (CFTR) anion channel; and the two mutations are each independently selected from the mutations listed in Table 1.

TABLE 1

Exemplary CTFR Mutations

| | | | |
|---|---|---|---|
| R75X | 663delT | 1525 − 1G−>A | 1924del7 |
| CFTRdele1 | G178R | 1525 − 2A−>G | 2055del9−>A |
| M1V | 675del4 | S466X | 2105-2117del13insAGAAA |
| Q2X | E193X | L467P | 2118del4 |
| S4X | 711 + 1G−>T | 1548delG | 2143delT |
| 182delT | 711 + 3A−>G | S489X | G673X |
| CFTRdele2 | 711 + 5G−>A | S492F | 2183AA−>G or 2183delAA−>G |
| CFTRdele2-4 | 712 − 1G−>T | 1609delCA | 2184insA |
| 185 + 1G−>T | H199Y | Q493X | 2184delA |
| CFTRdele2, 3 | P205S | W496X | 2185insC |
| W19X | L206W | I507del | Q685X |
| R75X | W216X | F508del | R709X |
| Q39X | Q220X | 1677delTA | K710X |
| A46D | L227R | V520F | Q715X |
| 296 + 1G−>A | 849delG | C524X | 2307insA |
| 296 + 1G−>T | 852del22 | Q525X | L732X |
| CFTRdele3-10, 14b-16 | CFTRdup6b-10 | CFTRdele11 | 2347delG |
| 297 − 1G−>A | 935delA | 1717 − 1G−>A | 2372del8 |
| E56K | Y275X | 1717 − 8G−>A | R764X |
| W57X | C276X | G542X | R785X |
| 306insA | 991del5 | S549R | R792X |
| 306delTAGA | 1078delT | S549N | 2556insAT |
| E60X | 1119delA | G550X | 2585delT |
| P67L | G330X | 1782delA | 2594delGT |
| R75X | R334W | G551S | E822X |
| 365-366insT | 1138insG | G551D | 2622 + 1G−>A |

TABLE 1-continued

Exemplary CTFR Mutations

| | | | |
|---|---|---|---|
| G85E | I336K | Q552X | E831X |
| 394delTT | T338I | R553X | W846X |
| L88X | S341P | A559T | Y849X |
| CFTRdele4-7 | 1154insTC | 1811 + 1634A->G or 1811 + 1.6kbA->G | R851X |
| CFTRdele4-11 | 1161delC | 1811 + 1G->C | 2711delT |
| CFTR50kbdel | R347H | R560K | 2721del11 |
| 405 + 1G->A | R347P | R560T | 2732insA |
| 405 + 3A->C | R352Q | 1811 + 1G->A | CFTRdele14b-17b |
| 406 – 1G->A | 1213delT | 1811 + 1643G->T | W882X |
| E92K | 1248 + 1G->A | 1812 – 1G->A | 2789 + 5G->A |
| E92X | 1249 – 1G->A | R560S | 2790 – 1G->C |
| Q98X | 1259insA | A561E | Q890X |
| 442delA | 1288insTA | V562I | S912X |
| 444delA | W401X | 1824delA | 2869insG |
| 457TAT->G | 1341 + 1G->A | 1833delT | Y913X |
| D110H | 1343delG | Y569D | 2896insAG |
| R117C | Q414X | E585X | L927P |
| R117H;5T | D443Y | 1898 + 1G->A | 2942insT |
| 541delC | 1461ins4 | 1898 + 1G->C | 2957delT |
| 574delA | 1471delA | CFTRdele13, 14a | S945L |
| 602del14 | A455E | 1898 + 3A->G | 2991del32 |
| 621 + 1G->T | 1497delGG | 1898 + 5G->T | 3007delG |
| 3120G->A | 3132delTG | H1054D | 3028delA |
| CFTRdele17a, 17b | 3171delC | G1061R | G970R |
| CFTRdele17a-18 | 3171insC | L1065P | CFTRdele16-17b |
| 3120 + 1G->A | Q1042X | R1066C | L1077P |
| 3121 – 1G->A | 3271delGG | R1066H | W1089X |
| 3121 – 2A->G | 3272 – 26A->G | 3600G->A | Y1092X |
| 3121-977_3499 + 248del2515 | 3600G->A | CFTRdele19 | W1098X |
| 3349insT | CFTRdele19 | CFTRdele19-21 | M1101K |
| 3659delC | CFTRdele19-21 | 3600 + 2insT | R1102X |
| 3667ins4 | 3600 + 2insT | 3600 + 5G->A | E1104X |
| S1196X | 3600 + 5G->A | R1158X | 3500 – 2A->G |
| 3737delA | R1158X | R1162X | W1145X |
| W1204X | R1162X | W1282X | CFTRdele22-24 |
| 3791delC | 3849G->A | 4005 + 1G->A | CFTRdele22, 23 |
| Y122X | 3849 + 4A->G | CFTRdele21 | Q1330X |
| 3821delT | 3849 + 40A->G | 4005 + 2T->C | G1349D |
| I1234V | 3849 + 10kbC->T | 4010del4 | 4209TGTT->AA |
| 4326delTC | 3850 – 1G->A | 4015delA | 4218insT |
| Q1411X | 3850 – 3T->G | 4016insT | E1371X |
| Q1412X | G1244E | 4022insT | 4259del15 |
| 4374 + 1G->T | 3876delA | 4021dupT | Q1382X |
| 4374 + 1G->A | 3878delG | 4040delA | 4279insA |
| 4382delA | S1251N | N1303K | S1255P |
| 4428insGA | L1254X | Q1313X | S1255X |
| 3905insT | D259G | | |

In certain embodiments, the two mutations are each independently selected from 2184delA, F508del, V520F, 1717-1G->A, E60X, G551D, R553X, and D259G.

In certain embodiments, the two mutations are a pair of CFTR mutations selected from F508del/F508del, G551D/F508del, R553X/E60X, F508del/1717-1G->A, F508del/2184delA, and D259G/V520F.

In certain embodiments, the two mutations are a pair of CFTR mutations selected from F508del/F508del, R553X/E60X, F508del/1717-1G->A, F508del/2184delA, and D259G/V520F.

In certain embodiments, the nominal dose or metered dose of the pharmaceutical composition is 0.01 mg to 10 mg.

In certain embodiments, the nominal dose or metered dose of the pharmaceutical composition is about 0.1 mg, about 0.5 mg, about 1.0 mg, about 2.0 mg, or about 4.0 mg.

In certain embodiments, the composition is administered at least once daily, at least twice daily, or at least three times daily.

In certain embodiments, the composition is administered once daily.

In certain embodiments, the composition is administered at least once weekly, at least twice weekly, or at least three times weekly.

In certain embodiments, the administering comprises initially delivering a loading dose of the pharmaceutical composition; and subsequently delivering a maintenance dose of the pharmaceutical composition; wherein the mass ratio of the loading dose to the maintenance dose is about 2:1 to about 5:1. In certain embodiments, the mass ratio of the loading dose to the maintenance dose is about 2.5:1 to about 3:1. In certain embodiments, the loading dose is about 1.0 mg to about 20 mg, about 3 mg to about 15 mg, or about 6 mg to about 10 mg. In certain embodiments, the maintenance dose is about 0.1 mg to about 5 mg, about 0.5 mg to about 5 mg, about 1 mg to about 4 mg, or about 2 mg. In certain embodiments, the loading dose is about 1.5 mg and the maintenance dose is about 0.5 mg. In certain embodiments, the loading dose is about 6 mg and the maintenance dose is about 2 mg. In certain embodiments, the loading dose is about 10 mg and the maintenance dose is about 4 mg.

All of the masses described above for the loading dose and the maintenance dose refer to the mass of the nominal dose or the metered dose (i.e., not the emitted dose) of the pharmaceutical composition.

In certain embodiments, a method of treating a subject with CF, NCFBE, or COPD, comprising administering to a subject in need thereof an effective amount of a lipid-coated crystal composition comprising AmB and Chol as provided in this disclosure, wherein the lipid-coated crystal composition is administered to the subject via oral inhalation to the bronchial airways in the lungs.

In certain embodiments, a method of treating a subject with CF, NCFBE or COPD, comprising administering to a subject in need thereof an effective amount of a lipid-coated crystal composition comprising AmB and Chol as provided in this disclosure, wherein the composition provides an increase in ASL pH of about 0.2 to about 1.0 pH units.

In certain embodiments, a method of treating a subject with CF, NCFBE, or COPD, comprising administering to a subject in need thereof an effective amount of a lipid-coated crystal composition comprising AmB and Chol as provided in this disclosure, wherein the composition provides clinically significant improvements in lung function ($FEV_1$) relative to placebo.

In some embodiments, provided herein is a method of decreasing airway surface liquid viscosity in individuals with CF, NCFBE, or COPD, comprising administering to a subject in need thereof an effective amount of a pharmaceutical composition according to any one of the embodiments described herein, thereby increasing hydration and height of airway surface liquid, while decreasing the viscosity of airway surface liquid in the subject; wherein the administration is pulmonary.

In some embodiments, provided herein is a method of increasing the antibacterial activity of airway surface liquid in individuals with CF, NCFBE, or COPD, comprising administering to a subject in need thereof an effective amount of a pharmaceutical composition according to any one of the embodiments described herein, thereby increasing the antibacterial activity of airway surface liquid in the subject; wherein the administration is pulmonary.

In some embodiments, provided herein is a method of increasing mucociliary clearance in individuals with CF, NCFBE, or COPD, comprising administering to a subject in need thereof an effective amount of a pharmaceutical composition according to any one of the embodiments described herein, thereby increasing mucociliary clearance in the subject; wherein the administration is pulmonary.

In some embodiments, provided herein is a method of increasing lung function in individuals with CF, NCFBE, or COPD, comprising administering to a subject in need thereof an effective amount of a pharmaceutical composition according to any one of the embodiments described herein, thereby increasing lung function in the subject; wherein the administration is pulmonary.

In some embodiments provided herein is a method of increasing health related quality of life (HRQoL) in individuals with CF, NCFBE, or COPD, comprising administering to a subject in need thereof an effective amount of a pharmaceutical composition according to any one of the embodiments described herein, thereby increasing HRQoL in the subject; wherein the administration is pulmonary.

In certain embodiments, provided herein is a method of treating a subject with CF, NCFBE, or COPD, comprising administering to a subject in need thereof an effective amount of a lipid-coated crystal composition comprising AmB and Chol as provided in this disclosure, wherein the lipid-coated crystal composition provides a clinically significant increase in health-related quality of life relative to placebo.

In certain embodiments, provided herein is a method of improving lung function, comprising administering to a subject in need thereof an effective amount of the pharmaceutical composition of the present disclosure, thereby improving lung function in the subject; wherein the administration is pulmonary.

In certain embodiments, the subject has CF, NCFBE, or COPD.

In certain embodiments, the subject has CF.

In certain embodiments, the pharmaceutical composition is a dry powder.

In certain embodiments, the dry powder is administered with a portable dry powder inhaler.

In certain embodiments, the dry powder inhaler utilizes the subjects inspiratory flow to fluidize and disperse the powder (i.e., the device is a passive dry powder inhaler)

In certain embodiments, the dry powder inhaler has a medium to high resistance to airflow are preferred (i.e., about 0.10 to 0.30 cm $H_2O^{0.5}$ $L^{-1}$ min)

In certain embodiments, the portable dry powder inhaler includes capsule-based unit dose DPIs, single-use disposable DPIs, or blister-based multi-dose dry powder inhalers.

Over 1900 different CFTR mutations are found in CF patients, hundreds of which are confirmed to be disease causing through at least five different mechanisms of functional loss. There have been important recent advances in the development of genotype-specific small molecule drugs that bind to certain mutant forms of CFTR and thereby increase its activity. However, about 10% of CF patients have CFTR genotypes that do not respond to current small molecule treatments. These include major truncations that yield a complete lack of functional CFTR protein and very rare mutations for which the mechanistic underpinnings of functional deficiency are unknown.

In some embodiments, any of the methods disclosed herein treat a mutation class of CF selected from the group consisting of I, II, III, IV, V, VI, U, and combinations thereof. In some embodiments, the mutation class is selected from the group consisting of I/I, II/II, II/U, and U/III.

Without intending to be bound by theory, the compositions described herein do not modulate, correct, or alter the activity of CFTR channels. The molecular prosthetics comprising lipid-coated crystals of AmB are believed to create new ion channels with activity independent of CFTR and a subject's specific genetic mutation.

In some embodiments, any of the methods disclosed herein are genotype-independent treatments.

As used herein, the phrases "genotype-independent" or "genotype-agnostic" refer to any treatment that is independent of the exact nature of the genetic mutation underlying the reduced CFTR expression or reduced CFTR function in CF.

In certain embodiments, the methods described herein are useful in the treatment of various CF genotypes that are typically non-responsive or minimally-responsive to treatment with conventional CF therapeutics. For example, the V520F allele in patients having the D259G/V520F pair of CTFR mutations is refractory to treatment with ivacaftor; or the combination of elexacaftor, tezacaftor, and ivacaftor.

Accordingly, in certain embodiments, the methods of treating CF described herein are agnostic to CF genotype.

In certain embodiments, any of the methods disclosed herein treat refractory or resistant CF. In certain embodiments, the CF is refractory or resistant to one or more CF treatments.

The pH of airway surface liquid (ASL) in a subject can be measured using any technique known to those of skill in the art. For example, airway pH can be measured by placing a planar pH-sensitive probe on the tracheal surface. Pezzulo A A et al. (2012) *Nature* 487:109-113.

The pH of ASL in a subject is said to be increased when it is measurably greater than the pH of ASL of an untreated subject. In one embodiment, the pH of ASL in a subject is said to be increased when it is measurably greater than the pH of ASL of the same subject measured prior to or distant in time from treatment according to a method of the present disclosure.

Such methods of increasing the pH of airway surface liquid are described in Example 1. Remarkably, rescue of ASL pH is observed over a wide range of AmB:sterol concentrations. Accordingly, the method of increasing ASL pH described herein has significant implications for clinical applications.

In certain embodiments, the increase in pH can be 0.1 pH units to 2.0 pH units. In certain embodiments, the increase in pH can be 0.1 pH units to 1.0 pH units. In certain embodiments, the increase in pH can be 0.3 pH units to 1.0 pH units. In certain embodiments, the increase in pH can be 0.3 pH units to 1.0 pH units. In certain embodiments, the increase in pH can be 0.5 pH units to 0.9 pH units. In certain embodiments, the increase in pH can be 0.5 pH units to 0.8 pH units. In certain embodiments, the increase in pH can be 0.6 pH units to 0.8 pH units. In certain embodiments, the increase in pH can be about 0.7 pH units. In certain embodiments, the increase in pH can be 0.1 pH units to 0.5 pH units. In certain embodiments, the increase in pH can be 0.1 pH units to 0.4 pH units. In certain embodiments, the increase in pH can be 0.2 pH units to 0.4 pH units. In certain embodiments, the increase in pH can be 0.1 pH units to 0.3 pH units. In certain embodiments, the increase in pH can be 0.2 pH units to 0.3 pH units. In certain embodiments, the increase in pH can be 0.1 pH units to 0.2 pH units.

In certain embodiments, the increase in pH is by apical addition of any one of the compositions disclosed herein.

In certain embodiments, the methods described herein are useful for increasing the pH of airway surface liquid in a patient regardless of their genotype, including a patient having any one of various CF genotypes that are typically non-responsive or minimally responsive to treatment with conventional CF modulator/corrector therapeutics.

Accordingly, in certain embodiments, the methods of increasing ASL pH described herein are agnostic to the patient's CF genotype.

In certain embodiments, any of the methods disclosed herein increase ASL pH in patients having refractory or resistant CF. In some embodiments, the CF is refractory or resistant to one or more CF treatments, such as ivacaftor; or the combination of elexacaftor, tezacaftor, and ivacaftor.

In certain aspects, provided herein is a method of restoring anion transport, increasing airway surface liquid hydration and height, thereby decreasing the viscosity of airway surface liquid in a patient having CF, comprising administering to a patient having CF a therapeutically effective amount of the pharmaceutical composition of the present disclosure.

In some embodiments, restoration of anion secretion (e.g., bicarbonate secretion) leads to increases in airway surface liquid pH, increased airway hydration, increased airway surface liquid height, increases in the antimicrobial activity of airway surface liquid, or a combination thereof. These improvements in the properties of airway surface liquid may result in clinical improvements in mucociliary clearance, measures of lung function (e.g., FEV1), patient health related quality of life (HRQOL), or a combination thereof.

In certain embodiments, HRQOL is measured using the Cystic Fibrosis Questionnaire (CFQ). Henry, B. et al., *Qual Life Res.* 2003 February; 12 (1): 63-76. In some embodiments, HRQoL is measured using the Cystic Fibrosis Questionnaire Revised (CFQ-R). Wenninger, K. et al., *Qual Life Res.* 2003 February; 12 (1): 77-85. In certain embodiments, administering the present compositions to a patient provides an increase in HRQoL domain score of at least 0.5, at least 0.8, at least 1, or at least 2 as measured by the CFQ or the CFQ-R. In some embodiments, a subject's HRQOL domain score is said to be increased when it is measurably greater than the same subject's HRQOL domain score measured prior to or distant in time from treatment according to a method of the present disclosure. In certain embodiments, a subject's HRQOL domain score is said to be increased when it is measurably greater than the HRQOL domain score of an untreated subject.

Subjects with CF may have a reduced ASL height compared to a healthy subject. Muraglia, Katrina A. et al., *Nature* 2019 March; 567 (7748): 405-408. In certain embodiments, a subject with CF has an ASL height of about 3 μm to about 4 μm. In some embodiments, the methods described herein increase the ASL height of a subject with CF to the ASL height of a healthy subject (e.g., to an ASL height of about 9 μm to about 10 μm).

In certain embodiments, the methods described herein increase a subject's ASL height by about 1 μm to about 8 μm, about 1 μm to about 5 μm, about 1 μm to about 3 μm, about 2 μm to about 8 μm, about 2 μm to about 5 μm, about 3 μm to about 8 μm, about 3 μm to about 5 μm, about 5 μm to about 7 μm, or about 6 μm. In some embodiments, a subject's ASL height is said to be increased when it is measurably greater than the same subject's ASL height measured prior to or distant in time from treatment according to a method of the present disclosure. In certain embodiments, a subject's ASL height is said to be increased when it is measurably greater than the ASL height of an untreated subject.

In certain aspects, provided herein is a method of decreasing the viscosity of airway surface liquid, comprising administering to a subject in need thereof an effective amount of the pharmaceutical composition of the present disclosure, thereby decreasing the viscosity of airway surface liquid in the subject; wherein the administration is pulmonary.

In certain embodiments, the subject has CF, NCFBE, or COPD.

In certain embodiments, the subject has CF.

In certain embodiments, the pharmaceutical composition is administered to an airway of the subject by a dry powder aerosol.

In certain embodiments, the pharmaceutical composition is administered to the bronchial airways of the subject by a dry powder aerosol.

In certain embodiments, an airway of a subject refers to the so-called conducting or bronchial airways, i.e., any or all of the following pulmonary structures: trachea, bronchi, and bronchioles in the lower respiratory tract.

In certain embodiments, the methods described herein are useful for decreasing the viscosity of airway surface liquid in a patient having any one of various CF genotypes that are typically non-responsive or minimally responsive to treatment with conventional CF therapeutics.

Accordingly, in certain embodiments, the methods of decreasing ASL viscosity described herein are agnostic to the patient's CF genotype.

In some embodiments, any of the methods disclosed herein decrease ASL viscosity in patients having refractory or resistant CF. In some embodiments, the CF is refractory or resistant to one or more CF treatments, such as ivacaftor; or the combination of elexacaftor, tezacaftor, and ivacaftor.

In accordance with each of the foregoing embodiments, in certain embodiments, the patient is a human.

In certain embodiments, the range of ages that are amenable to treatment with the compositions described herein is driven by an ability to effectively utilize a passive dry powder inhaler (DPI). Subjects below the age of 6 may not have the cognitive ability to properly perform the steps involved in use of a passive DPI. Moreover, they may lack the respiratory muscle strength needed to generate the inspiratory pressures required. Nevertheless, some passive DPIs have been approved for subjects down to age 4. Similarly, some geriatric patients may also have cognitive or atrophied muscles that prevent proper use of passive DPIs. Inspiratory pressures tend to increase with age, maximizing at about age 25, plateauing until about age 40 after which they steadily decrease. Males tend to achieve higher inspiratory pressures than females. Increases in airways disease may also negatively impact the ability for subjects to achieve the pressure drop (~1.0 kPa) needed to effectively operate the passive DPI. Subjects with poor inspiratory muscle strength can be identified based on their ability to achieve a 1.0 kPa inspiratory pressure with an In-Check dial. In accordance with each of the foregoing embodiments, in certain embodiments, the patient is between the ages of 4 and 80 years old.

In certain embodiments, the patient is at least 4 years old. In certain embodiments, the patient is at least 6 to about 18 years old. In some embodiments, the patient is under the age of about 80 years old with acceptable inspiratory muscle strength. In certain embodiments, the patient is about 60 to about 70 years old. In some embodiments, the patient is about 70 to about 80 years old.

In certain embodiments, any of the methods disclosed herein permeabilize the apical membrane. In certain embodiments, any of the methods disclosed herein permeabilize the apical membrane to protons. In certain embodiments, any of the methods disclosed herein permeabilize the apical membrane to bicarbonate anions.

Drug Substance

The compositions described herein may be referred to as Amphotericin B Cystetic for Inhalation (ABCI), which may be used as an ion channel prosthetic in CF patients to restore anion transport and host defense, thereby improving lung function and quality of life.

In certain embodiments, the compositions described herein comprise highly crystalline micronized particles of amphotericin B coated with a porous layer of lipids including cholesterol.

AmB is a heptaene macrolide containing seven conjugated double bonds in the trans position and 3-amino-3,6-dideoxymannose (mycosamine) connected to the main ring by a glycosidic bond.

AmB is produced as a fermentation product by a strain of *Streptomyces nodosus*. Intravenous AmB is the only approved fungicidal compound currently used to treat systemic fungal infections. Although not approved for administration via inhalation, inhaled AmB has been extensively studied for the treatment of invasive pulmonary aspergillosis.

Indeed, more than 500,000 doses of inhaled AmB have been administered with no reported serious or severe side effects. Most study publications have described inhaled AmB as being well-tolerated. Reported adverse events (AEs) were primarily related to respiratory tract irritation (e.g., cough, bronchospasm, dyspnea, wheezing). Other AEs included unpleasant taste (dysgeusia), nausea, and vomiting. The slow absorption of the drug from the lungs results in very low systemic drug levels that are often near or below the limit of quantitation. The concentration of serum creatinine, a biomarker for kidney function, generally does not change with aerosol AmB administration. Hence, targeting of AmB to the respiratory tract dramatically improves the systemic tolerability of AmB.

At neutral pH, AmB is zwitterionic with the carboxylate group (pKa=5.7) deprotonated and the amine group on the mycosamine ring (pKa=10.0) protonated. The highly crystalline zwitterionic form of AmB is practically insoluble in aqueous solutions with a solubility in water, Gamble's solution and dilute Alveofact® at 37° C. of 0.5, 0.2 and 0.2 µg/mL, respectively.

The Dose Number (Do) is a simple metric used to predict whether a compound will be reasonably absorbed from the lungs based on its solubility at the intended clinical dose.

$$Do = \frac{M_o(\mu g)/V_{ASL}(mL)}{S_{ASL}\left(\frac{\mu g}{mL}\right)}$$

Here $M_o$ is the AmB dose in ASL, $V_{ASL}$ is the volume of ASL fluid, and $S_{ASL}$ is the AmB solubility in ASL fluid. Values of Do greater than 1.0 are consistent with dissolution-limited absorption from the lungs. For $S_{ASL}$=0.2 µg/mL and $V_{ASL}$=25 mL, dissolution-limited absorption occurs for $M_o$>5 µg. The therapeutic doses of AmB are anticipated to be greater than about 1.0 mg. Under this scenario, absorption of AmB will be dissolution limited.

The slow dissolution for compositions of the present disclosure is demonstrated by the slow appearance of AmB in plasma (e.g., $t_{max}$=4 to 8 hr), and the dramatic reductions in overall systemic exposure relative to intravenous compositions of AmB. In some embodiments, systemic exposure for the inhaled compositions described herein are 100-1,000-fold less than that measured following intravenous administration of comparable AmB doses.

In certain embodiments, the absolute bioavailability of the AmB in the methods described herein is about 0.1% to about 20%, about 0.1% to about 10%, about 0.1% to about 5%, about 0.1% to about 2%, or about 0.1% to about 1%. In some embodiments, clearance of AmB from plasma is biphasic with an initial half-life for AmB dissolved in ASL on the order of 5-20 hours, followed by a very slow terminal clearance resulting from redistribution of drug from lung tissue ($t_{1/2}$~20 days). A similar biphasic clearance process is observed for AmB following intravenous administration of particulates that are initially cleared by cells of the reticuloendothelial system and later redistributed back into plasma.

The nominal dose, particle size and physical form of AmB may have an impact on the toxicity of AmB following oral inhalation in rats (US 2012/0128728 A1). Rats receiving highly amorphous AmB formulated in lipid-coated crystals comprising 50% AmB and 50% of a 2:1 molar ratio of DSPC/calcium chloride (i.e., ABIP, Nektar Therapeutics) (U.S. Pat. Nos. 7,326,691; 8,404,217; US 2012/0128728) demonstrated clinical signs of respiratory distress, tracheal and bronchial hypertrophy, tracheal inflammation, bronchial mucosal cell infiltrate and tracheal and evidence of bronchial luminal exudates. The incidence of these effects was markedly reduced for rats receiving highly crystalline AmB (crystallinity ≥76% in ABIP) with a smaller particle size.

ABIP compositions comprising highly crystalline AmB and administrated with an appropriate dose and regimen were well tolerated in nonclinical toxicity studies. They were also well-tolerated in single dose and multiple dose studies in healthy volunteers (Kugler et al.: Amphotericin B inhalation powder (ABIP) achieves significant pulmonary and low systemic amphotericin B concentrations. 16$^{th}$ Congress of the International Society of Human and Animal Mycology (ISHAM), Paris, France, Abstract O-0011, 26 Jun. 2006); Lee J. D., et al.: Amphotericin B inhalation powder (ABIP) is well tolerated with low systemic amphotericin B exposure in healthy subjects. In: Program and Abstracts of the 2$^{nd}$ Meeting of Advances Against Aspergillosis (AAA), Abstract P-118, pp. 214-215, Athens, Greece, 2006).

Increases in amorphous content can also result in a decrease in the millability of the drug substance, which can result in increases in particle size. This observation is illustrated for a wet-milling process in Example 3. These increases in crystal size have the potential to negatively impact critical quality attributes associated with the aerodynamic particle size distribution. Decreases in crystallinity of AmB from 96% to 75% resulted in increases in $X_{50}$ from 1.06 to 2.16 µm, and in $X_{90}$ from 2.14 to 5.99 µm following wet-milling in water (Example 3). The increases in AmB crystal size did not have a meaningful impact on the physicochemical properties and aerosol performance of the formulated ABCI-002 drug product. The MMAD increased from 2.9 to 3.1 µm while the $FPF_{<5\mu m}$ increased from 61 to 63%.

In some embodiments, the crystallinity of the drug substance is at least 75%, at least 90%, or at least 95%.

In certain embodiments, a small primary particle size distribution of the micronized drug particles may provide efficient delivery of the drug product to the lungs. The AmB crystals have an $X_{50}$, as determined by laser diffraction of about 0.5 µm to about 4 µm, such as about 1 µm to about 3 µm. In some embodiments, the AmB crystals have an $X_{90}$ of about 1.5 µm to about 10 µm, such as about 2.0 µm to about 8.0 µm.

Excipients

In certain embodiments, the compositions described herein comprise highly crystalline AmB particles coated with a porous layer comprising two phospholipids (HSPC and DSPG), cholesterol, and calcium chloride. These materials may exhibit complex phase behavior that directly impacts the physicochemical and aerosol properties of the composition. This in turn may have an impact on the efficacy, safety, and tolerability of the formulated drug product.

Phospholipids are a class of lipids comprising a glycerol or sphingosine backbone, to which are attached one or more fatty acids and a phosphate group with an alcohol linked to it. The phosphate group can be modified with simple organic molecules such as choline, ethanolamine, or serine. Phospholipids are amphiphilic molecules with the two fatty acid acyl chains being lipophilic while the modified phosphate group being hydrophilic. Phospholipids self-assemble to form membranous structures in water. They are ubiquitous in mammalian cell membranes.

Hydrated phospholipid bilayers exhibit thermotropic phase behavior. With increases in temperature, the acyl chains undergo a phase transition from a 'gel phase' (so) where the acyl chains are present in a highly ordered, solid-like all-trans configuration, to a disordered 'liquid crystalline phase' (ld), where increases in gauche conformer content in the acyl chains leads to disordered, liquid-like packing. The gel to liquid crystal phase transition temperature is sometimes referred to as the main transition temperature, or $T_m$.

The $T_m$ of phospholipids depends critically on the length and degree of saturation of the acyl chains, and to a lesser extent, the nature of the headgroup. Table 2 provides a comparison of the $T_m$ values of various hydrated phospholipids.

TABLE 2

Hydrated Gel to Liquid Crystal Main Transition Temperatures of Various Phospholipids

| Phospholipid Acronym | Common Name | Acyl Chains | $T_m$ (° C.) |
|---|---|---|---|
| DLPC | Dilauroylphosphatidylcholine | 12:0/12:0 | −2 |
| DMPC | Dimyristoylphosphatidylcholine | 14:0/14:0 | 24 |
| DPPC | Dipalmitoylphosphatidylcholine | 16:0/16:0 | 41 |
| DSPC | Distearoylphosphatidylcholine | 18:0/18:0 | 55 |
| HSPC | Hydrogenated soy phosphatidylcholine | ~89% 18:0/18:0; 11% 16:0/16:0 | 53.6 |
| DOPC | Dioleylphosphatidylcholine | 18:1/18:1 | −19 |
| DLPC | Dilinoleylphosphatidylcholine | 18:2/18:2 | −57 |
| DSPG | Distearoylphosphatidylglycerol | 18:0/18:0 | 55 |
| DSPS | Distearoylphosphatidylserine | 18:0/18:0 | 68 |
| DSPE | Distearoylphosphatidylethanolamine | 18:0/18:0 | 74 |

Increases in the length of the acyl chains for phosphatidylcholines from 12 to 18 leads to increases in the hydrated $T_m$ from −2 to 55° C. Introduction of unsaturation into the acyl chains leads to dramatic reductions in $T_m$ to values less than 0° C. Changes in the nature of the headgroup also lead to differences in $T_m$, with the $T_m$ in phosphatidylethanolamine (PE)>phosphatidylserine (PS)>phosphatidylglycerol (PG)~phosphatidylcholine (PC). The hydrated $T_m$ values for HSPC and DSPG are 53.6 and 55° C., respectively.

Cell membranes are inherently multicomponent systems comprising various species of lipids and proteins. The physical properties and biological function of cell membranes are tightly coupled to the arrangement and distribution of lipids within the phospholipid bilayer. Indeed, lipids may phase separate into different domains within a bilayer depending upon their composition. Chol is abundant in cell membranes, playing a critical role in maintaining the structural integrity and regulating membrane fluidity.

In certain embodiments, the compositions described herein comprise Chol. Chol may contribute to the safety and ion channel activity of the formulated drug product. The addition of Chol to saturated PL may have a significant impact on PL phase behavior both in cell membranes and in spray-dried particles.

FIG. 1 presents a phase diagram of hydrated DPPC-Chol mixtures (Ipsen J H, Karlström G, Mouritsen O G, et al. *Phase equilibria in the phosphatidylcholine-cholesterol system. Biochim Biophys Acta.* 1987; 905:162-172).

As depicted in FIG. 1, addition of Chol leads to the formation of a new phase referred to as an ordered liquid phase, (lo). Incorporation of Chol into so below ~6 mol % results in a broadening of the $T_m$ phase transition in DSC thermograms and increases in disorder in the acyl chain packing. In contrast, phospholipid acyl chains present in the disordered ld phase above $T_m$ have increased order with added Chol. At Chol concentrations between about 6 and 20 mol %, there is coexistence of two phases. Above $T_m$, the disordered liquid phase and ordered liquid phase coexist (ld-lo). Below $T_m$, the solid ordered phase coexists with the ordered liquid phase (so-lo). At high Chol concentrations (20-25 mol %), the cooperative $T_m$ phase transition is lost, with only the lo phase present. For HSPC (longer acyl chains), a similar diagram is expected, with the temperatures on the ordinate in FIG. 1 shifted upward by about 13° C.

In contrast to the fully hydrated PL described above, compositions according to embodiments described herein comprise partially dehydrated PL. For the proposed use as ion channel prosthetics, the lipids in the compositions described herein may be spray dried to form an inhaleable dry powder with low water content.

In the absence of water, the spacing between phospholipid headgroups decreases, thereby increasing van der Waals interactions between the lipid acyl chains and increasing $T_m$. For example, the $T_m$ value of DPPC increases from about 41° C. (fully hydrated) to 105° C. on lyophilization (Ohtake S, Schebor C, Palacek S P, de Pablo J. J: *Phase behavior of freeze-dried phospholipid-cholesterol mixtures stabilized with trehalose. Biochim Biophys Acta.* 2005, 1713:57-64).

For spray-dried DSPC powders, the $T_m$ increases from 55° C. (fully hydrated) to 71° C. at 75% RH, to 85° C. at 11% RH, to 102° C. at <3% RH (Pikal-Cleland K A, Zhang J, Lechuga-Ballesteros D, Tarara T E, Weers J G: *The impact of Ca$^{2+}$ binding on the packing structure of dry phospholipids.* Presented at CRS Annual Meeting, Seoul, Korea, 2002).

For current marketed spray-dried compositions comprising PL (e.g., TOBI® Podhaler™, Bevespi® Aerosphere, Breztri® Aerosphere, and Inbrija®), a goal has been to maintain the PL in the so phase during particle formation, in the collector during spray-drying, and on storage over the shelf-life of the product. As a result, these products utilize long-chain saturated phosphatidylcholines, such as DPPC and DSPC, as the principal shell-forming excipient.

During spray drying of an aqueous feedstock, evaporative cooling of the atomized droplets maintains the droplet temperature just above room temperature, and far below the hydrated $T_m$ of the PL (41 to 55° C.). This is true even when the inlet temperature on the spray dryer exceeds $T_m$. After particle formation, the outlet temperature and collector jacket temperature in the spray dryer are maintained below the $T_m$ in the dehydrated state. Hence, the acyl chains are maintained in the so phase throughout the manufacturing process and on storage.

For liquid feedstocks comprising DPPC or DSPC, spray drying the so phase enables the formation of discrete spray-dried particles where the surface composition, surface morphology, size, density, porosity of the particles can all be effectively controlled. Moreover, long-chain saturated PLs are believed to be biocompatible in the lungs, due to their presence in endogenous lung surfactant, and natural, rapid clearance pathways from the lungs.

In contrast, spray drying aqueous feedstocks of unsaturated PL with $T_m$ values <0° C. presents a significant challenge. Evaporation of water during spray drying may require an outlet temperature significantly higher than $T_m$. In this scenario, the PL acyl chains are present in the ld phase during particle formation and the drying process may therefore lead to large agglomerates of fused particles. This may result in low manufacturing yields and aerodynamic particle size distributions that are not suitable for inhalation as dry powder aerosols.

In certain embodiments, the compositions described herein comprise saturated phospholipids with longer acyl chains (e.g., 16:0/16:0 or 18:0/18:0). In some embodiments, the compositions described herein comprise DPPC, DSPC, HSPC, DSPG, or a combination thereof.

Calcium ions may bind to the phosphate group in phospholipids, displacing water molecules and condensing packing between PL molecules. For spray-dried DSPC powders, the addition of Ca ions may improve the environmental robustness (T, RH) of dehydrated powders, particularly at RH values that typically result in significant increases in capillary forces (e.g., 75% RH). In some embodiments, the ratio of PL/Ca is less than 4.0 mol/mol, less than 3.0 mol/mol, or about 2.0 mol/mol (U.S. Pat. Nos. 8,709,484; 7,442,388; incorporated by reference). In some embodiments, it may be undesirable to decrease the PL/Ca ratio below the stoichiometric 2.0 mol/mol ratio, as excess calcium chloride below this ratio may increase the hygroscopicity of the powder.

Above $T_m$ in either the ld or lo phases, the spray-dried powders may become 'sticky' viscous liquids. These cohesive powders tend to negatively impact powder flowability and aerosol performance. This observation may be analogous to what occurs for highly disordered amorphous solids above their glass transition temperature, $T_g$. Spray-dried powders with phase separated so and lo domains tend to have poor powder properties. Hence, it may be desirable to maintain the lipids in the so phase.

The impact of added Chol on the phase behavior of PL in dry powder formulations is poorly understood. Differential scanning calorimetry thermograms of compositions according to embodiments described herein suggest that the lo phase is fully solubilized into the so phase at a Chol/PL ratio below about 0.05 w/w (≤9.4 mol % Chol) (Example 4). Hence, in the dehydrated state the so phase can solubilize a greater percentage of Chol than was observed for hydrated DPPC-Chol mixtures (FIG. 1). Maintenance of the so phase results in $T_m$ values that are >90° C.

Decreases in DSPG content in ABCI powders from a HSPC/DSPG ratio of 2.3 mol/mol (~7/3 mol/mol) as utilized in AmBisome® and some lung surfactant preparations, to an HSPC/DSPG ratio of 9.0 w/w or higher may also improve physicochemical and aerosol properties of spray-dried AmB/Chol powders (Example 12).

In some embodiments, increases in the HSPC/DSPG ratio decrease the hygroscopicity of compositions described herein at high relative humidity (RH) (Example 5). DSPG is an anionic phospholipid that may be provided as the sodium salt. Addition of calcium ions may displace the sodium ions, which then may combine with chloride ions from the calcium chloride to form hygroscopic sodium chloride domains in the spray-dried powder. At high RH the NaCl deliquesces (i.e., absorbs moisture from the air and dissolves in it). This may contribute to the stickiness of compositions according to embodiments described herein at high RH.

Other PLs may provide improvements in ASL pH and acceptable powder and aerosol properties. Their utility may be determined by using the characterization methods described in the Examples section. In certain embodiments, compositions described herein comprise sphingomyelin, phosphatidylserine (PS), or a combination thereof. In some embodiments, the compositions described herein comprise phospholipids with longer saturated acyl chains (e.g., n≥16).

Drug Product Compositions

In some embodiments, the compositions described herein comprise the drug particles that are phase separated from the lipid excipients in their own crystalline domain. That is, AmB and Chol are not complexed in amorphous nanoparticles as in the case of US 2019/0083517, US 2020/0352970. Nor is the AmB encapsulated within liposomes as is the case in AmBisome® (U.S. Pat. No. 5,965,156).

The presence of Chol in the compositions described herein may be critical both from an efficacy and safety perspective.

From an efficacy perspective, the presence of Chol may preserve ion channel activity at both low and high AmB concentrations. Although the mechanism is not clearly understood, ion channel activity tends to diminish at higher AmB concentrations in the absence of Chol (Example 10). This trend was observed both for neat AmB and for ABIP, which contains no Chol.

In US 2019/0083517, Burke et al. disclosed compositions of AmB and Chol for the restoration of airway surface physiology in CF lung epithelia, wherein the molar ratio of Chol/AmB was claimed to be in the range of from 2.6 to 50 mol/mol. In US 2020/0352970, Burke et al. disclosed methods for treating CF with small molecule bicarbonate channels. In this case the Chol/AmB ratio was between 1.0 and 12.0 mol/mol. In the present disclosure, it has been surprisingly discovered that ion channel activity is maintained at Chol/AmB ratios significantly lower than 1.0 mol/mol (Example 10). In some embodiments, the nominal ratio of Chol/AmB ratio is between 0.4 and 1.2 mol/mol. In some embodiments, due to enrichment of the drug substance in the spray-drying process, the actual range of Chol/AmB ratios in the final spray-dried powders is about 0.33 to about 1.0 mol/mol. In certain embodiments, significant improvements in ASL pH comparable that achieved with AmB:Chol complexes (i.e., >0.1 pH units) is maintained down to nominal Chol/AmB ratios of 0.05 mol/mol.

Maintaining ion channel activity at lower Chol/AmB ratios in spray-dried powders comprising PL may minimize phase separation of a Chol-rich lo phase, due to its negative effects on powder properties.

The AmB:Chol complexes disclosed in US 2019/0083517 and US 2020/0352970 achieve improvements in ASL pH in CuFi-1 and CuFi-4 epithelia of ~0.1 to 0.2 pH units. The ASL pH remains slightly acidic (pH~6.90-6.95). In CuFi-4 cells, the CFTR modulator ivacaftor achieves comparable improvements in ASL pH as the AmB:Chol complexes. In contrast, the improvements in ASL pH in CuFi-1 cells observed with compositions according to embodiments described herein, are about 0.4 to 0.5 pH units, i.e., about two-fold to five-fold larger than is observed with AmB:Chol complexes and ivacaftor. In some embodiments, the ASL pH is increased from being slightly acidic with AmB:Chol complexes to slightly basic (PH~7.2) with the compositions described herein. Achieving a slightly basic pH may improve the activity of many of the cationic peptides involved in host defense (e.g., defensins).

From a safety perspective, it is known that the presence of Chol in the compositions according to embodiments described herein prevents the extraction of sterols from mammalian cell membranes into an extramembranous sterol sponge phase. This has been demonstrated to be a primary mechanism for toxicity in Chol-free compositions of AmB. It had been suggested that this protective effect is maintained down to Chol/AmB ratios of 1.0 mol/mol US 2019/0083517, US 2020/0352970. It has been surprisingly discovered that this protective effect is maintained for red blood cell membranes down to Chol/AmB ratios of 0.4 mol/mol or less (Example 15).

FIG. 2 is a ternary phase diagram detailing the compositions of various AmB/lipid compositions. In certain embodiments, the compositions described herein are defined by the shaded triangle. Two sides of the triangle are defined by a range of Chol/AmB molar ratios, (e.g., 1.2 mol/mol and 0.4 mol/mol). The third side of the triangle is defined by a ratio of Chol/PL (0.05 w/w) that eliminates phase separation of the lo phase. The phase diagram and various compositions are discussed in greater detail in Example 1.

In some embodiments, the nominal daily dose of AmB for the restoration of ASL pH in patients with CF is about 0.1 to about 10 mg, or about 0.2 mg to about 6 mg.

In some embodiments, estimates of the drug loading based on the nominal dose and tapped density of the powders are presented in Example 16. In certain embodiments, the drug loading is about 0.1% to about 50% w/w, such as about 0.5% to about 20% w/w.

Physicochemical Properties

The physicochemical properties of the compositions described herein may depend on the feedstock composition (e.g., solids content, PFOB content), and drying conditions in the spray dryer. The ranges described below are based on the results for batches of compositions presented in the Examples.

In some embodiments, the small porous particles have relatively low densities, although not as low as compositions spray-dried from solution-based liquid feedstocks. In some embodiments, the poured bulk density is about 0.04 to about 0.12 g/cm$^3$, and the tapped density is about 0.08 to about 0.20 g/cm$^3$.

Carr's Index provides a measure of the flow properties of the bulk powder (Table 3). Fine particles with a geometric size less than 5 μm, such as those according to embodiments described herein, are highly cohesive with very poor powder flow properties.

TABLE 3

Relationship between Carr's Index and Bulk Powder Flow Properties

| Carr's Index | Description of Powder Flow |
|---|---|
| ≤10 | Excellent, free-flowing powders |
| 11-15 | Good, free-flowing powders |
| 16-20 | Fair powder flow |
| 21-25 | Passable powder flow |
| 26-31 | Cohesive, poor powder flow |

TABLE 3-continued Relationship between Carr's Index
and Bulk Powder Flow Properties

| Carr's Index | Description of Powder Flow |
|---|---|
| 32-37 | Very cohesive, very poor powder flow |
| >38 | Approximately no powder flow |

Nonetheless, it is possible to fill fine, cohesive powders accurately and precisely with drum fillers (e.g., machines from Harro Höfliger) to achieve relative standard deviations less than about 3% on fill masses as low as about 1.0 mg.

In some embodiments, the powders described herein have a Carr's Index of about 20 to about 50, such as about 24 to about 30. Powders with lower Carr's Index values may have noticeably improved powder flow properties, decreased variability in measurements of size and density, and an increased production yield. Compositions that have lo domains in the spray-dried powder have a Carr's Index of about 40, which tends to lead to low yields and difficulty in handling (e.g., filling and fluidizing) the powders.

In certain embodiments, a relatively high Carr's Index value observed (suggesting poor, cohesive flow, i.e., a Carr's index value of 20-32) does not negatively impact the flow properties of importance for development of a portable dry powder inhaler.

Primary particle size distributions may be determined by laser diffraction (see, e.g., Characterization Methods, below). In certain embodiments, the powders described herein have an $X_{10}$ of about 0.40 to about 1.2 µm, an $X_{50}$ of about 1.5 to about 3.5 µm, and an $X_{90}$ of about 4.0 to about 8.0 µm.

Water contents may be determined by coulometric Karl Fischer titrimetry. In certain embodiments, the water content of the powders described herein is about 1.5% to about 6% w/w.

In certain embodiments, the physicochemical properties of the powders can be modulated throughout the ranges described via variations in manufacturing process parameters.

Aerosol Performance

In certain embodiments, the compositions described herein target the bronchial airways. In this regard, it tends to be beneficial to minimize extrathoracic drug deposition in the mouth and throat and in the alveoli, while maximizing deposition in the large and small airways within the lungs.

In the context of in vitro aerosol performance metrics, the compositions according to embodiments described herein have an emitted dose from a portable dry powder inhaler at a 4 kPa pressure drop and 4 L inhaled volume of at least 70%, at least 80%, at least 90% or at least 95%. In some embodiments, the compositions described herein are formulated to pass the delivered dose uniformity (DDU) regulatory requirements as delineated in the FDA Draft Guidance on: "*Metered Dose Inhaler (MDI) and Dry Powder Inhaler (DPI) Products-Quality Considerations* (April 2018)", with a standard deviation on mean ED values of 6% or less.

In certain embodiments, in a Next Generation Impactor (NGI) operated at a 4 kPa pressure drop with a 4 L inhaled volume, the mass median aerodynamic diameter (MMAD) of the compositions described herein is about 1.5 to about 4.0 µm, such as about 2.0 to about 3.5 µm.

The pattern of deposition within the NGI may be important. In accordance with the desired pattern of regional deposition detailed above, it is beneficial to minimize deposition in the USP throat and impactor stages 1 and 2 (referred to as the 'coarse fraction'), and in the 'extrafine fraction' on stages 6 to filter, while maximizing deposition on stages 3, 4 and 5 (referred to as the 'airways fraction'). In certain embodiments, deposition in the coarse fraction is less than 30%, less than 20%, or less than 10% w/w of the nominal dose. In some embodiments, deposition in the extrafine fraction is less than 16%, less than 12%, or less than 8% of the nominal dose. In certain embodiments, deposition in the airways fraction is at least 40%, at least 50%, at least 60%, or at least 70% of the nominal dose.

In certain embodiments, the fine particle fraction less than 5 µm ($FPF_{<5 \mu m}$) expressed as a percentage of the emitted dose is at least 40%, at least 50%, at least 70%, or at least 90% w/w.

In certain embodiments, the flow rate dependence of the total lung dose (TLD) in an Alberta Idealized Throat (AIT) model between pressure drops of 1.0 and 6.0 kPa is less than 40% or less than 15%.

In certain embodiments, the target fill mass is about 5 to about 40 mg, such as about 10 to about 20 mg. In some embodiments, the compositions described herein are administered to a subject with a portable capsule-based dry powder inhaler (DPI). In certain embodiments, the DPI has a receptacle with a volume of about 0.30 cm³ (size 3 capsule) to about 0.37 cm³ (size 2 capsule).

In certain embodiments, the DPI is a variant of the RS01 DPI (Plastiape, Osnago, Italy). Variants of the RS01 differ in the size of capsule they accommodate (size 3 to size 0), and in their resistance to airflow (R=0.06 to 0.16 cm $H_2O^{0.5}$ $L^{-min}$). In some embodiments, the DPI is medium to high resistance (e.g., R is about 0.10 to about 0.30 cm $H_2O^{0.5}$ $L^{-min}$). In certain embodiments, the DPI is a variant of the RS01 DPI with a resistance of about 0.14 cm $H_2O^{0.5}$ $L^{-1}$ min. In certain embodiments, medium to high resistance DPIs limit extrathoracic deposition while also limiting the potential for post-inhalation cough.

In some embodiments, the compositions described herein are administered with a Handihaler (Boehringer Ingelheim), a RS00 (Plastiape) or Aerolizer® (Novartis) (U.S. Pat. No. 3,991,761; incorporated by reference), a Breezhaler® (US 2007/0295332; incorporated by reference) (Novartis) In certain embodiments, the compositions described herein are administered with a Turbospin (PH&T) or a variant thereof such as a T-326 (Podhaler™) (Novartis) as described in U.S. Pat. Nos. 8,069,851 and 7,559,325 (both incorporated by reference), or an AIR inhaler (Acorda Therapeutics).

In certain embodiments, the compositions described herein are administered with a single-use disposable inhaler. In some embodiments, the single-use disposable inhaler is a TwinCaps (Hovione), a Dose1® (Micro Engineering Solutions), a ICOone™ (Iconovo), or a Cyclops® (Pure IMS).

In some embodiments, the dry powder compositions of the present disclosure are administered intranasally to increase ASL pH in the nose and increase the nasal potential difference. Devices contemplated include Aptar's Unidose system.

Manufacturing

A mixture of cholesterol and phospholipids may be prepared by dissolution in organic solvents. In certain embodiments, a lipid mixture comprising HSPC/DSPG/Chol in a 54/24/22 w/w/w ratio is prepared. Depending on the desired composition, the lipid mixture may be supplemented with additional PL and calcium chloride.

In some embodiments, a method of preparing the compositions described herein comprises dispersing the lipid mixture in water to form multilamellar liposomes. In certain embodiments, this step involves addition of the lipids to hot water at a temperature greater than the hydrated $T_m$ of the lipids. In some embodiments, the temperature of the water is 65° C. to 90° C. In some embodiments, the dispersion is accomplished with a high shear mixer, such as an UltraTurrax® T-50.

In some embodiments, the method further comprises adding a fluorinated (FC) blowing agent, (e.g., perfluorooctyl bromide (PFOB, Perflubron), perfluorooctyl ethane (PFOE), or perfluorodecalin (PFD)) while mixing to form a coarse FC-in-water emulsion comprising micron-sized emulsion droplets. In certain embodiments, the coarse emulsion is homogenized under high pressure with a MicroFluidizer®, or a piston-gap homogenizer (e.g., Avestin Emulsiflex®) to form a submicron emulsion. In some embodiments, the pressure during homogenization is about 10,000 to about 20,000 psi, and homogenization is conducted either for a set period (dependent on batch size), or for a specified number of discrete passes. In some embodiments, a single discrete pass is conducted at the end of a set period process to ensure that all droplets are passed through the homogenizer at least once.

In some embodiments, the method further comprises adding the drug substance to the submicron emulsion under mixing. In certain embodiments, the addition is performed in a one pot process. In some embodiments, the resulting complex dispersion of emulsion droplets and suspended drug particles is mixed with a high shear mixer or passed through the homogenizer.

In some embodiments, the emulsion preparation and wet-milling of the drug are conducted in separate tanks in a two pot process. In certain embodiments, this allows for in-process sizing of the micronized drug particles by laser diffraction or dynamic light scattering. In some embodiments, the two pots are then combined into one, while mixing.

In certain embodiments, the emulsion preparation and wet-milling steps are conducted with concentrated emulsions/suspensions to limit the amount of liquid processed through the homogenizer. In some embodiments, water is added in the final step to achieve the target solids content and PFOB volume fraction in the final liquid feedstock.

In some embodiments, the feedstock is sprayed into a current of warm filtered air that evaporates the solvents and conveys the dried product to a cyclone separator or baghouse. In certain embodiments, the spent air is then exhausted with the evaporated solvent. In some embodiments, operating conditions of the spray-dryer such as the inlet and outlet temperature, feed rate, atomization pressure, flow rate of the drying air and nozzle configuration can be adjusted to produce the desired particle size, moisture content, and production yield for the resulting dry particles. In certain embodiments, the method further comprises setting a Niro PSD-1 scale spray dryer to have an inlet air temperature between 80° C. and 200° C., an air outlet temperature between about 40° C. and 120° C., a liquid feed rate between 30 g/min and 120 g/min, a total air flow between 50 scfm and 230 scfm, and an atomization airflow between 30 and 90 scfm. The solids content in the spray drying feedstock will typically be between 0.5% w/v and 10% w/v, and the blowing agent concentration will typically be between 3% and 30% v/v. In some embodiments, the desired settings depend, at least in part, on the scale and type of equipment used.

As the water in the atomized droplets is evaporated, the diameter of the aqueous atomized droplet recedes and the slowly diffusing emulsion droplets and AmB crystals are concentrated at the air/water interface with a hollow droplet core. When the higher boiling oil phase evaporates, it leaves behind pores in the spray-dried particles. The final particle morphology comprises porous lipid particles with embedded drug particles.

In certain embodiments, the outlet temperature and the collector jacket temperature (if utilized to control the RH in the collector), must be less than the lowest lipid main transition temperature. In certain embodiments in which the Chol/PL ratio is <0.05 w/w, the lowest lipid main transition temperature is more than 80° C., providing for outlet and collector jacket temperatures of 70° C. or greater. Decreases in the Chol/PL ratio and increases in the HSPC/DSPG ratio (Examples 9 and 12) may eliminate the Chol-rich phase, thereby providing for higher outlet temperatures, increases in production rate, and reductions in residual solvents in the spray-dried powder.

If the atomized droplets are dried too quickly, the benefits of the fine emulsion droplets may be lost. Hence, it may be beneficial to control the drying rate.

Definitions

The terms "treat" and "treating" as used herein refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

A "subject" or "patient" as used herein refers to a living mammal. In various embodiments, a patient is a non-human mammal, including, without limitation, a mouse, rat, hamster, guinea pig, rabbit, sheep, goat, cat, dog, pig, horse, cow, or non-human primate. In certain embodiments, a patient is a human.

"Effective amount" as used herein refers to any amount that is sufficient to achieve a desired biological effect.

"Therapeutically effective amount" as used herein refers to any amount that is sufficient to achieve a desired therapeutic effect, e.g., treating CF.

"Active ingredient", "therapeutically active ingredient", "active agent", "drug" or "drug substance" as used herein means the active ingredient of a pharmaceutical, also known as an active pharmaceutical ingredient (API).

"Amorphous" as used herein refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid-like properties occurs at a "glass transition", typically defined as a second-order phase transition.

"Crystalline" as used herein refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically a first-order phase transition ("melting point"). In the context of the present disclosure, a crystalline active ingredient means an active ingredient with crystallinity of greater than 75%. In certain embodiments, the crystallinity is suitably greater than 90%. In other embodiments, the crystallinity is greater than 95%. In other embodiments, the crystallinity is less than 10%, or less than 5%.

"Drug Loading" as used herein refers to the percentage of active ingredient(s) on a mass basis in the total mass of the composition.

"Mass median diameter" or "MMD" or "$X_{50}$" as used herein means the median diameter of a plurality of particles, typically in a polydisperse particle population, i.e., consisting of a range of particle sizes. The $X_{50}$ values as reported herein are determined by laser diffraction (Sympatec Helos, Clausthal-Zellerfeld, Germany), unless the context indicates otherwise.

"Tapped densities" or $\rho_{tapped}$ as used herein were measured in a fashion similar to Method I, as described in USP <616>Bulk Density and Tapped Density of Powders. Tapped densities represent a closer approximation to particle density than poured bulk densities, with measured values that are approximately 20% less than the actual particle density.

"Mass median aerodynamic diameter" or "MMAD" as used herein refers to the median aerodynamic size of a plurality of particles, typically in a polydisperse population. The "aerodynamic diameter" is the diameter of a unit density sphere having the same settling velocity, generally in air, as a powder and is therefore a useful way to characterize an aerosolized powder or other dispersed particle or particle composition in terms of its settling behavior. The aerodynamic particle size distributions (APSD) and MMAD are determined herein by cascade impaction, using a NEXT GENERATION IMPACTOR™ (Copley Scientific). In general, if the particles are aerodynamically too large, fewer particles will reach specific regions of the lungs. If the particles are too small, a larger percentage of the particles may be exhaled. In contrast, $d_a$ represents the aerodynamic diameter of a single particle.

"Nominal Dose" or "ND" as used herein refers to the mass of drug loaded into a receptacle (e.g., capsule or blister) in a non-reservoir based dry powder inhaler. ND is also sometimes referred to as the metered dose.

"Emitted Dose" or "ED" as used herein refers to an indication of the delivery of dry powder from an inhaler device after an actuation or dispersion event from a powder unit. ED is defined as the ratio of the dose delivered by an inhaler device to the nominal or metered dose. The ED is an experimentally determined parameter and may be determined using an in vitro device set-up which mimics patient dosing. ED is also sometimes referred to as the delivered dose (DD).

"Fine particle fraction" (FPF) as used herein, refers to the percentage of active ingredient in the emitted dose with an aerodynamic size less than 5 μm. The aerodynamic particle size distributions (APSD) is determined herein by cascade impaction, using a NEXT GENERATION IMPACTOR™.

"Solids Content" as used herein refers to the concentration of active ingredient(s) and excipients dissolved or dispersed in the liquid solution or dispersion to be spray-dried.

As used herein, an "airway of a subject" refers to any or all of the following pulmonary structures: trachea, bronchi, and bronchioles.

The term "about" refers to variations in numerical values typically encountered by one of skill in the art of respirable compositions, including variations of plus or minus 0.1%, 0.5%, 1%, 2%, 3%, 4%, 5%, 6%, 7%, 8%, 9%, or 10% of a numerical value described herein.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

Unless otherwise stated, or clear from the context, numerical ranges include both the endpoints and any value between.

EXAMPLES

The various aspects and embodiments of the present disclosure will be further clarified with reference to the following examples. The examples are illustrative in nature and should not be understood to limit the subject matter of the present disclosure.

Characterization Methods

Amphotericin B (AmB) Content and Purity. AmB content and purity in formulated bulk powder or aerodynamic particle size distribution (APSD) samples were determined by reverse phase high performance liquid chromatography (RP-HPLC) with detection at 383 nm. Samples were analyzed with an Agilent 1260 Infinity II HPLC system (Wilmington, DE, USA). Separation was achieved with Agilent Infinity-Lab Poroshell 120 EC-C18, 3.0×150 mm, (2.7 μm) column using a gradient method (solvent A=10 mM acetate buffer, pH 4.2; solvent B=acetonitrile/methanol, 1.0 v/v). AmB was quantified using a single-point calibration using the USP certified reference standard.

Cholesterol Content. Cholesterol content was determined by RP-HPLC with detection at 210 nm. Samples were analyzed with an Agilent 1260 Infinity II HPLC system (Wilmington, DE, USA). Separation was achieved with Haisil Clipeus™ C18 column (5 μm) using an isocratic method (acetonitrile/isopropanol, 1.0 v/v). Cholesterol was quantified using a single-point calibration using Cholesterol HP, Ph. Eur/USP-NF raw material (Carbogen Amcis, Beuvry-la-Foret, France).

Primary Particle Size Distributions. Primary particle size distributions were determined via laser diffraction (Sympatec GmbH, Clausthal-Zellerfeld, Germany). The Sympatec H3296 unit was equipped with an R2 lens, an ASPIROS micro dosing unit, and a RODOS/M dry powder-dispersing unit. Approximately 2 mg to 5 mg powder was filled into an ASPIROS tube and fed at 5 mm/s into a RODOS operated with 4 bar dispersion pressure and 65 mbar vacuum. Powders were introduced at an optical concentration of approximately 1% to 5% and data were collected over a measurement duration up to 15 seconds. Particle size distributions were calculated by the instrument software using the Fraunhofer model. Reported values represent the mean of three independent measurements for each collector.

Tapped Density. Tapped densities ($\rho_{tapped}$) were determined using a cylindrical cavity of known volume (0.593 cm$^3$). Powder was filled into this sample holder using a microspatula. The sample cell was then gently tapped on a countertop. As the sample volume decreased, more powder was added to the cell. The tapping and addition of powder steps were repeated until the cavity was filled, and the powder bed no longer consolidated with further tapping. The tapped density is defined as the mass of this tapped bed of powder divided by the volume of the cavity.

Bulk Density. The bulk density ($\rho_{bulk}$) represents the mass of the powder that is loaded into the sample holder to the requisite volume without tapping.

Carr's Index. Carr's index, C, provides an indication of powder compressibility. It is given by:

$$C = \frac{\rho_{tapped} - \rho_{bulk}}{\rho_{tapped}} \times 100$$

As Carr's index increases, the flowability of the powder is thought to decrease. Values of <10% are indicative of excellent free-flowing powders, values between 11-15% are associated with good free-flowing powders, between 16-20% with fair powder flow, between 21-25% passable powder flow, between 26-31% poor flow cohesive, between 32-37% very poor flow, and ≥38% approximately no flow.

Water Content. Water content was determined by Karl Fischer titrimetry using a Nittoseiko Analytech Moisture Meter CA-310 with fritless cathode and Vaporizer Model VA-300.

Dynamic Vapor Sorption. The moisture sorption isotherm at 25° C. was measured using a dynamic vapor sorption (DVS) instrument made by Surface Measurement Systems, UK. This instrument gravimetrically measures uptake and loss of water vapor by a material. The DVS system is equipped with a recording microbalance with a resolution of ±0.1 µg and a daily drift of approximately ±1 µg. In the first step of the experimental run, the sample was dried at 25° C. and 0% RH for 24 hours to bring the sample to a constant mass. Then, the instrument was programmed from 0 to 2% RH, to 5% RH, and then RH was increased in steps of 5% RH to 90% RH and decreased in steps of 5% RH from 90% to 0% RH. An equilibration criterion of dm/dt=0.005%/min was chosen for the system to achieve at each RH step before automatically proceeding to the next RH step. Sample masses between 10 and 15 mg were used in this study.

Differential Scanning calorimetry. The DSC thermogram of a given sample was measured using a TA Instruments Model Q2000 differential scanning calorimeter equipped with a Refrigerated Cooling System (New Castle, Delaware). The sample cell was purged with dry nitrogen at a flow rate of 50 cm³/min; the Refrigerated Control System (RCS) used nitrogen at a flow rate of 110 cm³/minute. Tzero aluminum pans that contained between about 5 and 10 mg of powder were hermetically sealed using a sample encapsulation press. Samples were equilibrated at −40° C., then heated at 5° C./min to 200° C.

Aerodynamic Particle Size Distributions. Aerodynamic particle size distributions (APSD) were determined utilizing the RS01 dry powder inhaler (Mod. 7 Ultra High Resistance 2 Model), USP induction port (IP), and Next Generation Impactor™ or NGI™ and conforms with USP <601> and Ph. Eur. 2.9.18. The flow control apparatus was adjusted to operate at a 4 kPa pressure drop and for a total volume of 4 L through the inhaler. The RS01 DPI variant utilized has a resistance of 0.143 cm $H_2O^{0.5}$ $L^{-1}$ min (0.045 $kPa^{0.5}$ $L^{-min}$). This corresponds to a flow rate of 44.2 L min-1 at a 4 kPa pressure drop. Approximately 10 mg was hand filled into size #3 inhalation grade HPLC capsules (VCaps, Qualicaps). The aerosol powder emitted from the inhaler was drawn through the USP IP and sized in the NGI. Each stage of the NGI, emptied capsule and device were extracted with the sample dissolution solution comprising methanol. Further dilutions were made to reduce the AmB concentration within the linearity of the detection range. The AmB mass on each stage was determined using the HPLC method described above and the fine particle dose less than 5 µm ($FPD_{<5\,\mu m}$) and mass median aerodynamic diameter (MMAD) were calculated.

Cell Lines and Growth Conditions. NuLi, CuFi-1, and CuFi-4 cells (Welsh Laboratory, University of Iowa) were grown from cryostock on Thermo Scientific BioLite Cell Culture Treated 75 cm² flasks. These flasks were previously coated with 4 mL of 60 µg/mL human placental collagen type IV (Sigma-Aldrich) for a minimum of 1 h at 37° C., rinsed twice with PBS, and then dried before seeding. The cells were cultured with 12 mL Bronchial Epithelial Cell Growth Medium (BEGM) BulletKit (Lonza CC-3170), which includes the basal medium and eight SingleQuots of supplements (bovine pituitary extract (BPE), 2 mL; hydrocortisone, 0.5 mL; hEGF, 0.5 mL; adrenaline, 0.5 mL; transferrin, 0.5 mL; insulin, 0.5 mL; retinoic acid, 0.5 mL; triiodothyronine, 0.5 mL). The gentamicin-AmB aliquot was discarded, and the medium was instead supplemented with 50 µg/mL penicillin-streptomycin (Corning Cellgro), 50 µg/mL gentamicin (Sigma-Aldrich G1397), and 2 µg/mL fluconazole (Sigma-Aldrich). The original CF transplant donors were genotyped by Integrated Genetics. Cell lines were secondarily confirmed by the ATCC repository to have the correct genotype and were free of mycoplasma contamination. MycoAlert Mycoplasma detection kit (Lonza LT07-418) was used to detect any RNA transcripts common to a broad spectrum of mycoplasma. Cell lines were confirmed to be mycoplasma-free. Cells were grown to >90% confluence at 37° C. in 5% $CO_2$, changing medium every two-three days, and then trypsinized with 4 mL 0.25% trypsin containing 1 mM EDTA (Gibco 25200-056). Trypsin was inactivated with 10 mL HEPES-buffered saline solution (Lonza CC-5024) with 1% fetal bovine serum. Cells were spun down in an Eppendorf Centrifuge 5430R at 1,500 rpm. for 5 min at room temperature and resuspended in BEGM medium for passaging. For culturing on membrane supports for differentiation, cells were resuspended after centrifugation in Ultroser G medium. This comprised 1:1 DMEM: Ham's F-12, supplemented with 4% v/v Ultroser G (Crescent Chemical) as well as 50 µg/mL penicillin-streptomycin (Corning Cellgro), 50 µg/mL gentamicin (Sigma-Aldrich G1397), and 2 µg/mL fluconazole (Sigma-Aldrich). The membrane supports used were the Corning Costar 0.4-µm 24-well plate Transwell clear polyester membrane inserts (0.33 cm²) (Corning 3470) for all studies. These membranes were coated with collagen in the same manner as the flasks detailed above, except with 100 mL collagen and only rinsed once with PBS. The inserts were seeded with 115,000 cells each. These membranes were allowed to mature at an air-liquid interface for a minimum of 14 days to reach full differentiation, with the Ultroser G medium changed once or more per week as needed. After maturation, medium was changed every seven days. For covariate control, membranes used in experiments were as close in age and maturation as possible.

For the primary cultured airway epithelial cells, lung tissue was obtained from individuals with CF who were undergoing a lung transplant or organ donation. The tissue was dissociated and the dissociated cells were directly seeded onto transwell filters and cultured at the air-liquid interface. Cultures were used at greater than three weeks post-seeding when epithelial cells were differentiated into the typical cell types of the airways and the electrical properties of the cells reflected excised tissue.

Fluorescence Microscopic Assay for Measurement of Airway Surface Liquid pH. A fresh suspension of ABCI was prepared for each experiment by dispersing approximately 2 mg of ABCI in approximately 100 μL of perfluorohexane, PFH (FC-72, Sigma-Aldrich) to reach a final concentration of approximately 1 mM AmB. Following dissolution in methanol, the AmB concentration in the stock suspension was measured in triplicate by absorbance spectroscopy. Concentrations were calculated from the absorbance at 406 nm ($\epsilon_{406}$=164,000 M$^{-1}$ cm$^{-1}$) using Beer's law. Next, the stock suspensions were diluted with PFH to achieve suspension AmB concentrations ranging from ~0.5 to 50 μM.

Small-diameter NuLi and CuFi cells were used for measurement of the ASL pH. The ratiometric pH indicator SNARF-conjugated dextran (Molecular Probes) was used to measure ASL pH. SNARF powder was suspended via sonication in PFH and distributed onto the apical surface of the cells. ASL pH was measured 2 h later. SNARF was excited at 514 nm and emission was recorded at 580 nm and 640 nm using a Zeiss LSM 800 microscope equipped with a water immersion lens for cell line cultures at a magnification of 40×. To generate a standard curve for pH determination, SNARF was dissolved in colorless pH standards and fluorescence ratios were converted to pH. Powders tested in this assay were suspended in the appropriate volume of PFH, which were sonicated for 1 min to aid suspension. AmBisome was suspended by vortexing in PFH. Subsequently, 20 μL of suspension was administered onto the surface of cultured airway epithelia (A=0.33 cm$^2$) at concentrations between 0.5 and 50 μM. In all experiments, ASL pH of compound-treated epithelia was measured and compared to the results from vehicle-treated epithelia. For apical compound administration, cultured airway epithelia were incubated for about 22 hours at 37° C. before measurement of ASL pH.

Preparation of erythrocyte stock suspension. One mL of human whole blood (Na-Heparin preparation; BioIVT, Westbury, NY) was centrifuged at 10,000×g for 2 min at room temperature. The supernatant was removed, and the pellet was resuspended by gentle inversion in 1 mL 0.9% (m/v) saline (erythrocytes will lyse by pipetting and vortexing). The resulting suspension was centrifuged at 10,000 g for 2 min. The supernatant was then removed, and the saline wash repeated twice more. Following the final wash, the supernatant was removed, and the erythrocyte pellet was resuspended in 1 mL resuspension buffer (10 mM Na$_2$HPO$_4$·7H$_2$O, 10 mM NaH$_2$PO$_4$·H$_2$O, 150 mM NaCl, 1 mM MgCl$_2$·6H$_2$O, pH 7.4) to make the erythrocyte stock suspension.

Minimum hemolytic concentration assay (MHC). Compounds to be tested were prepared in a solution of DMSO (D6-99.9%; Cambridge Isotope Laboratories) in a dilution series, with each concentration at 25.63× final concentration. Compound dilution series were diluted 1:25 in resuspension buffer to a total of 100 μl in a 0.2 mL microcentrifuge tube and vortexed to mix the solution. The negative control (0% lysis) contained DMSO only in the resuspension buffer, while the positive control (100% lysis) contained DMSO only in water, as this causes erythrocytes to lyse completely due to osmotic pressure. Erythrocyte suspension at a volume of 2.52 μL was added to each tube (including controls), each tube was mixed by gentle inversion, and incubated statically at 37° C. for 2 hrs. Following incubation, each sample was mixed again by gentle inversion and centrifuged at 3,214×g for 6 min. After centrifugation, 60 μL of the supernatant was removed, added to a 96-well plate, and the absorbance was read at 540 nm. The data were normalized to the negative control and processed as a % total hemolysis relative to the positive control.

Example 1: Compositions of Lipid-Coated AmB (ABCI-001, ABCI-002, ABCI-003, ABCI-004)

The nominal anhydrous compositions of four compositions of lipid-coated AmB (ABCI-001, ABCI-002, ABCI-003, ABCI-004) are presented in Table 4. Also shown are three controls: AmBisome® (i.e., liposomal amphotericin B, L-AmB); the lyophilized AmB/Chol complexes prepared by Burke et al. (US 2019/0083517; US 2020/0352970); and amphotericin B inhalation powder (ABIP), a dry powder composition of AmB developed by Nektar Therapeutics for the treatment of invasive pulmonary aspergillosis (U.S. Pat. Nos. 7,326,691; 8,404,217; US 2012/0128728).

TABLE 4

| | Theoretical Anhydrous Inhaled AmB Compositions | | | | | | | |
|---|---|---|---|---|---|---|---|---|
| Composition | AmB (% w/w) | Chol (% w/w) | HSPC (% w/w) | DSPG (% w/w) | CaCl$_2$ (% w/w) | Chol/AmB (mol/mol) | HSPC/DSPG (w/w) | Chol/PL (w/w) |
| ABCI-001 | 30.0 | 14.6 | 35.8 | 15.9 | 3.70 | 1.16 | 2.3 | 0.29 |
| ABCI-002 | 14.0 | 6.81 | 51.2 | 22.8 | 5.20 | 1.16 | 2.3 | 0.09 |
| ABCI-003 | 14.0 | 2.36 | 70.3 | 7.8 | 5.52 | 0.40 | 9.0 | 0.03 |
| ABCI-004 | 3.4 | 0.57 | 80.72 | 8.97 | 6.34 | 0.40 | 9.0 | 0.006 |
| AmBisome$^a$ (L-AMB) | 3.8 | 3.9 | 16.1 | 6.3 | — | 2.45 | 2.6 | 0.18 |
| AmB/Chol complex | 32.3 | 67.7 | — | — | — | 5.00 | — | — |
| ABIP | 50.0 | 0.0 | 47.0 $^b$ | 0.0 | 3.0 | 0.0 | n.a. | 0.0 |

$^a$ In addition to the lipids and AmB, AmBisome contains 67.8% sucrose, 2.0% disodium succinate hexahydrate, and 0.2% tocopherol
$^b$ ABIP utilizes synthetic DSPC instead of HSPC The AmB/lipid compositions detailed in Table 4 were plotted in a pseudo-ternary phase diagram in FIG. 2. The PL component at the apex of the ternary diagram represents the sum of mass of the various PL components (e.g., HSPC, DSPC, DSPG).

Although commercial L-AMB contains the same lipid components as the ABCI compositions (i.e., HSPC, DSPG, Chol), they are present in different proportions. Further, the drug and lipids are organized differently in L-AMB in comparison to the ABCI compositions. The drug substance in L-AMB is encapsulated in small unilamellar vesicles (liposomes). The composition has a Chol/AmB ratio of 2.5 mol/mol and an HSPC/DSPG ratio of 2.3 (i.e., 7/3 w/w). The lipid particles are lyophilized into a dry powder in the presence of a large percentage of sucrose, which serves as a cryoprotectant to maintain liposome integrity during lyophilization. Administration of 60 mg of reconstituted L-AMB to the apical side of airway epithelial cells through a 1 cm² tracheal window in four CFTR-/-pigs, resulted in an increase in ASL PH of ~0.2 pH units, from pH 6.8 to 7.0 (US 2020/0352970).

The lyophilized AmB:Chol complexes studied by Burke et al. (US 2019/0083517; US 2020/0352970) have an even higher Chol/AmB ratio of 5.0 mol/mol, but contain no added PL. The AmB:Chol complexes are formed by flash nanoprecipitation from a solution of the materials in dimethylsulfoxide/chloroform when rapidly injected into a nonsolvent (water). The resulting suspension is lyophilized to form a dry powder. The AmB:Chol complexes demonstrated significant increases in bicarbonate secretion and in ASL pH (~0.1-0.2 pH units) in CuFi-1 cells.

ABIP is a spray-dried composition comprising wet-milled AmB crystals coated with a 2:1 molar ratio of DSPC to calcium chloride. This composition contains no cholesterol (i.e., Chol/AmB=0 mol/mol). It also contains only saturated phosphatidylcholine (DSPC) with no added DSPG. While ABIP shows improvements in ASL pH in CuFi-1 cells at low doses (2 µM in FC-70), it does not at high doses (50 µM) (Examples 10 and 12). This result is consistent with previous studies with neat AmB and suggests that some amount of Chol is necessary for maintaining ion channel activity across a wide range of AmB concentrations. ABIP compositions comprising highly crystalline drug substance have demonstrated good tolerability in early clinical development.

Compositions are also presented for the three ABCI compositions (ABCI-001, ABCI-002, and ABCI-003), which have been used in nonclinical toxicology studies. These powders have Chol/AmB ratios of from 0.4 to 1.2 mol/mol. Without intending to be bound by theory, the high Chol/AmB ratios utilized in L-AMB and AmB:Chol complexes may be unsuitable for dry powder compositions comprising PL, as the presence of large amounts of Chol may lead to disorder in the packing of the PL acyl chains, resulting in unacceptable increases in interparticle cohesive forces and 'sticky' powders. Both of ABCI-003 and ABCI-004 are encompassed within the shaded triangle of FIG. 2, while ABCI-001 and ABCI-002 are not.

As stated, ABCI-001 and ABCI-002 are outside of the shaded triangle of FIG. 2, as lipids in these compositions are within the so+lo two-phase region. In contrast, ABCI-003 and ABCI-004 are within the so phase. The compositions of the other inhaled AmB compositions (i.e., ABIP, L-AMB (AmBisome), and AmB:Chol complexes) studied to date are well outside of the shaded triangle of FIG. 2.

The DSC thermogram for ABCI-001 (30% w/w AmB, Chol/AmB=1.2 mol/mol) contains a significant proportion of the Chol-rich lo phase (Example 4). For ABCI-002, the drug content was decreased to 14% w/w while holding the Chol/AmB molar ratio constant, which leads to a decrease in the Chol/PL ratio of from 0.29 to 0.09 w/w. Nonetheless a small proportion of the Chol-rich lo phase still remained. Dry powders having the phase-separated lo phase present may exhibit strong interparticle cohesive forces and increased hygroscopicity and deliquescence at high relative humidity (Example 5). These features may negatively impact powder yield during spray drying and may result in relatively large mass median aerodynamic diameters (MMAD~4 µm) (Example 9).

ABCI-003 retains the 14% w/w drug loading in ABCI-002, but with a decreased nominal Chol/AmB ratio of 0.4 mol/mol. Overall, the Chol content is reduced from 14.6% in ABCI-001 to 2.4% in ABCI-003, and the Chol/PL ratio is reduced to 0.03 w/w. At this Chol/PL ratio the lo phase is solubilized in the so phase (Example 4). In ABCI-003, the HSPC/DSPG ratio is also increased from 2.3 w/w to 9.0 w/w, leading to improved solubility of Chol in the PL phase, decreases in NaCl formation, and decreases in powder hygroscopicity (Example 5).

Unlike ABIP, all ABCI compositions containing added Chol exhibit significant improvements in ASL pH at both low and high AmB concentrations (Example 10). Moreover, the presence of DSPG has been shown to bolster the magnitude of the ASL pH improvement observed (Example 12).

Many of the constraints regarding Chol/AmB, Chol/PL, and HSPC/DSPG ratios may be specific to the development of dry powder compositions for inhalation and may not be applicable for liquid-based aerosols such as inhaled L-AMB. Nor may they be directly applicable to compositions that contain no PL.

Example 2: Manufacture of ABCI-001 Via Spray Drying

Feedstock Preparation. The lipids and calcium chloride were first dispersed in hot water with a high-shear mixer (UltraTurrax T-50) to form multilamellar vesicles (MLVs). The aqueous phase must be above the main transition temperature of the lipids ($T_m$) to facilitate MLV formation (T>65° C.). The MLV dispersion was cooled (T<30° C.), and perfluorooctyl bromide (PFOB) was filtered and added using a Watson-Marlow peristaltic pump while mixing to form coarse PFOB-in-water emulsion droplets stabilized by a monolayer of the lipids. The emulsion droplets serve as pore formers to create a porous coating of lipids on the crystalline drug particles. The coarse emulsion was then homogenized in a single, discrete pass under high pressure with a Model M-100 Microfluidizer to form nanoemulsion droplets (diameter~200-500 nm). Next, the drug substance was added under high-shear mixing to the nanoemulsion. The complex dispersion comprising suspended drug and nanoemulsion droplets was passed through the homogenizer for two additional discrete passes. The homogenization process wet mills the AmB particles to a suitable size for pulmonary delivery. On a number basis, most of the wet-milled AmB crystals have a diameter less than 1000 nm. In one embodiment, the final feedstock composition had a solids content of 3.0% w/w, a PFOB content of 20% v/v, and a theoretical batch size of 318 g (9 liters of feedstock) or 424.2 g (12 liters of feedstock).

Production of Dry Powders by Spray Drying. Spray drying was conducted with a pilot-scale spray dryer (Niro Mobile Minor, Copenhagen, Denmark), equipped with a Schlick 970/0 twin-fluid atomizer (0.8 mm i.d.), a Dorr-Clone cyclone, and a lower end geometry comprising a straight tube and Brewer valve. The 1 L Eagle collector attached beneath the Brewer valve was jacketed and maintained at 50° C.

The liquid feed was pumped into the spray dryer with a Watson-Marlow peristaltic pump. The atomizer was operated at a gas flow of 7.0±0.6 scfm and an inlet temperature of 104±5° C. The liquid feed rate was adjusted to maintain a dryer outlet temperature of 55±3° C. The total gas flow was about 140 N m³/h (~85 scfm).

In suspension-based feeds, each atomized droplet (mass median diameter~10 µm) contains dispersed drug crystals and approximately 1000 sub-micron emulsion droplets. During the initial moments of the drying process, the more volatile aqueous phase begins to evaporate. The rapidly receding atomized droplet interface drives enrichment of the slowly diffusing drug and emulsion particles at the interface. This leads to formation of a void space in the center of the drying droplet. As the drying process continues, the less volatile oil phase in the emulsion droplets evaporates, resulting in formation of hollow pores in their place. Overall, the resulting hollow spray-dried composite particles contain drug crystals embedded in an interfacial layer of a porous lipid matrix.

ABCI-002, ABCI-003, and ABCI-004 were manufactured using the same general process, although the compositions of the liquid feeds differed.

Example 3: Wet-Milling of AmB and Impact on Properties of ABCI-002

The physical form of AmB (crystalline vs. amorphous) can have an impact on its wet-milling behavior. For this study two batches of AmB were obtained from North China Pharmaceutical Group Corp. (Hebei, China). The two batches differed in their crystallinity, with batches '202 and '203 having crystallinities of 77 and 96%, respectively (as determined by quantitative XRPD).

Indeed, the decreased crystallinity of batch '202 negatively impacted the wet-milling process, significantly increasing the $X_{50}$ and $X_{90}$ of the wet-milled drug as determined for suspensions of drug by laser diffraction with a Malvern Mastersizer (Table 5).

TABLE 5

Impact of AmB Crystallinity on Primary Particle Size Distribution During Wet-Milling

| AmB Batch | Crystallinity | Process | Primary Particle Size $X_{50}$ (µm) | $X_{90}$ (µm) |
|---|---|---|---|---|
| '202 | 77 | 1 pass (15 kpsi) | 3.01 | 6.93 |
|  |  | 3 passes (15, 15, 20 kpsi) | 2.16 | 5.99 |
| '203 | 96 | 1 pass (15 kpsi) | 1.14 | 2.46 |
|  |  | 3 passes (15, 15, 20 kpsi) | 1.06 | 2.14 |

Batches of ABCI-002 were manufactured on a Niro Mobile Minor with AmB batches '202 (ABCI-002 Batch FP21060) and '203 (ABCI-002 Batch FP21059), using the process described in Example 2. The total solids content and % PFOB in the liquid feedstocks were 2% w/w and 10% v/v, respectively. The liquid feed rate was about 44.5 g/min. The atomizer was operated at a gas flow of 11.5±1.0 N m³/h (7.0 scfm) and an inlet temperature of 104±5° C. This equated to about 44.5 g/min. The total gas flow was about 140 N m³/h (~85 scfm). The target batch size was 40 g.

The physicochemical properties and aerosol performance of the two batches are detailed in Table 6. No significant differences in powder properties and aerosol performance are observed, suggesting that crystallinities as low as 77% remain suitable for preparing ABCI-002 compositions.

TABLE 6

Comparison of the Physicochemical Properties and Aerosol Performance of ABCI-002 Batches Prepared from AmB Batches with Different Crystallinities

| Batch | AmB Crystallinity (%) | Yield (%) | Chol Assay (mg/g) | AmB Assay (mg/g) |
|---|---|---|---|---|
| FP21059 | 96 | 81 | 66 | 162 |
| FP21060 | 77 | 80 | 66 | 152 |

TABLE 6-continued

Comparison of the Physicochemical Properties and Aerosol Performance of ABCI-002 Batches Prepared from AmB Batches with Different Crystallinities

| Batch | Bulk density (g/cm³) | Tapped density (g/cm³) | Carr's Index (%) | Primary particle size | | |
|---|---|---|---|---|---|---|
| | | | | $X_{10}$ (µm) | $X_{50}$ (µm) | $X_{90}$ (µm) |
| FP21059 | 0.078 | 0.130 | 39.7 | 0.63 ± 0.02 | 2.61 ± 0.15 | 5.70 ± 0.27 |
| FP21060 | 0.063 | 0.096 | 34.5 | 0.64 ± 0.03 | 2.60 ± 0.07 | 5.62 ± 0.06 |

| Batch | ED (%) | $FPF_{<5 \mu m}$ (% ND) | MMAD (µm) |
|---|---|---|---|
| FP21059 | 85 | 61 | 2.9 |
| FP21060 | 89 | 63 | 3.1 |

Example 4: Impact of Lipids on Phase Behavior of Lipid-Coated Crystal Compositions of AmB A comparison of the DSC thermograms for ABCI-001, ABCI-002, ABCI-003 and ABIP are presented in FIG. 3.

ABIP has a simple thermogram with a single, sharp, cooperative $T_m$ with an extrapolated onset temperature of 96.2° C. The addition of Chol and DSPG in the ABCI compositions leads to more complex thermograms with a broadening of the transitions and the presence of multiple peaks.

At a Chol/PL ratio of 0.29 w/w (ABCI-001), two phase-separated domains are observed, a Chol-rich lo phase with an onset temperature of 62.5° C., and a broad PL-rich so phase with an onset temperature of 83.9° C. As demonstrated for hydrated DPPC bilayers (FIG. 1), addition of Chol to the so phase leads to increased disorder and eventually phase separation of a coexisting lo phase.

Figure 4:
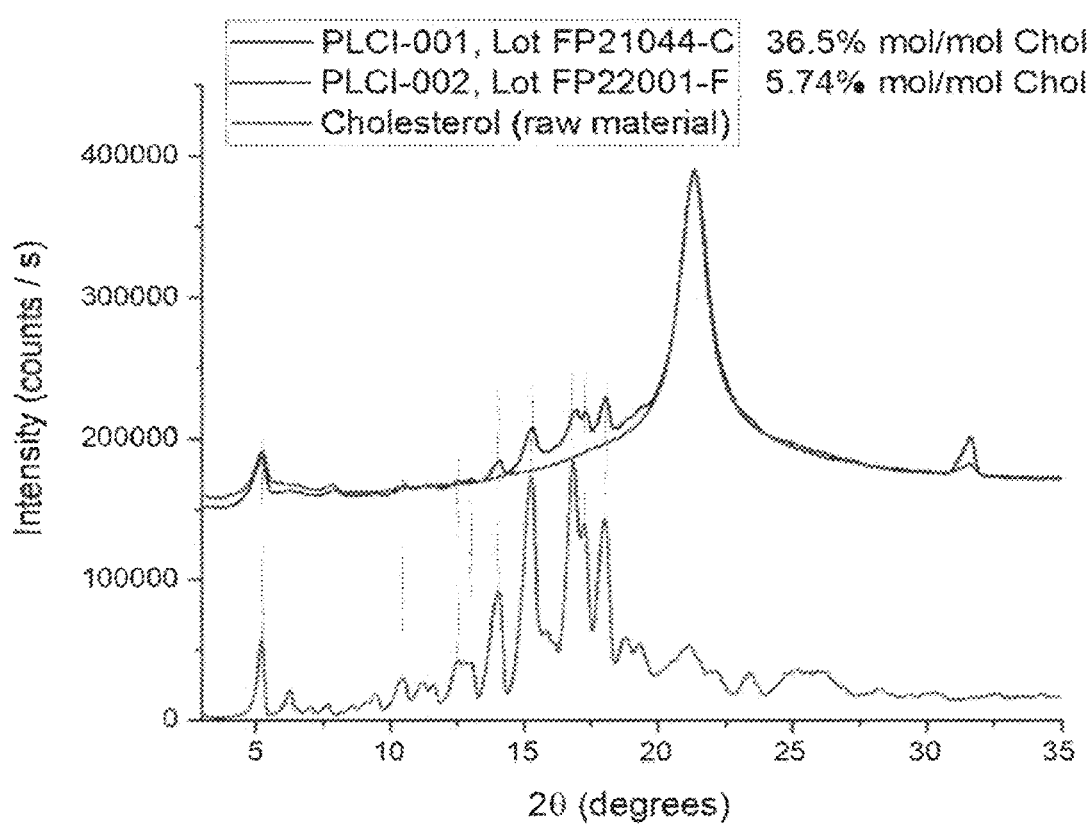
FIG. 4 displays X-Ray Powder Diffraction (XRPD) plots showing evidence of cholesterol crystallites in PLCI-001 and PLCI-002.

The Chol-rich phase transition is very broad and contains overlapping features. The presence of Chol crystallites in the lo phase is supported by X-Ray Powder Diffraction (XRPD) patterns, which show a diffraction peak at about 5.2° 2θ for ABCI variants. Phase separation of cholesterol crystallites is more easily distinguished (i.e., fewer diffraction peaks in the same region and no interference from Amphotericin B peaks) in PLCI-001 (FIG. 4). The PLCI compositions are placebo compositions that do not comprise AmB but comprise the other components of the ABCI compositions.

Figure 5:
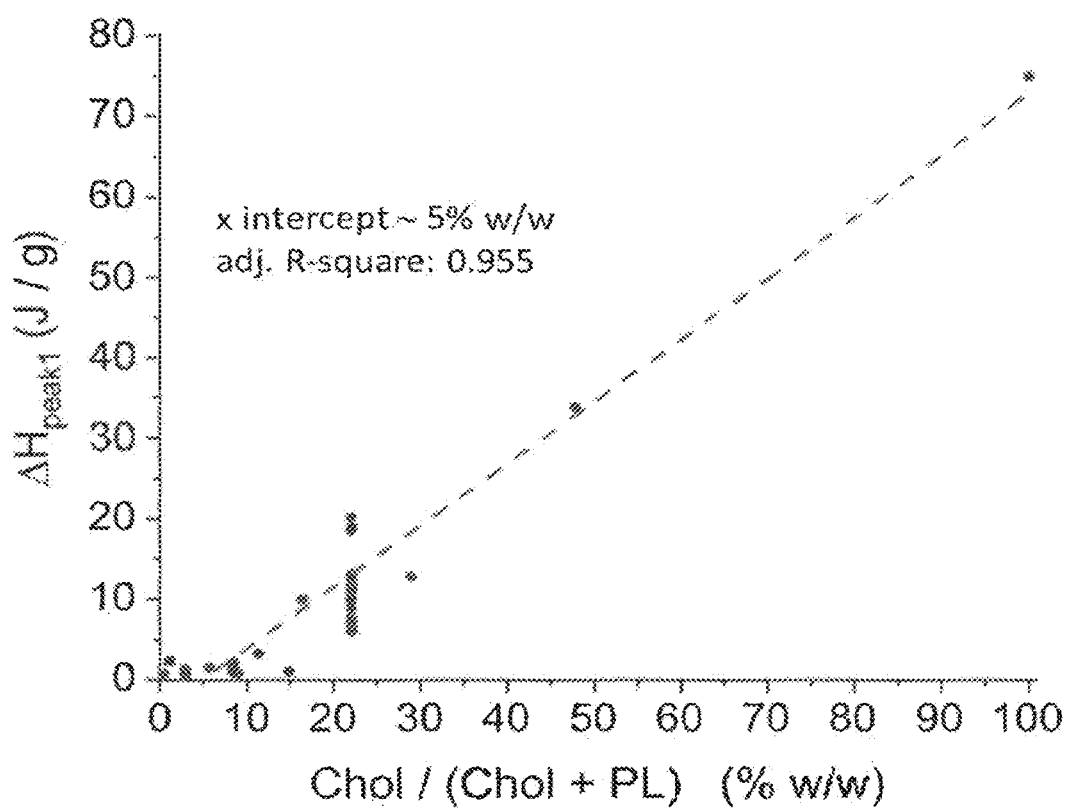
FIG. 5 displays a plot showing that the enthalpy of the Chol-rich phase is proportional to Chol content.

A linear increase in the enthalpy of the Chol-rich phase transition is observed with increases in Chol content in the powder composition (FIG. 5). A linear regression was performed on the data points with Chol/(Chol+PL)>10% w/w. The data extrapolate to the x-axis at a Chol/(Chol+PL) weight ratio of about 4.9% w/w. This is equivalent to a Chol/PL ratio of 0.05 w/w or ~9.4 mol % Chol. Thus, compositions with less than about 9.4 mol % Chol may be expected to have an undetectable low-temperature peak.

In the dehydrated state, the onset of the so-lo two-phase region tends to occur at a much higher Chol concentration (i.e., versus the hydrated state in FIG. 1). Hence, the ordered so phase in ABCI compositions is maintained at a much higher Chol content (~9.4 mol % vs. 6 mol % for the hydrated DPPC bilayer). As well, while the so phase is eliminated in the hydrated DPPC/Chol mixtures above about 20 mol % Chol (FIG. 1), the so-lo two phase region extends beyond 36.5 mol % Chol in dehydrated ABCI-001. Hence, relative to hydrated DPPC-Chol mixtures phase diagram in FIG. 1, the phase diagram for ABCI-001 is shifted upward to higher $T_m$ values, and to the right to higher cholesterol contents.

The high-$T_m$ peak in ABCI-001 is also very broad and comprises multiple overlapping features. The enthalpy of the high-$T_m$ peak tends to increase with increasing PL content and tends to decrease with increasing Chol content, suggesting that this peak below $T_m$ is associated with the so phase.

Binary mixtures of HSPC/DSPG in 20% AmB compositions (no Chol) exhibit similar overlapping features, which is suggestive of coexisting immiscible so phases. The phase separation of PC and PG domains in the presence of calcium ions is consistent with observations in other studies. The onset temperature and enthalpy for the high-$T_m$ peak in ABCI-001 is 83.9° C. and 19.74 J/g, respectively.

Figure 3:
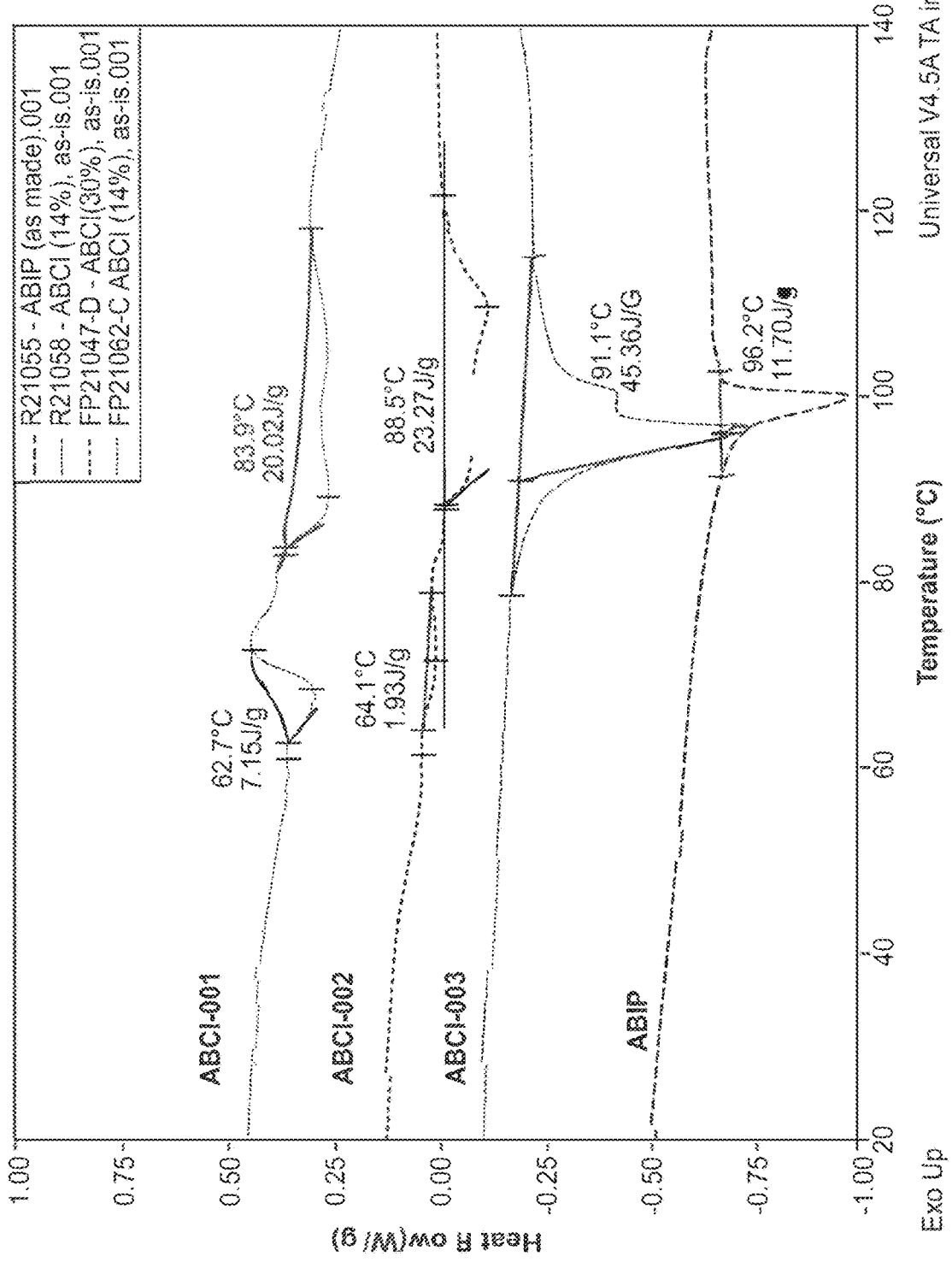
FIG. 3 displays differential scanning calorimetry thermograms of Amphotericin B inhalation powder (ABIP), ABCI-001, ABCI-002, and ABCI-003.

The transition from ABCI-001 to ABCI-002 decreased the drug loading from 30% w/w to 14% w/w, while maintaining a Chol/AmB ratio of 1.2 mol/mol. The decrease in AmB and Chol leads to an increase in PL content, and a decrease in the Chol/PL ratio from 0.28 to 0.092 w/w. While a small amount of the low-$T_m$ peak remains visible in ABCI-002, the $T_m$ increases for the Chol-rich domain from 62.5 to 64.6° C. while ΔH decreases from 7.73 to 1.93 J/g (FIG. 3).

The high-$T_m$ peak remains broad with overlapping features. Relative to ABCI-001, the onset temperature is increased from 83.9 to 88.5° C., suggesting that the acyl chains have increased order as Chol content is decreased.

In ABCI-003, the drug loading remains 14% w/w, but the Chol/AmB ratio is decreased from 1.2 to 0.4 mol/mol. This enables reductions in the Chol/PL ratio relative to ABCI-002 from 0.092 to 0.030 w/w. Enlargement of the low-$T_m$ peak region of the ABCI-003 thermogram (FIG. 3) shows that the Chol-rich peak has been eliminated. The high-$T_m$ peak is also much sharper, with an onset temperature increased by 7.2° C. relative to ABCI-001, to 91.1° C.

For the long-term stability of amorphous solids, it may be beneficial to have a glass transition temperature, $T_g$, that exceeds the storage temperature, $T_s$, by at least 50° C. By analogy, the $T_m$ in PL represents an order-disorder transition. Having a $T_m$ of 91.1° C. for ABCI-003 means that $T_m$ exceeds an accelerated $T_s$ of 40° C. by 50° C.

As discussed previously, the decrease in Chol/PL ratio has a profound effect on powder properties increasing manufacturing yield from 74.5 to 82.4%, reducing Carr's Index from 41.4 to 27.0, and dramatically reducing interparticle cohesive forces as evidenced by a nearly two-fold reduction in MMAD.

A linear decrease in the enthalpy of the lo phase transition is observed with increases in Chol content in the powder composition (FIG. 5). The regression to the points suggests that the x-intercept (i.e., where the enthalpy goes to zero) occurs at a Chol/PL ratio of 0.05 w/w. This ratio is used in defining the shaded region of FIG. 2.

Figure 6:
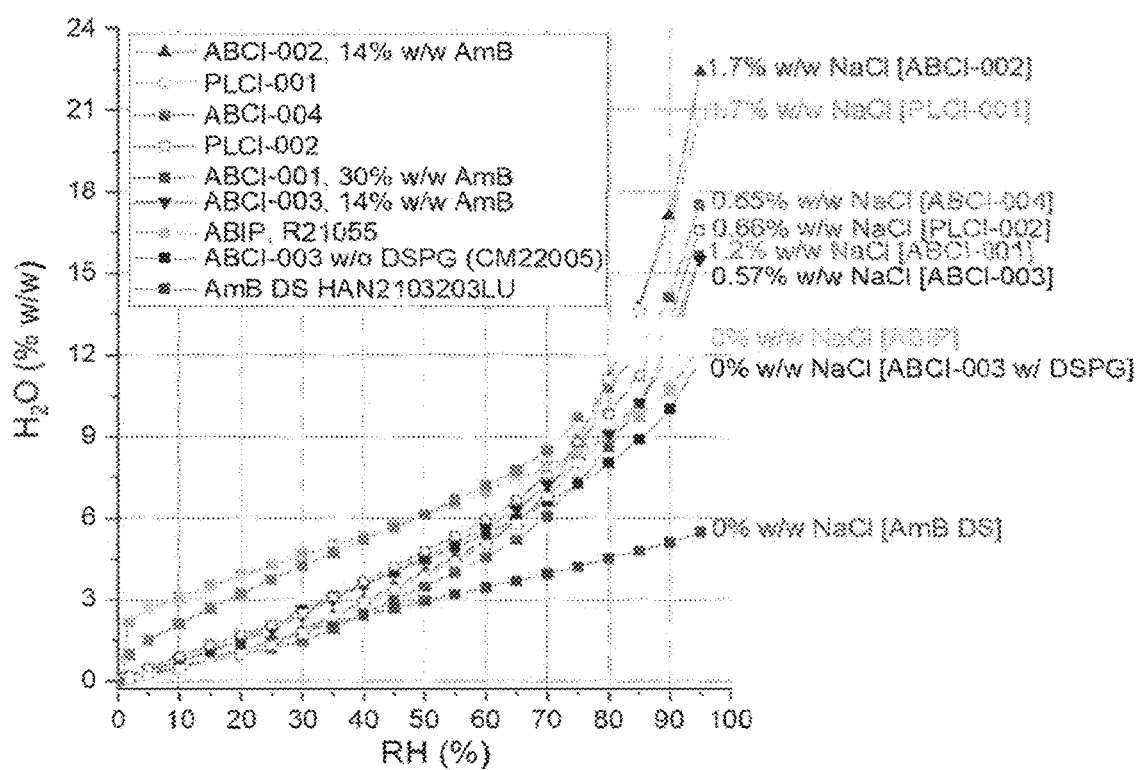
FIG. 6 displays moisture sorption isotherms (25° C.) of various amphotericin B (AmB) and placebo compositions.

Example 5: Impact of Lipid Composition on the Hygroscopicity of AmB Compositions at High Relative Humidity FIG. 6 presents the dynamic vapor sorption characteristics for various compositions. Significant increases in moisture sorption are observed for compositions containing Chol and DSPG relative to ABIP. Without intending to be bound by theory, it is believed that the increases in moisture sorption are due to the presence of NaCl in the composition, which results from the interaction of DSPG and calcium chloride. The divalent calcium ions may bind strongly to anionic DSPG Na, resulting in displacement of the sodium ions which may then interact with the chloride ions from the $CaCl_2$ to form NaCl. At high RH, compositions comprising DSPG/$CaCl_2$) deliquesce, with the magnitude of moisture sorption and deliquescence directly proportional to the amount of NaCl formed.

ABCI-003, where the PL component contains an HSPC/DSPG ratio of 9.0 w/w, exhibits significantly reduced hygroscopicity compared to ABCI-001 and ABCI-002, where the HSPC/DSPG ratio is 2.3 (i.e., 7/3) w/w.

Example 6: Physicochemical Properties of ABCI-001

Spray-dried powders of ABCI-001 were manufactured on a Niro Mobile Minor spray-drier as described in Example 2. The physicochemical properties of the small porous particles (e.g., AmB content, AmB purity, Chol content, primary particle size distribution, bulk density, tapped density, Carr's Index, and water content) are detailed in Table 7.

As is characteristic of powders spray-dried from suspensions of drugs, ABCI-001 powders are enriched in AmB by about 10% of the nominal drug content. The enrichment leads to a decrease in the Chol/AmB molar ratio to 1.0 mol/mol. Despite the enrichment, the AmB and Chol assay values were consistent across the five batches, with relative standard deviations (RSD) of 5% and 1%, respectively. The purity of the incoming AmB drug substance was 96.7%. Purity of AmB was preserved through the manufacturing process with a mean purity for the five ABCI-001 lots of 97.2±0.5%. Moreover, no new degradant peaks were observed in the RP-HPLC chromatograms.

TABLE 7

Physicochemical properties of ABCI-001 bulk powder batches.

| Lot | Yield (%) | Chol Assay (mg/g) | AmB Assay (mg/g) | AmB Purity (%) | Water Content (% w/w) |
|---|---|---|---|---|---|
| FP21040 | 82 | 141 ± 1 | 338 ± 0 | 97.7 ± 0.2 | 3.09 ± 0.14 |
| FP21041 | 74 | 142 ± 1 | 338 ± 1 | 97.7 ± 0.1 | 3.48 ± 0.09 |
| FP21045 | 74 | 144 ± 0 | 334 ± 2 | 96.7 ± 0.2 | 3.44 ± 0.10 |
| FP21046 | 74 | 144 ± 1 | 356 ± 2 | 97.6 ± 0.2 | 2.94 ± 0.08 |
| FP21047 | 68 | 144 ± 1 | 360 ± 5 | 97.2 ± 0.2 | 3.14 ± 0.14 |
| Mean ± SD | 74.5 ± 4.9 | 143 ± 1 | 345 ± 12 | 97.2 ± 0.5 | 3.22 ± 0.23 |
| RSD (%) | 6.6 | 1.0 | 3.4 | 0.5 | 7.2 |

| Lot | Bulk density (g/cm³) | Tapped density (g/cm³) | Carr's Index (%) | $X_{10}$ (μm) | $X_{50}$ (μm) | $X_{90}$ (μm) |
|---|---|---|---|---|---|---|
| FP21040 | 0.066 ± 0.006 | 0.114 ± 0.008 | 42.3 ± 2.2 | 0.63 ± 0.02 | 2.11 ± 0.07 | 5.25 ± 0.28 |
| FP21041 | 0.081 ± 0.007 | 0.143 ± 0.007 | 43.3 ± 4.2 | 0.49 ± 0.05 | 1.90 ± 0.09 | 5.21 ± 0.15 |
| FP21045 | 0.077 ± 0.007 | 0.126 ± 0.009 | 39.3 ± 1.8 | 0.63 ± 0.06 | 1.90 ± 0.04 | 4.51± 0.18 |
| FP21046 | 0.061 ± 0.006 | 0.101 ± 0.007 | 39.3 ± 4.0 | 0.57 ± 0.02 | 1.84 ± 0.11 | 4.13 ± 0.42 |
| FP21047 | 0.069 ± 0.006 | 0.121 ± 0.011 | 43.1 ± 3.7 | 0.61 ± 0.04 | 1.85 ± 0.07 | 4.53 ± 0.33 |
| Mean ± SD | 0.071 ± 0.008 | 0.121 ± 0.015 | 41.4 ± 2.0 | 0.59 ± 0.06 | 1.92 ± 0.11 | 4.73 ± 0.48 |
| RSD (%) | 11.2 | 12.6 | 4.8 | 10.0 | 5.8 | 10.2 |

The primary particle size distribution obtained by laser diffraction is typical of spray-dried particulates from emulsion-based feedstocks with a mean $X_{50}$ value for the five batches of 1.9±0.1 μm, and a mean $X_{90}$ of 4.7±0.5 μm. Within the batch, the RSD for the $X_{50}$ varied between 4.7% and 9.6%, with much of the variability coming from the first collector, before equilibrium was established in the spray dryer.

The low bulk density (0.071±0.008 g/cm$^3$) and tapped density (0.121±0.015 g/cm$^3$) observed are also characteristic of powders manufactured from emulsion-based liquid feedstocks (Table 7). The high compressibility of the fine, low-density particles was demonstrated by the mean Carr's Index value of 41.5±2.0%. This value suggests that the ABCI-001 powders have little to no flowability. The mean residual water content in the powders was 3.2±0.2%.

Example 7: Physicochemical Properties of ABCI-002

The physicochemical properties of ABCI-002 are presented in Table 7. The results are somewhat similar to those presented for ABCI-001. That is not surprising, given that ABCI-002 (14% w/w AmB) represents ABCI-001 (30% w/w AmB) diluted with additional PL, while maintaining a constant Chol/AmB ratio of 1.16 mol/mol.

TABLE 8

Physicochemical properties of ABCI-002 bulk powder batches

| Lot | Yield (%) | Chol Assay (mg/g) | AmB Assay (mg/g) | AmB Purity (%) |
|---|---|---|---|---|
| FP21062 | 79 | 67 | 149 ± 3 | 97.7 ± 0.2 |
| FP21063 | 75 | 67 | 154 ± 1 | 97.7 ± 0.1 |
| FP21064 | 76 | 67 | 158 ± 0 | 96.6 ± 0.1 |
| Mean ± SD | 76.7 ± 1.7 | 67 ± 0 | 154 ± 4 | 97.3 ± 0.3 |
| RSD (%) | 2.2 | 0.0 | 2.6 | 0.3 |

| Lot | Bulk density (g/cm$^3$) | Tapped density (g/cm$^3$) | Carr's Index (%) | Primary particle size | | |
|---|---|---|---|---|---|---|
| | | | | $X_{10}$ (μm) | $X_{50}$ (μm) | $X_{90}$ (μm) |
| FP21062 | 0.069 ± 0.004 | 0.108 ± 0.005 | 36.4 ± 2.1 | 0.57 ± 0.00 | 2.07 ± 0.03 | 5.20 ± 0.10 |
| FP21063 | 0.062 ± 0.005 | 0.097 ± 0.007 | 35.5 ± 3.9 | 0.59 ± 0.01 | 2.21 ± 0.10 | 5.39 ± 0.21 |
| FP21064 | 0.077 ± 0.005 | 0.128 ± 0.007 | 39.7 ± 4.0 | 0.60 ± 0.01 | 2.12 ± 0.03 | 5.58 ± 0.26 |
| Mean ± SD | 0.069 ± 0.006 | 0.111 ± 0.013 | 37.2 ± 1.8 | 0.59 ± 0.01 | 2.13 ± 0.06 | 5.39 ± 0.16 |
| RSD | 8.7% | 11.7% | 4.8% | 1.7% | 2.8% | 1.3% |

Example 8: Physicochemical Properties of ABCI-003

The physicochemical properties of ABCI-003 are detailed in Table 9. Relative to ABCI-001, the drug loading has been reduced from 30% w/w to 14% w/w, and the nominal Chol/AmB ratio has been reduced from 1.2 mol/mol to 0.4 mol/mol.

TABLE 9

Physicochemical properties of ABCI-003 bulk powder batches

| Lot | Yield (%) | Chol Assay (mg/g) | AmB Assay (mg/g) | AmB Purity (%) | Water Content (%) |
|---|---|---|---|---|---|
| FP22002 | 79.3 | 22 ± 0 | 163 ± 1 | 97.9 ± 0.0 | 3.82 ± 0.30 |
| FP22003 | 82.7 | 22 ± 0 | 168 ± 2 | 98.2 ± 0.5 | 3.71 ± 0.17 |
| FP22005 | 85.1 | 22 ± 0 | 168 ± 2 | 99.1 ± 0.0 | 3.72 ± 0.11 |
| Mean ± SD | 82.4 ± 2.9 | 22 ± 0 | 166 ± 3 | 98.4 ± 0.6 | 3.75 ± 0.06 |
| RSD (%) | 3.5 | 0.0 | 1.7 | 0.7 | 1.6 |

| Lot | Bulk density (g/cm$^3$) | Tapped density (g/cm$^3$) | Carr's Index (%) | Primary particle size | | |
|---|---|---|---|---|---|---|
| | | | | $X_{10}$ (μm) | $X_{50}$ (μm) | $X_{90}$ (μm) |
| FP22002 | 0.071 ± 0.004 | 0.098 ± 0.003 | 28.0 ± 2.5 | 0.99 ± 0.21 | 2.73 ± 0.11 | 5.97 ± 0.20 |
| FP22003 | 0.078 ± 0.005 | 0.110 ± 0.010 | 28.8 ± 4.5 | 1.02 ± 0.20 | 2.70 ± 0.14 | 5.99 ± 0.36 |
| FP20005 | 0.069 ± 0.004 | 0.091 ± 0.006 | 24.2 ± 2.5 | 0.92 ± 0.01 | 3.11 ± 0.05 | 6.91 ± 0.15 |
| Mean ± SD | 0.073 ± 0.004 | 0.100 ± 0.008 | 27.0 ± 2.0 | 0.98 ± 0.05 | 2.85 ± 0.23 | 6.29 ± 0.54 |
| RSD (%) | 5.5 | 8.0 | 7.4 | 5.3 | 8.0 | 8.5 |

Example 9: Comparison of the Three ABCI Compositions

A comparison of the physicochemical properties and aerosol performance of the three ABCI compositions is presented in Table 10.

TABLE 10

Comparison of the Physicochemical Properties and Aerosol Performance of ABCI-001, ABCI-002, and ABCI-003

| Composition | Yield (%) | Chol Assay (mg/g) | AmB Assay (mg/g) | Chol/AmB (mol/mol) | AmB Purity (%) |
|---|---|---|---|---|---|
| ABCI-001 | 74.5 ± 4.9 | 143 ± 1 | 345 ± 12 | 1.0 | 97.2 ± 0.5 |
| ABCI-002 | 76.7 ± 1.7 | 67 ± 0 | 154 ± 4 | 1.0 | 97.3 ± 0.3 |
| ABCI-003 | 82.4 ± 2.9 | 22 ± 0 | 166 ± 3 | 0.32 | 98.7 ± 0.6 |

| Composition | Bulk density (g/cm$^3$) | Tapped density (g/cm$^3$) | Carr's Index (%) | Primary particle size | | |
|---|---|---|---|---|---|---|
| | | | | $X_{10}$ (μm) | $X_{50}$ (μm) | $X_{90}$ (μm) |
| ABCI-001 | 0.071 ± 0.008 | 0.121 ± 0.015 | 41.4 ± 2.0 | 0.59 ± 0.06 | 1.92 ± 0.11 | 4.73 ± 0.48 |
| ABCI-002 | 0.069 ± 0.006 | 0.111 ± 0.013 | 37.2 ± 1.8 | 0.59 ± 0.01 | 2.13 ± 0.06 | 5.39 ± 0.16 |
| ABCI-003 | 0.073 ± 0.004 | 0.100 ± 0.008 | 27.0 ± 2.0 | 0.98 ± 0.05 | 2.85 ± 0.23 | 6.29 ± 0.54 |

| Composition | ED (%) | Coarse Fraction [T-S2] (%) | Airways Fraction [S3-S5] (%) | Extrafine Fraction [S6-F] (%) | FPF$_{<5\ \mu m}$ (% ND) | FPF$_{<5\ \mu m}$ (% ED) | MMAD (μm) |
|---|---|---|---|---|---|---|---|
| ABCI-001 | 89 | 36.0 | 49.3 | 3.4 | 50 | 56 | 3.9 |
| ABCI-002 | 92 | 21.0 | 60.3 | 10.5 | 70 | 76 | 2.6 |
| ABCI-003 (R21058) | 88 | 6.1 | 71.8 | 10.6 | 81 | 92 | 2.1 |

There are several apparent trends as the PL/Chol increases from 3.5 to 10.9 to 33.1 w/w (ABCI-001 to ABCI-003). First, there is an increase in yield from 74.5 to 82.4% (+10.6%). Second, there is a decrease in Carr's Index from 41.4 to 27.0, indicative of marked improvements in powder flowability.

There are also significant changes in aerosol performance. This may reflect significant reductions in interparticle cohesive forces and increases in powder dispersibility as the Chol content decreases. The percentage of drug in the coarse fraction decreases from 36.0% to 6.1%, while the percentage in the airways fraction increases from 49.3% to 71.8%. The FPF$_{<5\ \mu m}$ increases from 56% to 92% of the ED, while the MMAD decreases from 3.9 μm to 2.1 μm. The large decrease in MMAD may also decrease deposition in the nose of rodents during nose-only aerosol delivery.

Example 10: Improvements in ASL pH for Various Compositions of AmB Following Apical Administration to Cultured Airway Epithelial Cells Cell-based assays were used to investigate the potency of various lipid-coated crystal compositions of AmB. The ASL pH observed for normal lung epithelial cells (NuLi) is about 7.6. In contrast, the ASL pH observed in CuFi-1 cells (ΔF508/ΔF508 CF mutation) is about 6.85. The decrease in ASL pH has a profound impact on host defense in the CF lung. ASL pH values greater than 7.0 lead to improved effectiveness of defensins, peptides with antimicrobial activity in the lungs that are critical in host defense. Hence, measurement of ASL pH is a useful proxy for assessing the effectiveness of different inhaled AmB compositions.

Table 11 compares the improvements in ASL pH observed for various AmB compositions with immortalized and primary cultured airway epithelial cells. The ASL pH observed for a normal immortalized airway epithelial cell line (NuLi) developed at the University of Iowa is about pH 7.5. Two immortalized CF airway epithelial cell lines were studied: CuFi-1 with a homozygous ΔF508/ΔF508 mutation and CuFi-4 cells with a heterozygous G551D/ΔF508 mutation. The measured ASL pH in these cells varied between about pH 6.7 and pH 7.0 across various studies. Primary cell cultures of airway epithelial cells derived from individuals with CF, including those with nonsense mutations, were also studied. ASL pH measured in primary airway epithelial cells derived from control subjects without CF had a pH of about 6.9 (Shah et al. *Airway acidification initiates host defense abnormalities in cystic fibrosis mice. Science* 2016, 351:503-507).

Figure 7A:
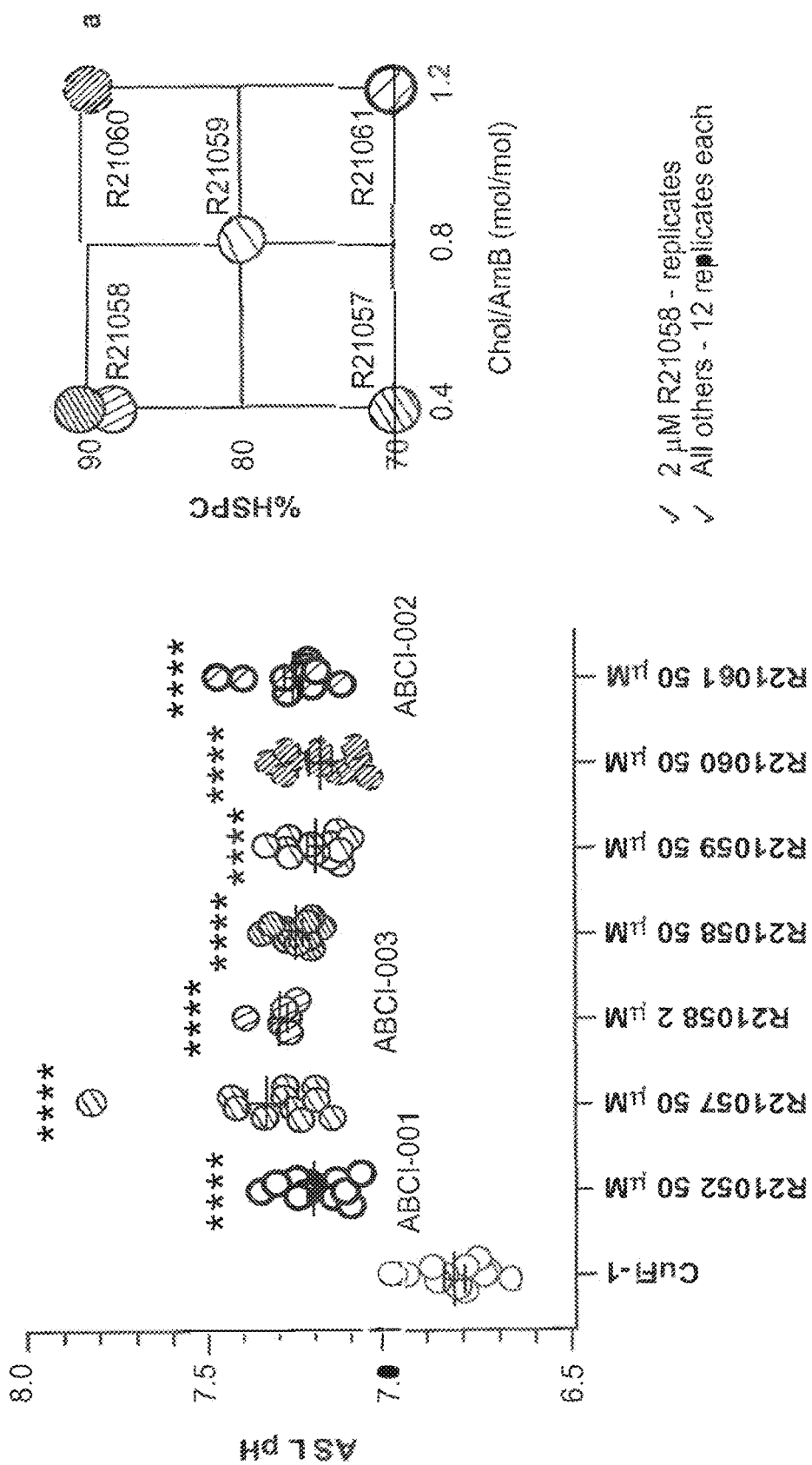
FIG. 7A displays a plot showing increases in airway surface liquid (ASL) pH in CuFi-1 cells for various compositions comprising Chol/AmB ratios between 0.4 and 1.2 mol/mol and HSPC between 70% and 90% w/w of PL.
Figures 7B, 7C:
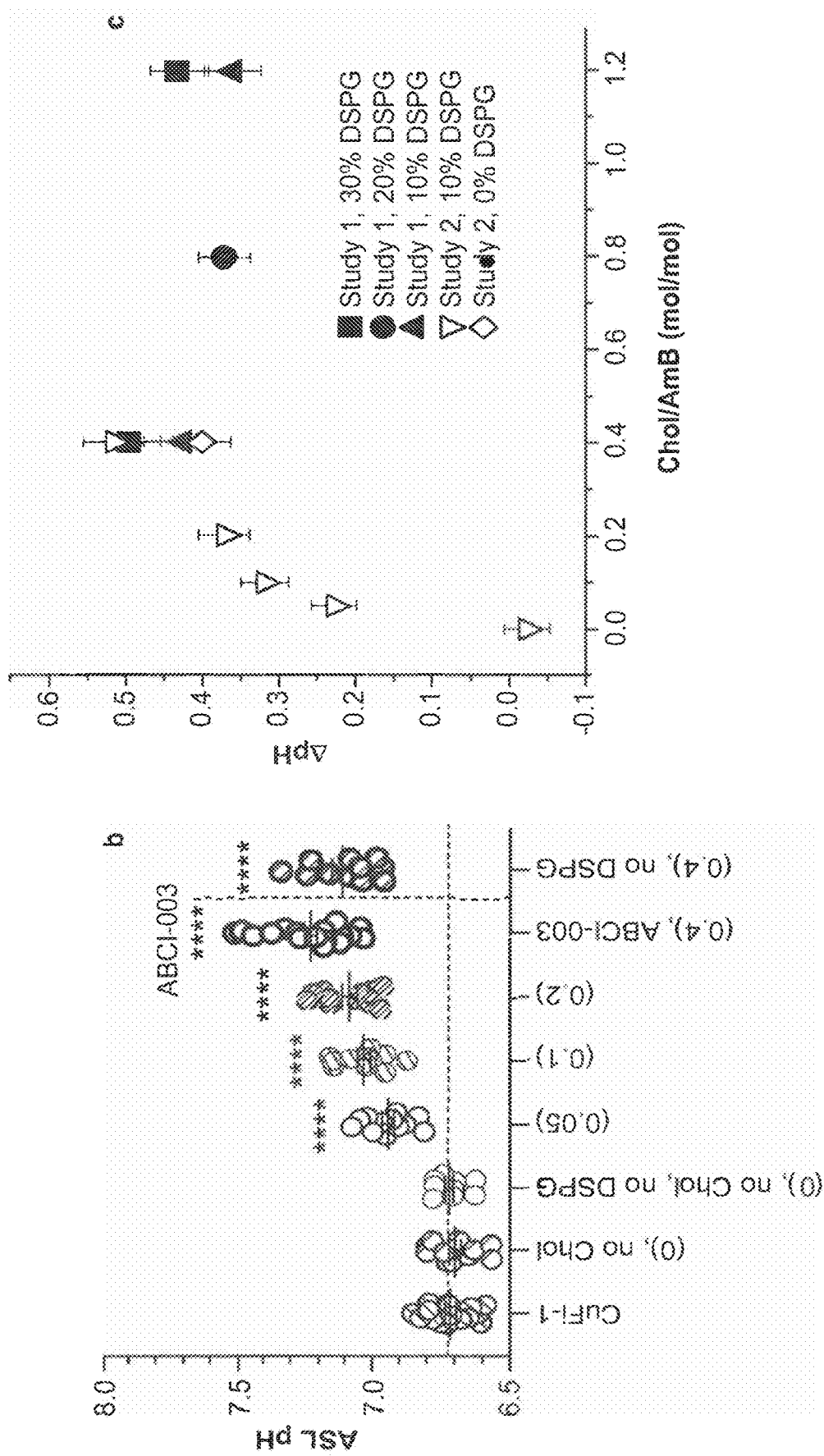
FIG. 7B displays a plot showing increases in ASL pH in CuFi-1 cells for various compositions comprising Chol/AmB ratios between 0 and 0.4 mol/mol and compositions without Chol or DSPG.
FIG. 7C displays a plot showing the impact on improvements in ASL pH in CuFi-1 cells of variations in the ratio of Chol/AmB.
Figure 8:
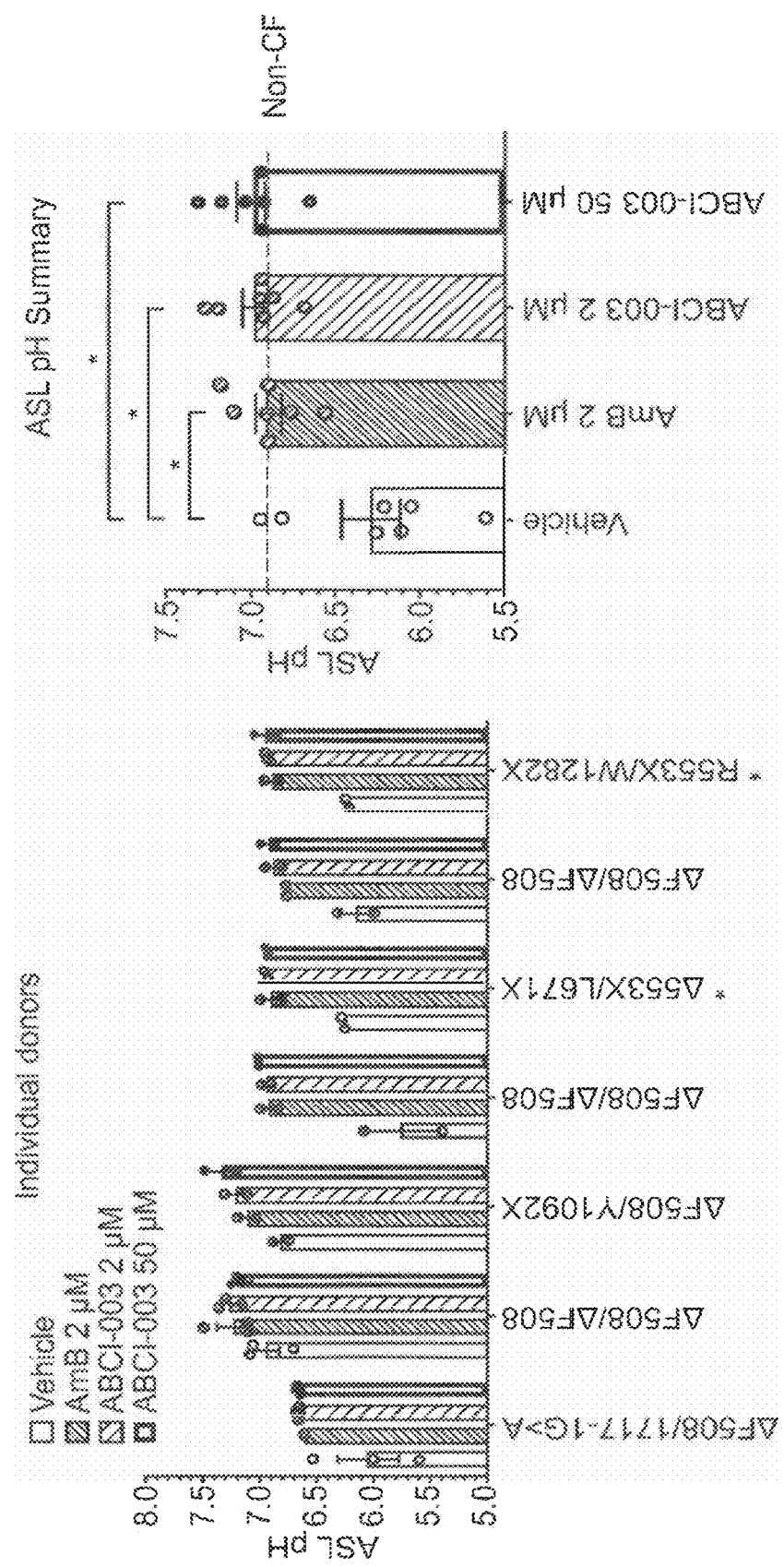
FIG. 8 displays a plot showing increases in ASL pH following administration of ABCI-003 to primary cultured airway epithelial cells from individuals with CF, including those with nonsense mutations.

Findings from these studies include: AmB compositions with no added Chol (e.g., neat AmB, ABIP) are effective at a 2 μM concentration in the perfluorohexane vehicle, but not at a 50 μM AmB concentration (FIG. 7b); AmB/Chol complexes show improvements of ~0.1 pH units versus vehicle controls at 2 μM and 50 μM AmB concentrations (Table 11); following apical administration of 2 μM AmB to primary cultured airway epithelial cells, from subjects with CF, improvements in ASL pH of 0.1 to 0.2 pH units are observed, independent of the CFTR genotype (Table 11); L-AMB, which contains added PL (HSPC/DSPG=7/3 w/w), shows improvements in ASL pH by ~0.4 pH units that is maintained at 2 μM and 50 μM AmB concentrations (Table 11); ivacaftor increases ASL pH by about 0.2 pH units in CuFi-4 cells, but as expected has a minimal increase in ASL pH in CuFi-1 cells with homozygous ΔF508 mutations (Table 11); Trikafta leads to similar increases in ASL pH as ABCI-003 in CuFi-1 cells (Table 11); ABCI compositions comprising Chol/AmB ratios ≥0.4 mol/mol exhibit maximal improvements in ASL pH in CuFi-1 cells of about 0.4 to 0.5 pH units at both 2 μM and 50 μM AmB concentrations, but the improvements in ASL pH decrease in magnitude for Chol/AmB ratios less than 0.4 mol/mol (FIG. 7a; FIG. 7c); improvements ≥0.2 pH units are observed for Chol/AmB ratios as low as 0.05 mol/mol (FIG. 7b; FIG. 7c); the improvements in ASL pH are enhanced by the presence of DSPG in the composition versus HSPC alone (FIG. 7b; FIG. 7c); no significant differences in ASL pH were observed following administration of ABCI-001, ABCI-002, and ABCI-003 (FIG. 7a); the mean improvements in ASL pH in primary cultured airway epithelia from individuals with CF was ~0.7 pH units, from pH 6.3 to pH 7.0; and six out of seven primary cultured airway epithelia samples from individuals with CF achieved a pH of 6.9 or greater (i.e., full restoration of ASL pH relative to healthy volunteers), including two cell cultures derived from individuals with nonsense mutations (FIG. 8). Based on these results the optimal Chol/AmB ratio for ABCI compositions may be between 0.4 and 1.2 mol/mol (FIG. 2).

TABLE 11

Improvements in ASL pH in CuFi-1, CuFi-4, and Primary Epithelial Cells from CF Patients Following Administration of AmB Compositions

| Batch | Description | Cells | [AmB] (μM) | pH | ΔpH | Ref. |
|---|---|---|---|---|---|---|
| | Vehicle Control | NuLi | — | 7.51 | n.a. | [1] |
| | Vehicle Control | CuFi-1 | — | 6.88 | n.a. | [1] |
| | AmB | CuFi-1 | 2 | 7.06 | +0.18 | [1] |
| | AmB | CuFi-1 | 50 | 6.80 | +0.02 | [1] |
| | Vehicle Control | CuFi-1 | — | 6.75 | n.a. | [1] |
| | AmB:Chol (1:5) complex | CuFi-1 | 2 | 6.84 | +0.09 | [1] |
| | AmB:Chol (1:5) complex | CuFi-1 | 50 | 6.86 | +0.11 | [1] |
| | L-AMB | CuFi-1 | 2 | 7.18 | +0.43 | [1] |
| | L-AMB | CuFi-1 | 50 | 7.15 | +0.40 | [1] |
| | Ivacaftor | CuFi-1 | 2 | 6.82 | +0.07 | [1] |
| | Vehicle Control | CuFi-4 | — | 6.75 | n.a. | [1] |
| | Ivacaftor | CuFi-4 | 2 | 6.92 | +0.17 | [1] |
| | AmB:Chol (1:5) complex | CuFi-4 | 2 | 6.98 | +0.23 | [1] |
| | Vehicle Control | Primary human CF | — | 6.76 | n.a. | [1] |
| | AmB | Primary human CF | 2 | 6.97 | +0.21 | [1] |
| | Vehicle Control | CuFi-1 | — | 6.95 | n.a. | [2] |
| R20047 | ABIP | CuFi-1 | 50 | 7.01 | +0.06 | [2] |
| FP22001 | PLCI-002 (matching placebo for ABCI-003) | CuFi-1 | 50 | 6.85 | −0.10 | [2] |
| FP20002 | ABCI-003 | CuFi-1 | 50 | 7.26 | +0.31 | [2] |
| | Vehicle Control | CuFi-1 | — | 6.82 | n.a. | [2] |
| R21058 | ABCI-003 | CuFi-1 | 2 | 7.29 | +0.47 | [2] |
| R21058 | ABCI-003 | CuFi-1 | 50 | 7.25 | +0.42 | [2] |
| R21052 | ABCI-001 | CuFi-1 | 50 | 7.19 | +0.37 | [2] |
| R21061 | ABCI-002 | CuFi-1 | 50 | 7.25 | +0.43 | [2] |
| R21057 | ABCI (Chol/AmB = 0.4, % HSPC = 70%) | CuFi-1 | 50 | 7.32 | +0.50 | [2] |
| | Vehicle Control | CuFi-1 | — | 6.72 | n.a. | [2] |
| CM22001 | ABCI (Chol/AmB = 0.2, DSPG = 10%) | CuFi-1 | 50 | 7.09 | +0.37 | [2] |
| CM22002 | ABCI (Chol/AmB = 0.1, DSPG = 10%) | CuFi-1 | 50 | 7.04 | +0.32 | [2] |
| CM22003 | ABCI (Chol/AmB = 0.05, DSPG = 10%) | CuFi-1 | 50 | 6.95 | +0.23 | [2] |
| CM22004 | ABCI (Chol/AmB = 0, DSPG = 10%) | CuFi-1 | 50 | 6.70 | −0.02 | [2] |
| CM22005 | ABCI (Chol/AmB = 0.4, DSPG = 0%) | CuFi-1 | 50 | 7.12 | +0.40 | [2] |
| CM22006 | ABCI (Chol/AmB = 0, DSPG = 0%) | CuFi-1 | 50 | 6.71 | −0.01 | [2] |
| | Vehicle Control | CuFi-1 | — | 6.92 | n.a. | [2] |
| | Trikafta (ETI) | CuFi-1 | E (1) T (1) I (0.33) | 7.38 | +0.46 | [2] |
| FP22005 | ABCI-003 | CuFi-1 | 2 | 7.38 | +0.46 | [2] |
| | Vehicle Control | Primary human CF | — | 6.30 | n.a. | [2] |
| | Vehicle Control | Primary human HV | — | 6.90 | +0.60 | [3] |
| FP22005 | ABCI-003 | Primary human CF | 2 | 6.98 | +0.68 | [2] |
| FP22005 | ABCI-003 | Primary human CF | 50 | 7.00 | +0.70 | [2] |

[1] US 2019/0083517; US 2020/0352970;
[2] Present disclosure;
[3] Shah, 2016

Example 11: Dose Response Observed with ABCI-001

Figure 9:
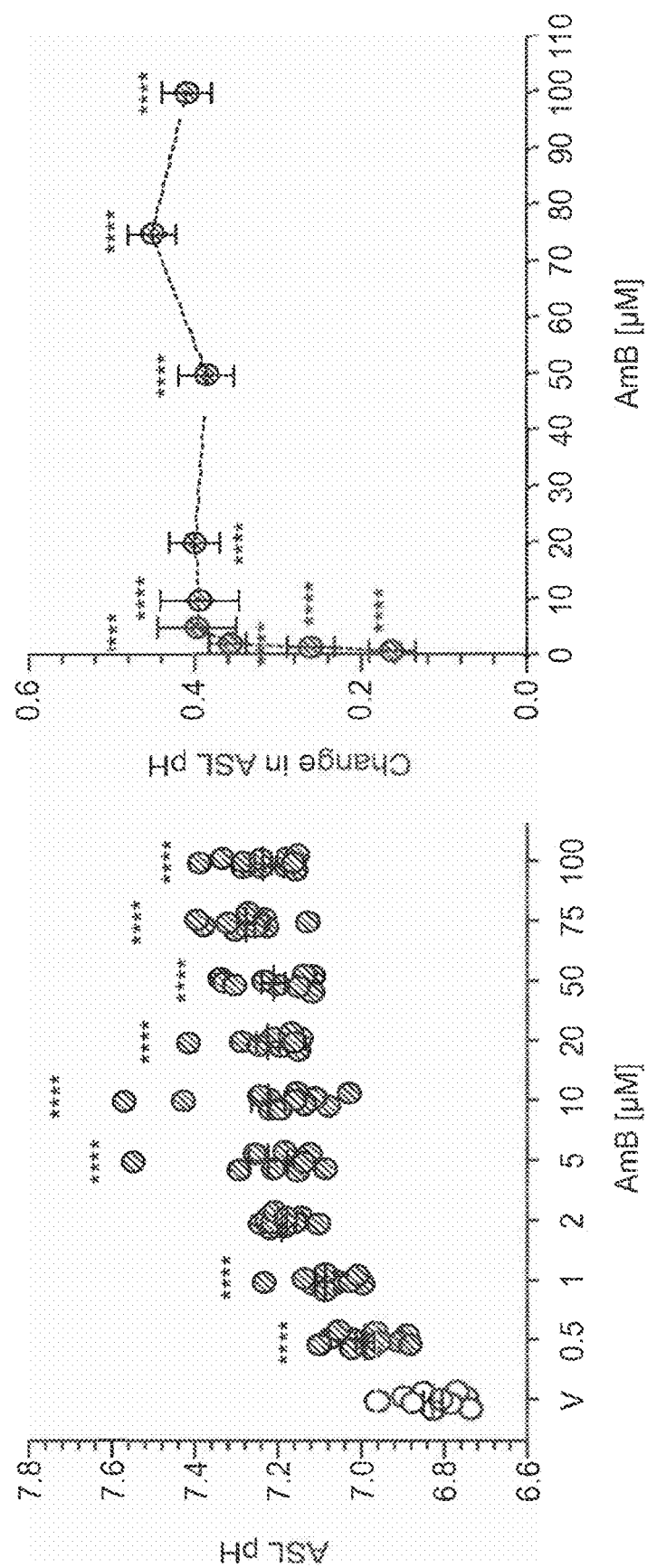
FIG. 9 displays a plot showing increases in ASL pH in CuFi-1 cells for ABCI-003 as a function of increases in AmB concentration suspended in perfluorohexane (FC-72) vehicle.

The dose dependence of improvements in ASL pH for ABCI-003 is presented in FIG. 9. Concentrations on the abscissa represent the concentration of AmB suspended in a perfluorohexane vehicle for application to CuFi-1 cells, not the true ASL concentration. The $EC_{50}$ and $EC_{90}$ based on the perfluorohexane concentrations were about 0.5 µM and 2.0 M, respectively.

Example 12: ABCI Compositions Comprising Various Chol/AmB Ratios and DSPG Contents Burke et al. demonstrated that AmB:Chol complexes with a Chol/AmB ratio of 5.0 mol/mol maintained improvements in ASL pH in CuFi-1 cells over suspension concentrations ranging from 2 µM to 50 µM in perfluorohexane (US 2019/0083517; US 2020/0352970; both are incorporated by reference).

Similar results have been observed with lipid-coated AmB compositions of the present disclosure provided they contain added Chol. At a 50 µM AmB concentration, ABIP (which contains no added Chol), showed no improvement in ASL pH.

In contrast, ABCI compositions with a theoretical Chol/AmB ratio of ~1.2 (e.g., ABCI-001, ABCI-002) exhibit strong improvements in ASL pH at 50 µM (e.g., 0.35 to 0.45 pH units).

Previous studies have suggested that the benefits achieved with added Chol may be lost for Chol/AmB ratios below 1.0 mol/mol (US 2019/0083517; US 2020/0352970). It has been surprisingly discovered that improvements in ASL pH can be maintained at 50 µM AmB concentrations for ABCI compositions with a theoretical Chol/AmB ratio of 0.4 mol/mol (nominal measured ratio in powder=0.32 mol/mol).

Hence, while Chol may be necessary to maintain effective improvements in ASL pH across a wide range of delivered doses, Chol/AmB ratios as low as 0.4 mol/mol remain effective. The efficacy observed for the lower Chol/AmB ratios was established in a small design of experiments (DoE) study (FIG. 7A). The study also explored the impact of lowering the percentage of DSPG in the composition. The theoretical anhydrous compositions of the spray-dried powders manufactured on a Buchi B-191 spray dryer, are detailed in Table 12. The physicochemical properties of the ABCI variants are presented in Table 13. The aerosol performance of selected ABCI variants is presented in Table 14.

TABLE 12

Nominal anhydrous compositions of ABCI variants comprising lower Chol/AmB ratios and decreased DSPG content

| Batch number | AmB (% w/w) | Chol (% w/w) | HSPC (% w/w) | $CaCl_2$[b] (% w/w) | DSPG (% w/w) | Chol/AmB (mol/mol) | HSPC/DSPG (w/w) | PL/Chol (w/w) |
|---|---|---|---|---|---|---|---|---|
| R21057 | 14.0 | 2.34 | 54.1 | 5.51 | 24.1 | 0.40 | 2.2 | 32.6 |
| R21058 (ABCI-003) | 14.0 | 2.36 | 70.3 | 5.52 | 7.8 | 0.40 | 9.0 | 33.1 |
| R21059 | 14.0 | 4.58 | 60.5 | 5.37 | 15.5 | 0.78 | 3.9 | 16.6 |
| R21060 | 14.0 | 6.81 | 66.5 | 5.22 | 7.4 | 1.16 | 9.0 | 10.9 |
| R21061 (ABCI-002) | 14.0 | 6.81 | 51.2 | 5.20 | 22.8 | 1.16 | 2.3 | 10.9 |
| R21062 (ABCI-002) | 14.0[a] | 6.81 | 51.2 | 5.22 | 22.8 | 1.16 | 2.3 | 10.9 |
| ABCI-001 | 30.0 | 14.6 | 35.8 | 3.70 | 15.9 | 1.16 | 2.3 | 3.5 |

[a]Batch R21062 contains amorphous AmB particles
[b]The ratio of PL/$CaCl_2$ is 2.0 mol/mol

TABLE 13

Physicochemical properties of 14% w/w ABCI variants containing various Chol/AmB ratios and percentages of DSPG

| Batch | Bulk density (g/cm$^3$) | Tapped density (g/cm$^3$) | Carr's Index (%) | Primary Particle Size Distribution $X_{10}$ (μm) | $X_{50}$ (μm) | $X_{90}$ (μm) |
|---|---|---|---|---|---|---|
| R21057 | 0.085 | 0.125 | 32.0 | 0.64 ± 0.01 | 1.86 ± 0.01 | 3.71 ± 0.02 |
| R21058 (ABCI-003) | 0.060 | 0.081 | 26.0 | 0.77 ± 0.02 | 2.01 ± 0.02 | 3.77 ± 0.07 |
| R21059 | 0.059 | 0.089 | 33.3 | 0.76 ± 0.01 | 2.03 ± 0.03 | 4.02 ± 0.17 |
| R21060 | 0.049 | 0.070 | 29.9 | 0.79 ± 0.01 | 2.16 ± 0.02 | 4.10 ± 0.08 |
| R21061 | 0.048 | 0.065 | 26.1 | 0.71 ± 0.00 | 2.00 ± 0.01 | 3.91 ± 0.01 |
| R21062 | 0.051 | 0.078 | 34.3 | 0.70 ± 0.03 | 2.07 ± 0.02 | 4.06 ± 0.09 |
| ABCI-002 | 0.069 ± 0.006 | 0.111 ± 0.013 | 37.2 ± 1.8 | 0.59 ± 0.01 | 2.13 ± 0.06 | 5.39 ± 0.16 |
| ABCI-001 | 0.071 ± 0.008 | 0.121 ± 0.015 | 41.4 ± 2.0 | 0.59 ± 0.06 | 1.92 ± 0.11 | 4.73 ± 0.48 |

TABLE 13-continued

Physicochemical properties of 14% w/w ABCI variants containing various Chol/AmB ratios and percentages of DSPG

| | Theoretical | | | Nominal | | | |
|---|---|---|---|---|---|---|---|
| Batch | Chol/AmB (mol/mol) | HSPC/DSPG (mol/mol) | PC/Chol (w/w) | Yield (%) | Chol Assay (mg/g) | AmB Assay (mg/g) | Chol/AmB (mol/mol) |
| R21057 | 0.40 | 2.2 | 32.6 | 70 | 22 | 163 | 0.33 |
| R21058 (ABCI-003) | 0.40 | 9.0 | 33.1 | 67 | 23 | 167 | 0.33 |
| R21059 | 0.78 | 3.9 | 16.6 | 69 | 43 | 163 | 0.64 |
| R21060 | 1.16 | 9.0 | 10.9 | 71 | 65 | 151 | 1.04 |
| R21061 | 1.16 | 2.3 | 10.9 | 64 | 65 | 161 | 0.98 |
| R21062 | 1.16 | 2.3 | 10.9 | 70 | 66 | 83 | 1.93 |
| ABCI-002 | 1.16 | 2.3 | 10.9 | 77 | 67 | 154 | 1.06 |
| ABCI-001 | 1.16 | 2.3 | 3.5 | 75 | 143 | 345 | 1.01 |

TABLE 14

Metrics regarding the aerosol performance of ABCI variants

| Batch | Chol/AmB (mol/mol) | HSPC/DSPG (w/w) | ED (%) | Coarse Fraction [T-S2] (%) | Airways Fraction [S3-S5] (%) | Extrafine Fraction [S6-F] (%) | $FPF_{<5\,\mu m}$ (% ND) | MMAD (μm) |
|---|---|---|---|---|---|---|---|---|
| R21058 (ABCI-003) | 0.40 | 9.0 | 88 | 6.1 | 71.8 | 10.6 | 81 | 2.1 |
| R21059 | 0.78 | 3.9 | 89 | 11.8 | 64.2 | 13.0 | 75 | 2.1 |
| R21061 (ABCI-002) | 1.16 | 2.3 | 86 | 10.3 | 70.6 | 5.2 | 73 | 2.7 |
| FP21062 (ABCI-002) | 1.16 | 2.3 | 92 | 21.0 | 60.3 | 10.5 | 70 | 2.6 |
| FP21040 (ABCI-001) | 1.16 | 2.3 | 89 | 36.0 | 49.3 | 3.4 | 50 | 3.9 |

Interparticle cohesive forces tend to decrease as the Chol and DSPG content in the powders decrease. This is reflected in a dramatic decrease in the coarse particle fraction, as denoted by deposition on the USP throat and stage 1 and stage 2 in the impactor. The coarse particle fraction decreases from 35.9% for ABCI-001 to 21.1-21.8% for ABCI-002, to just 6.2% for Batch R21058 (ABCI-003). This is further reflected by a shift in the pattern of stage deposition. The APSD for ABCI-001 is centered around stages 2 and 3, with an MMAD of 3.9 μm. ABCI-002 exhibited primary deposition on stages 3 and 4, with a shift in the MMAD down to 2.6 to 2.7 μm. Finally, for Batch R21058, the Chol/AmB ratio was decreased to 0.4 mol/mol, and the HSPC content in the PL was increased to 90% w/w, the primary deposition now peaks on stages 4 and 5 of the impactor, with an MMAD of 2.1 μm.

When the data for Batch R21058 are expressed as a percentage of the emitted dose, the $FPF_{<5\,\mu m}$ is 93%. Given that 98% of the emitted dose of Batch R21058 is deposited on the impactor stages (i.e., only 2% on the induction port or USP throat), the impaction parameter (i.e., da Q) for the entire monomodal particle size distribution may be calculated. The value of 195 μm² L/min can be used to predict particle deposition in the upper respiratory tract (URT), as well as the total lung dose (TLD). The impaction parameter results suggest that about 90% of the emitted dose is expected to deposit within the lungs, and only about 10% in the URT. A large percentage of the TLD may deposit in the large and small airways within the lungs, as evidenced by the large percentage of the dose deposited in the airways fraction on stages 3 to 5, and the comparatively low percentage of particles in the extrafine fraction on stages 6 to filter.

The significant decrease in MMAD may not only reduce URT deposition in humans, but also decrease nasopharyngeal deposition in rats in nonclinical studies. The improvements in ASL pH achieved with the various ABCI variants are plotted in FIG. 7. The data were collected at a 50 μM AmB concentration in the fluorocarbon vehicle after 22 hours of incubation (N=12 replicates per composition). Data were also collected for Batch R21058 at 2 μM (N=6 replicates). The ASL pH for the ABCI variants with the CuFi-1 cells was between about 7.25 and 7.35 (ΔpH~0.4 to 0.5). Hence, all batches exhibited significant increases in ASL pH (p<0.0001 relative to the CuFi-1 control). The magnitude of improvement in ΔpH observed with the lipid-coated crystal compositions is significantly greater than the ~0.15-0.2 pH unit improvement observed with the AmB:Chol complexes utilized by Burke et al. (US 2019/0083517; US 2020/0352970).

Example 13: Evaluation of Relative Viscosity of ASL Fluid in Primary Cultured Epithelial Cells from People with CF Following Administration of ABCI-003

The absence or dysfunction of the CFTR protein leads to defective ion transport—the underlying defect that causes depletion of ASL (i.e., increases in ASL thickness), increases in ASL viscosity, and impaired mucociliary clearance.

The ability of ABCI to reduce the viscosity of ASL fluid in primary cultures of CF airway epithelial cells relative to the FC-72 delivery vehicle alone was evaluated. Apical addition of ABCI to primary cultures of CF airway epithelia decreased mean ASL viscosity ($\tau_{ASL}/\tau_{saline}$) values from 3.3 to about 1.9 to 2.2 times that of saline; similar activity was observed regardless of CFTR genotype (FIG. 10).

The ASL of non-CF airway epithelia has a relative viscosity 2.5 times that of saline. Hence, these data demonstrate that ABCI can reduce the relative viscosity of ASL in CF airway epithelia to levels like those observed in airway epithelial cells from individuals without CF. Since increased viscosity of ASL is associated with impaired mucociliary clearance and increased risk of infection/inflammation in subjects with CF, these data suggest the potential for compositions according to embodiments described herein to mitigate one of the most serious sequelae of CF in the airways.

Example 14: Antimicrobial Killing Activity of ASL Fluid in Primary Cultured Epithelial Cells From People With CF Following Administration of ABCI Many aspects of the innate host defense system of the airways are pH sensitive, including the rheological properties of secreted mucins, mucociliary clearance, the activity of proteases, and the activity of antimicrobial peptides (e.g., defensins). The antimicrobial activity of ASL on *S. aureus* in coated gold grids is reduced by approximately 50% in primary airway epithelia derived from subjects without CF.

The effect of apical administration of ABCI-003 relative to the FC-72 delivery vehicle alone on ASL antibacterial activity was evaluated in primary cultured airway epithelia cells derived from six subjects with CF with different CFTR mutations. Exposure of CF-derived airway epithelial cells to ABCI-003 increased the percentage of *S. aureus* killed from about 22% in the vehicle control to about 40% in the high dose ABCI-003 group (i.e., nearly doubling the antimicrobial activity of ASL to levels similar to those measured in non-CF cells) (FIG. 11).

Figure 11:
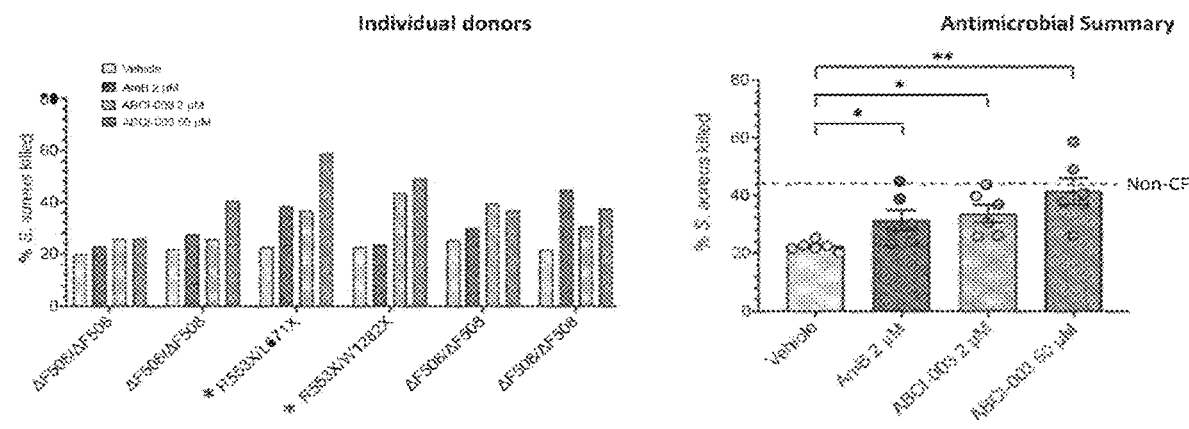
FIG. 11 displays a plot showing increases in ASL antimicrobial activity following administration of ABCI-003 to primary cultured airway epithelial cells from individuals with CF, including those with nonsense mutations.

The CFTR mutation status of subjects with CF from whom the cells were derived is shown in (FIG. 11). Notably, the response in cells from the two individuals that had two nonsense mutations (for whom modulator drugs would not be effective) was at least as great as those with the more common ΔF508 mutation, who are candidates for modulator therapy. Moreover, the improved bacterial killing of ASL for 50 µM ABCI-003 dose was similar to the non-CF controls.

Example 15: Impact of Lipid Composition and AmB Crystallinity on Hemolysis

Toxicity of AmB. Intravenous administration of Fungizone results in numerous acute systemic reactions including fever, shaking, chills, hypotension, hypertension, anorexia, nausea, vomiting, headache, and tachypnea, leading to its nickname of 'amphoterrible'. Its principal chronic adverse effect is nephrotoxicity. The lipid-based compositions (e.g., L-AMB) reduce the acute systemic effects, but the nephrotoxicity remains as a dose-limiting toxicity. Recent studies in the Burke lab suggest that the toxic effects of AmB in mammalian cells is not the result of ion channel formation as has been postulated, but rather is due to extraction of cholesterol from cell membranes into an extra-membranous sterol sponge phase (Anderson et al. *Nature Chem Biol.* 2014; 10:400-406; Gray et al. *PNAS.* 2012; 109:2234-2239). Toxicity from Chol extraction was thought to occur only when the ratio of sterol:AmB is less than ~1.0 mol/mol.

The physical form of the API (i.e., amorphous versus crystalline) and size of the particles may impact the 'apparent' solubility of AmB in water. This in turn may influence the safety profile of the drug following parenteral administration (Ghielmetti et al. *J. Pharm Sci.* 1976; 65:905-907; Bennett et al. *Antimicrob Agents Chemother.* 1963; 161:745-752) and following oral inhalation (US 2012/0128728). In the context of the present disclosure, a hemolysis assay was used to assess the impact of physical form of the API and composition attributes on Chol extraction from red blood cell membranes.

Table 15 compares hemolysis following administration of various compositions comprising AmB. Fungizone®, a micellar composition of AmB solubilized in sodium deoxycholate micelles with no Chol, serves as a positive control, while L-AMB serves as a negative control. ABCI-001, ABCI-002, and ABCI-003, which all comprise highly crystalline AmB and Chol, exhibit hemolysis similar to the negative control. Surprisingly, this is true even for Chol/AmB ratios significantly less than 1.0. For example, ABCI-003 which has a theoretical Chol/AmB ratio of just 0.4 mol/mol (actual=0.33 mol/mol) has hemolysis comparable to L-AMB.

TABLE 15

Hemolysis of Compositions Comprising AmB

| Batch | Description | Hemolysis at 100 mM AmB Concentration (%) |
|---|---|---|
| | Fungizone; (positive control) | 90 |
| | AmBisome (L-AMB); (negative control) | <5 |
| | AmB (100% crystalline) | <5 |
| | AmB (100% amorphous) | 100 |
| R20047 | ABIP (crystalline AmB); no Chol | <5 |
| R20048 | ABIP (amorphous AmB); no Chol | 40 |
| R21052 | ABCI-001 | <5 |
| R21061 | ABCI-002 | <5 |
| R21058 | ABCI-003 | <5 |

The case with ABIP compositions is instructive. ABIP formulated with fully amorphous AmB is highly hemolytic, while ABIP formulated with crystalline drug is not, showing that the physical form or 'apparent solubility' of the amorphous phase can potentiate the effect.

Example 16: Drug Loading and Target Densities in Dry Powder Compositions

The nominal dose (ND), tapped density ($\rho_{tapped}$), and the receptacle volume ($V_r$) of the dry powder inhaler may be used to calculate the drug loading according to the below equation:

$$\% \ AmB = \frac{0.2 \times ND(\text{mg})}{V_r(\text{mL}) \times \rho_{tapped}\left(\frac{\text{g}}{\text{cm}^3}\right)}$$

The equation assumes 50% of receptacle volume is filled. Optimal performance for capsules may occur for fill volumes between 25% and 75% of the capsule volume, although fill volumes as low as about 10% and as high as 90% may be used. Too low of a fill volume may result in decreased emitted dose (ED) values, due to fixed losses in the capsule and device during aerosol administration.

For a 2 mg nominal dose (ND) with a powder having a tapped density of 0.1 g/mL (size 3 capsule), the % AmB is ~13.4% w/w for a capsule half full, ranging from 6.7% to 20.1% w/w for 25% to 75% of the fill volume. Hence, ABCI-003 powder with a tapped density of 0.11 g/mL may be well designed for achieving a target 2 mg dose.

For a 0.67 mg ND with a tapped density of 0.1 g/mL, the % AmB would be 4.5%, with a range from 2.25-6.75% w/w for 25% to 75% of the size 3 capsule volume filled.

For a 0.1 mg nominal dose, the required drug loading to achieve a 50% fill volume is about 0.7% (tapped density=0.1 g/mL).

Figures 12A, 12B:
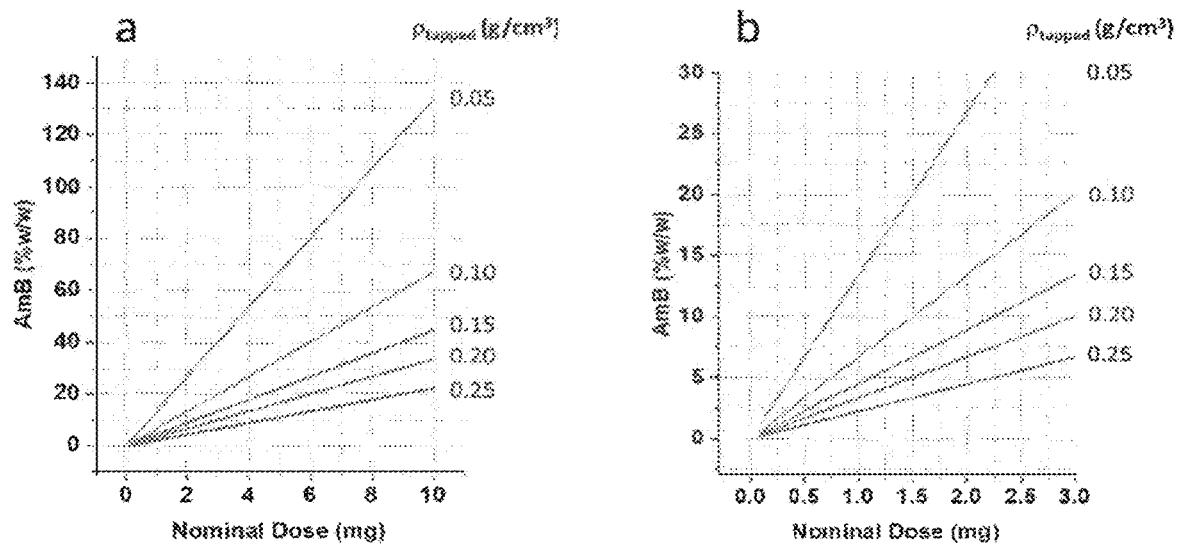
FIG. 12A displays a plot showing the impact of the nominal and tapped density of spray-dried powder compositions on calculated drug loading for the bulk powder at a nominal dose range from 0 to 10 mg.
FIG. 12B displays a plot showing the impact of the nominal and tapped density of spray-dried powder compositions on calculated drug loading for the bulk powder at a nominal dose range from 0 to 3 mg.

FIG. 12 provides an estimate of the drug loading requirements based on the nominal dose and tapped density of the powder.

Overall, for nominal doses less than about 10 mg, the % AmB varies from 0.1% to 50%, such as 0.5% to 20%. For nominal doses on the order of 10 mg, it may be advantageous to adjust the tapped density to be on the order of 0.2 g/cm$^3$, while for the lower doses less than 3 mg, it is advantageous to utilize a lower tapped density on the order of 0.1 g/cm$^3$. Tapped density within the spray-dried powders can be controlled in the composition through variations in the spray drying conditions, solids content, and through variations in the concentration of the pore-forming process aid, PFOB.

Example 17: Clearance of Compositions From Airway Surface Liquid

Administration of compositions according to the present disclosure via oral inhalation deposits AmB in ASL on the apical side of airway epithelial cells, where ion channel formation in the epithelial cell membrane occurs. Given that only drug that is dissolved in ASL may contribute to ion channel formation, it is desirable to choose a dose and regimen that maintains trough ASL concentrations well above the equilibrium solubility of AmB in ASL (i.e., >0.2 µg/mL).

Drug particles deposited in the airway lumen following inhalation (IH) administration are distributed from ASL into other compartments by multiple clearance pathways. These include: (1) absorption of dissolved AmB from ASL into the systemic circulation; (2) particulate clearance on the mucociliary escalator or by cough clearance; (3) phagocytosis of particles by circulating and tissue resident alveolar macrophages, and (4) binding or association of AmB with lung issue.

Owing to the low solubility of AmB, systemic absorption is dissolution limited, and most of the drug not cleared on the mucociliary escalator will be distributed into lung tissue where owing to its slow clearance accumulates over time. Like intravenous administration, IH administration of AmB results in biphasic elimination kinetics from ASL and plasma due to the slow redistribution of drug from lung tissue.

The clearance of ABCI-001 from ASL was assessed in bronchoalveolar lavage fluid (BALF) samples obtained from Sprague-Dawley rats following both IT (Study FY21-211A) and IH (Study FY21-211B) administration. FY21-211A and FY21-211B were both non-GLP single-dose studies. Study FY21-211A evaluated IT administration of ABCI-001 and ABIP at delivered doses of 5 mg/kg. Study FY21-211B evaluated three delivered doses of ABCI-001 (6.8, 13.6 and 23 mg/kg) by nose-only inhalation. BALF collections were evaluated at six timepoints (0.5, 1, 2, 4, 8, and 16 hours post dose) in both studies. The bronchoalveolar lavage procedure significantly dilutes the concentration of AmB in ASL. Urea may be used as an endogenous marker of ASL dilution, as rapid diffusion of urea through the body results in identical concentrations in plasma and ASL. This enables the ASL volume in a BALF sample to be calculated from simple dilution principles. AmB concentrations in ASL were quantitated using a liquid chromatography with tandem mass spectrometry (LC-MS/MS) method, while urea concentrations in ASL and plasma were quantitated with a colorimetric blood urea nitrogen assay.

ASL AmB concentration versus time profiles for the three delivered doses of ABCI-001 administered in FY21-211B (6.8, 13.6, and 23.0 mg/kg) were combined on a single graph, with the results obtained following intratracheal administration of 5 mg/kg doses of ABCI-001 and ABIP in Study FY21-211A. To do this, ASL concentrations were normalized to the 12 mg/kg dose level. Because the dose normalized ASL concentration versus time profile for each of the 5 treatments overlapped significantly and appeared to share a similar rate of decline, the pooled data were fit with the equation for mono-exponential decline to estimate this initial rate of ASL clearance in rats. The results indicate that exposure to and initial disposition of AmB in ASL are essentially independent of the administered ABCI-001 dose and comparable to ABIP. In addition, the half-life of the initial decline of AmB in ASL following administration of ABCI-001 and ABIP to rats in this study was ~16 hours. This rate of clearance of AmB from ASL may support once daily dosing of compositions according to embodiments described herein.

Example 18: Lung Tissue Distribution and Clearance for AmB in Rats and Dogs Following IH Administration of Compositions Following IH administration, a significant proportion of AmB present in ASL is distributed into lung tissue. Lung tissue concentrations were measured in 28-day GLP toxicology studies with ABCI-001 in Sprague-Dawley rats (Study FY21-235), and with ABCI-003 in rats (Study FY22-071) and beagle dogs with ABCI-003 (Study FY21-234). Lung tissue concentrations were also measured in rats in a non-GLP study following administration of a single dose of ABCI-001 (Study FY21-211B), and multiple doses of ABCI-003 (Study FY22-070). The mean lung tissue concentrations at necropsy are detailed in Table 16.

cant accumulation in lung tissue was also observed for ABIP in a 14-day GLP study in dogs. Following cessation of dosing the $t_{1/2}$ for redistribution of AmB from lung tissue was 19 days. In a corresponding 14-day GLP study in rats,

TABLE 16

Lung Tissue Concentrations of AmB in Rats and Dogs Following IH Administration of Compositions

| Study | Species | Composition | DD (mg/kg) | Freq | Day | Lung Burden (mg/g) | Macrophage Response |
|---|---|---|---|---|---|---|---|
| FY21-211B | Rat | ABCI-001 | 6.8 | QD | 1 | 0.010 ± 0.005 | Adaptive |
|  |  |  | 13.6 | QD | 1 | 0.014 ± 0.006 | Adaptive |
|  |  |  | 23.0 | QD | 1 | 0.016 ± 0.006 | Adaptive |
| FY21-235 | Rat | ABCI-001 | 4.7 | QD | 28 | 1.42 ± 0.29 | Adverse |
|  |  |  | 9.3 | QD | 28 | 1.93 ± 0.27 | Adverse |
|  |  |  | 17.3 | QD | 28 | 2.94 ± 0.52 | Adverse |
| FY22-070 | Rat | ABCI-003 | 4.8 | QD | 14 | 1.70 ± 0.44 | Adverse |
| FY22-071 | Rat | ABCI-003 | 1.1/0.2 | QW | 29 | 0.019 ± 0.004 | Adaptive |
|  |  |  | 2.6/0.4 | QW | 29 | 0.050 ± 0.014 | Adaptive |
|  |  |  | 5.7/1.1 | QW | 29 | 0.088 ± 0.031 | Adaptive |
| FY21-234 | Dog | ABCI-003 | 0.5 | QD | 28 | 0.25 ± 0.08 | Adaptive |
|  |  |  | 1.8 | QD | 28 | 1.38 ± 0.61 | Adaptive |
|  |  |  | 4.9 | QD | 28 | 3.54 ± 0.65 | Adaptive |
| Phase 1 | Human | ABCI-003 | 10/4 | QD | 28 | 0.08 (estimate) |  |

SD = standard deviation;
QW = once weekly
[1] With the exception of the day 42 and day 57 measurements, all lung tissue concentrations were quantitated 24 hours after the last dose administration
[2] In study FY22-071 dosing was weekly (QW) with a loading/maintenance dose After repeated delivered doses ≥1.8 mg/kg/day over 14 or 28 days, mean lung concentrations of AmB generally exceeded 1.0 mg/g in both rats and dogs. Lung concentrations in both species increased with increasing dose, but in a less than proportional manner. Mean lung tissue concentration of AmB from ABCI-001 and ABCI-003 in both species at the end of repeated dosing were approximately 80- to 100-times higher than reported for AmB in lung tissue following repeated IV administration of liposomal AmB. The lung tissue concentrations observed with ABCI-001 and ABCI-003 are comparable to those measured for L-AMB in the liver and spleen (1-10 mg/g) following IV administration. The lung tissue concentrations observed with repeated dosing of ABCI-001 and ABCI-003 (>1.0 mg/g) are significantly greater than the lung tissue concentrations determined following administration of single doses of ABCI-001 and ABCI-003 (<0.1 mg/g), even at single doses as high as 23.0 mg/kg (Study FY21-211B). The large increases in lung tissue levels with repeated dosing are due to accumulation of the practically insoluble drug substance in the lungs. The accumulation ratio, AR, represents the relationship between the dosing interval and the rate of elimination of the drug at steady state, viz: $AR=1/1-e^{-k\tau}$ where k is the terminal elimination rate constant and $\tau$ is the dosing interval.

The measured $t_{1/2}$ for ABCI-003 in lung tissue in FY21-234 in dogs was about 10 days. The lung tissue $t_{1/2}$ measured during the wash-out of ABCI-003 in rats (Study FY22-071) was 20-25 days in the mid- and high-dose groups. Signifithe $t_{1/2}$ for redistribution from lung tissue were 22 and 34 days for delivered doses of 1.1 and 12.4 mg/kg, respectively. These results are consistent with the 1 to 4-week $t_{1/2}$ measured for clearance of AmB from the liver following IV administration. The slow redistribution of drug from lung tissue leads to biphasic clearance of drug from ASL and plasma, due to flip-flop PK where a drug's rate at which it enters the ASL, or plasma compartments is slower than its absorption or elimination rate.

If the terminal $t_{1/2}$ for AmB is assumed to be ~20 days, then k~0.035 day$^{-1}$. For once daily administration, AR is equal to 29.4, which indicates that the daily AmB dose will accumulate up to 30-fold in lung tissue at steady state. This degree of accumulation is reflected in the high lung tissue concentrations measured in rats and dogs for ABIP, ABCI-001, and ABCI-003.

The lower AmB exposures in lung tissue observed in the FY22-071 study are due to the lower delivered doses and once weekly dosing regimen. For once weekly dosing of ABCI-003, AR is equal to 4.6. A loading dose 5-fold higher than the maintenance dose can be used to maintain a constant lung tissue concentration over the period of dosing. Given that our therapeutic target is ASL, rapidly achieving equilibrium concentrations of AmB in lung tissue is less important than doing so in ASL.

Maintaining trough concentrations in ASL >0.2 µg/mL may be important for efficacy with the compositions described herein. As discussed, the measured $t_{1/2}$ of AmB in ASL is ~16 hours. This results in an AR of about 2 at steady state. Hence, a loading dose that is 2.5 to 3-fold greater than the maintenance dose may enable consistent ASL peak and trough AmB concentrations over the dosing period of the compositions described herein.

Example 19: Plasma Toxicokinetics for AmB in Rats and Dogs Following IH Administration Elimination of AmB from plasma was evaluated for male and female Sprague-Dawley rats following inhalation of single or repeated doses of ABCI-001 in a 28-day GLP toxicology study (Study FY21-235). The study included three treatment groups having group averaged, achieved delivered doses of: 4.7 mg/kg (Low-Dose), 9.3 mg/kg (Mid-Dose), and 17.3 mg/kg (High-Dose). Plasma samples were collected at pre-dose, 0.25, 0.5, 1.0, 2.0, 4.0, 8.0, 16.0 and 24.0 hours post-administration and plasma AmB concentrations were quantitated with a validated LC-MS/MS method having a lower limit of quantitation of 1 ng/mL. Toxicokinetic parameters were determined using Phoenix WinNonlin version 8.3 software.

Although females consistently showed higher exposures than males, there was limited evidence of differences between the sexes. As a result, male and female combined averages are presented in Table 17. Owing to the low solubility of AmB, systemic absorption of AmB was slow following single or repeated inhalations, with median time to maximum concentration ($t_{max}$) values generally observed between 4 and 8 hours, independent of dose, animal sex, and administration day. There was minimal accumulation of AmB in plasma observed over the 28-day dosing period, with mean accumulation ratios for dose-normalized area under the time concentration curve to the last measurable concentration ($AUC_{last}$) and maximum concentration ($C_{max}$) ranging from 0.699 to 1.51. On day 1, low-, mid- and high-dose males passed reporting criteria such that their plasma ABCI-001 elimination $t_{1/2}$ could be estimated with values ranging from 5.28 to 8.55 hours. On day 28, the elimination $t_{1/2}$ for low- and mid-dose females were between 7.16 and 9.33 hours. These values are consistent with the 8-hour $t_{1/2}$ value reported for a 4 mg/kg IV dose of AmBisome in rats with a 24-hour sampling period.

TABLE 17

Summary of Mean TK Parameters in Rat Plasma Following Dosing of ABCI-001 on Day 1 or Following 28 Consecutive Daily Doses on Day 28 for Low, Mid, and High Dose (Study FY21-235)

| Metric | Low Dose (4.7 mg/kg) | | Mid-Dose (9.3 mg/kg) | | High Dose (17.3 mg/kg) | |
|---|---|---|---|---|---|---|
| | Day 1 | Day 28 | Day 1 | Day 28 | Day 1 | Day 28 |
| $C_{max}$ (ng/mL) | 52.7 ± 15.0 | 36.9 ± 10.6 | 48.7 ± 9.7 | 46.1 ± 20.0 | 53.6 ± 8.4 | 54.5 ± 21.3 |
| $AUC_{0-24\,h}$ (hr ng/mL) | 701 ± 200 | 557 ± 130 | 747 ± 245 | 682 ± 230 | 794 ± 68 | 1010 ± 364 |
| $t_{1/2}$ (h) | 5.56 | 7.16 | 5.28 | 9.33 | 8.55 | N.A. |

$AUC_{0-24\,hr}$ = area under the time concentration curve from 0 to 24 hours;
$C_{max}$ = maximum concentration;
$t_{1/2}$ = half-life Mean plasma $C_{max}$ values in rats were about two orders of magnitude greater for IV liposomal AmB (AmBisome) in comparison with IH ABCI-001 at comparable doses (Table 18), while lung tissue $C_{max}$ values are 83-fold lower. The absolute bioavailability for ABCI absorbed systemically over 24 hours on day 1 is about 3%, assuming a lung deposition fraction of 0.1 in rats. This is additional evidence for the high distribution of drug into tissue.

IH administration provides significant targeting of drug to the lungs, with lung tissue concentrations nearly two orders of magnitude higher and plasma concentrations two orders of magnitude lower than that achieved following IV administration.

TABLE 18

Comparison of Plasma and Lung Tissue Exposure of IH ABCI-001 with IV AmBisome at Comparable Doses in Sprague-Dawley Rats

| Product | Route | Dose (mg/kg) | Day | Plasma $C_{max}$ (ng/mL) | $C_{max}$ (IV)/ $C_{max}$ (IH) (plasma) | Lung $C_{max}$ (mg/g) | $C_{max}$ IH/ $C_{max}$ (IV) (lung) |
|---|---|---|---|---|---|---|---|
| AmBisome | IV | 4 | 1 | 14200 ± 2450 | 269 | 14.5 | |
| ABCI-001 | IH | 4.7 | 1 | 52.7 ± 15.0 | | 1200 | 83 |

Plasma TK was also evaluated for male and female beagle dogs following inhalation of single or repeated doses of ABCI-003 in a 28-day GLP toxicology study (Study FY21-234). This study included three dose groups with mean delivered doses of: 0.51 mg/kg (Low-Dose), 1.8 mg/kg (Mid-Dose), and 4.9 mg/kg (High-Dose). Sample collection times, AmB quantitation and noncompartmental data analysis were conducted in the same manner as described above for the rat.

There was limited evidence of overt sex differences, so male and female combined averages are presented in Table 19. As in the rat, plasma exposure increased in a less than dose proportional manner on day 1 and 28, with AmB concentrations remaining elevated at or near the level of $C_{max}$ until the 24-hour timepoint, especially for the mid- and high-dose groups. Concentrations were still quantifiable in all animals at necropsy on day 28 and after 14 days of recovery from inhalations on day 42.

TABLE 19

Summary of ABCI Mean TK Parameters (± SD) in Dog Plasma Following a Single Dose on Day 1 or Day 28 (Study FY21-234)

| Metric | Low-Dose (0.51 mg/kg) | | Mid-Dose (1.8 mg/kg) | | High Dose (4.9 mg/kg) | |
|---|---|---|---|---|---|---|
| | Day 1 | Day 28 | Day 1 | Day 28 | Day 1 | Day 28 |
| $C_{max}$ (ng/mL) | 3.02 ± 0.79 | 9.56 ± 4.25 | 6.44 ± 2.43 | 13.9 ± 4.4 | 15.0 ± 5.1 | 33.8 ± 9.2 |
| $AUC_{0-24\ h}$ (hr ng/mL) | 53.6 ± 10.3 | 166 ± 52 | 115 ± 42 | 265 ± 71 | 263 ± 86 | 655 ± 183 |

In contrast to the rat, there was consistent evidence of plasma AmB accumulation in the dog over the 28-day dosing period, with mean accumulation ratios for dose-normalized area under the time concentration curve from 0 to 24 hours ($AUC_{0-24\ hr}$) and $C_{max}$ values ranging from 1.54 to 3.58. This difference in drug disposition may reflect differences in lung anatomy and physiology between the two species. The magnitude of the measured plasma concentrations and accumulation observed with ABCI-003 were consistent with previous studies with ABIP.

Plasma ABCI-003 elimination $t_{1/2}$ was only able to be estimated and passed reporting criteria for two high-dose female animals in the recovery study, with values of 103 and 105 hours. Due to the slow clearance of AmB from plasma resulting from redistribution from tissue, as discussed for IV compositions, the $t_{1/2}$ measured using non-compartmental methods is heavily influenced by the sampling time. The longer $t_{1/2}$ observed in dogs relative to the rats (~100 hours versus 5-10 hours) is simply a reflection of the longer sampling period (i.e., out to day 42 with the recovery animals).

Mean plasma $C_{max}$ values in dogs were about two orders of magnitude greater for IV AmB deoxycholate (Fungizone®) and about three orders of magnitude for IV liposomal AmB (AmBisome®) in comparison with IH ABCI-003 at comparable doses (Table 20). Lung tissue concentrations are 19 to 100-fold higher for ABCI-003. The absolute bioavailability over 24 hours was 0.6% assuming a deposition fraction of 0.25 in the dog. The low bioavailability observed in the rats and dogs is consistent with the low systemic toxicity observed with IH administration of Fungizone® and AmBisome® and anticipated for IH of the compositions according to embodiments described herein.

TABLE 20

Comparison of Plasma and Lung Tissue Exposure of IH ABCI with IV Fungizone and AmBisome at Comparable Doses in Beagle Dogs

| Product | Route | Dose (mg/kg) | Day | Plasma $C_{max}$ (ng/mL) | $C_{max}$ (IV)/ $C_{max}$ (IH) (plasma) | Lung $C_{max}$ (mg/g) | $C_{max}$ IH/ $C_{max}$ (IV) (lung) |
|---|---|---|---|---|---|---|---|
| Fungizone | IV | 0.6 | 1 | 232 | 77 | | |
| | | | 14 | 1323 | 138 | 15.4 | |
| ABCI-003 | IH | 0.5 | 1 | 3 | | | |
| | | | 28 | 9.6 | | 300 | 19 |
| AmBisome | IV | 4 | 1 | 20000 | 1333 | | |
| | | | 30 | 100000 | 2954 | 31 | |
| ABCI-003 | IH | 4.9 | 1 | 15 | | | |
| | | | 28 | 33.8 | | 3100 | 100 |

Example 20: Toxicology Studies in Rats and Dogs

Toxicity Observed in Study FY21-211B (Single Dose Study in Rats). In Study FY21-211B, single doses of 6.8, 13.6, and 23.0 mg/kg of ABCI-001 were administered via nose-only inhalation to 54 Sprague-Dawley rats in a non-GLP study. The ABCI-001 composition comprises 30% w/w AmB and a Chol/AmB ratio of 1.2 mol/mol. ABCI-001 was well tolerated with no abnormal clinical observations or macroscopic observations at necropsy. AmB exposure in plasma, ASL and lung tissue tended to increase with increasing dose, albeit in a less than dose proportional manner. The measured lung tissue concentrations were 0.010, 0.014, and 0.016 mg/g, respectively. Although dose-dependent increases in alveolar macrophages were observed, there were no adverse changes (e.g., increases in inflammatory cells) noted in histopathology. The increases in macrophages were ascribed to normal particulate clearance of the inhaled dry powder. Although a non-GLP study, the 23.0 mg/kg dose would support a single human dose of ABCI of ~46 mg with a 10-fold safety margin.

Toxicity Observed in Study FY21-235 (28-d GLP Study in Rats). Following the successful single-dose study, a 28-d GLP repeat dose toxicology study with a 14-day recovery was conducted in rats with ABCI-001 (Study FY21-235). Slow clearance of the practically insoluble AmB drug substance led to significant accumulation of AmB in lung tissue following daily doses of 4.7, 9.3, 17.3 mg/kg/day. Lung tissue concentrations of AmB in the low-, mid-, and high-dose groups were 1.2, 2.0, and 2.9 mg/g, respectively.

Peak plasma drug concentration remained less than 55 ng/mL, two to three orders of magnitude lower than was observed for following intravenous administration of AmB at comparable concentrations, and well below the 1000 ng/mL threshold for systemic toxicity.

In the low, mid, and high dose groups, early deaths occurred in 4/38, 3/38, and 13/47 animals, respectively. This was presumed to result from obstruction of the large airways due to hypersecretion of mucinous material. Some animals in ABCI-001 treated groups had respiratory-related symptoms (wheezing, palpable rales, rapid respiration) intermittently during the dosing phase. First symptoms appeared in the high dose group on day 4 and appeared more frequently with continued exposure. There was a poor correlation between the clinical signs and mortality, however.

There were no important differences in body weight, food consumption, hematology, clinical chemistry, and coagulation observed.

Histopathology assessment revealed lesions in the larynx, trachea, and lungs of males and females in all dose groups. Findings consisted of minimal to moderate increases in yellow/gold pigmented macrophages, minimal to moderate mixed cell inflammation in the larynx, trachea, and lungs, minimal to moderate accumulation of mucinous material, and minimal to moderate increases in respiratory epithelial cell hyperplasia. Due to the significant morbidity and mortality observed in Study FY21-235, a no observable adverse effect level (NOAEL) could not be established. The lowest adverse effect level (LOAEL) was the lowest dose studied (4.7 mg/kg).

Study FY22-071 (28-d GLP Study in Rats). A second 28-day GLP study with a 14-day recovery was conducted in Sprague-Dawley rats (Study FY22-071). This study utilized ABCI-003 and achieved a much lower AmB burden in lung tissue. The ABCI-003 composition comprises 14% w/w AmB with a Chol/AmB ratio of 0.4 mol/mol. Compared to ABCI-001, ABCI-003 may have reduced interparticle cohesive forces due to maintenance of the lipids in the highly ordered so phase. The three dose groups utilized a loading dose followed by weekly maintenance doses. The low-, mid- and high-dose doses were: 1.08/0.17 mg/kg, 2.54/0.41 mg/kg, and 5.74/1.06 mg/kg, respectively. Lung tissue concentrations were 0.019, 0.050 and 0.088 mg/g for the low-, mid- and high-dose groups, respectively).

In contrast to Study FY21-235, the in-life portion of Study FY22-071 showed no evidence of morbidity or mortality. Gross pathology results were also unremarkable. While minimal increases in macrophages were observed, these findings were not accompanied by the adverse findings (mucinous material, epithelial hyperplasia, or inflammation) noted in Study FY21-235. There were no important differences in body weight, food consumption, hematology, clinical chemistry, and coagulation observed. The NOAEL was the highest administered dose, i.e., 5.74/1.06 mg/kg.

Study FY21-234 (28-d GLP Study in Dogs). Study FY21-234 administered ABCI-003 to beagle dogs at daily doses of 0.5, 1.8, and 4.9 mg/kg. The high dose in the dogs was comparable to the low dose in Study FY21-235 in rats where no NOAEL was established. Moreover, like the rat, the exposures in lung tissue were high (0.25, 1.38, and 3.54 mg/g). In contrast to the rat study, however, no morbidity or mortality was observed in the dogs at any dose. The clinical signs, body weight, food consumption, clinical pathology (hematology, coagulation, urinalysis), ophthalmology, ECG parameters were all unaffected by treatment with ABCI-003. Clinical pathology results for Day 29 for Low Dose indicated no effects. Unfortunately, due to Clinical Chemistry Analyzer malfunction, the data for the mid- and high-dose groups on day 29 and the recovery groups (air, placebo controls and high-dose) were not evaluable. Given the known clinical profile of effects on clinical chemistry of systemic AmB administration at orders of magnitude greater plasma exposures and the fact that no clinical chemistry findings were observed in any other inhalation toxicology studies of the compositions and AmB related compositions (e.g., ABIP), the concern of potential missed clinical pathology findings are unlikely.

Moreover, although increases in the number of pigmented macrophages were observed, there were no signs of increases in inflammation, mucus hypersecretion, or epithelial cell hyperplasia. The histopathology findings were deemed to be non-adverse and consistent with normal particulate clearance from the lungs. The NOAEL was the high dose group, i.e., 4.9 mg/kg/day.

Summary Without intending to be bound by theory, it is believed that the slow clearance of AmB from lung tissue leads to significant accumulation of drug with daily dosing. Large amounts of undissolved particulate material of any kind within the lungs can result in adaptive, and ultimately adverse, lung changes related simply to the physical burden of foreign material present in the respiratory tract. These changes may be independent of any chemically based or pharmacologically mediated toxicity of the drug.

With increasing amounts of insoluble material, the number of macrophages increase, and excessive macrophages stimulation leads to recruitment of other inflammatory cells and can eventually produce secondary tissue damage. This response is often referred to as 'lung overload'. It is important to distinguish this from a reduction in macrophage lung clearance due to volumetric overload of low toxicity particulates from direct macrophage toxicity from compounds such as crystalline quartz, which may kill macrophages or impair their function.

Adverse observations associated with lung overload occur in rats when the concentration of poorly soluble particles (e.g., titanium dioxide, carbon black) in lung tissue exceed ~1 mg/g. Adaptive responses (i.e., increases in macrophages with no inflammatory response) are typically observed for concentrations below ~0.1 mg/g.

In Study FY21-235, the lung concentrations of AmB in the low-, mid-, and high-dose groups were 1.2, 2.0, and 2.9 mg/g, respectively, exceeding the threshold concentration for lung overload in rats. Consistent with the lung overload phenomenon, these lung burdens led to significant morbidity and mortality in all dose groups. This is consistent with other studies demonstrating rat macrophages are particularly sensitive to overload.

In Study FY22-071, the dose and regimen were adjusted to maintain AmB lung tissue concentrations less than the 0.1 mg/g threshold, below which only adaptive macrophage responses are anticipated. Indeed, only minimal increases in macrophage were observed, with no evidence of toxicity associated with lung overload.

It is also noteworthy that a single dose of ABCI-001 as high as 23 mg/kg (Study FY21-211B) also resulted in a low lung burden (0.016 mg/g) and an adaptive macrophage response in rats. This suggests that the adverse effect may not be an acute response to high AmB concentrations on the pulmonary epithelium post-dosing, but rather may result from accumulation of drug in lung tissue over time.

The adaptive and adverse responses observed with the compositions in rats at concentrations greater than 1.0 mg/g and below 0.1 mg/g are consistent with that reported for insoluble compounds like titanium dioxide and carbon black. These observations support the assertion that the observed toxicity with ABCI-001 in Study FY21-235 is not a chemically or pharmacologically mediated drug effect, but rather is due to a macrophage response associated with lung overload of practically insoluble particles.

In general, rats are far more sensitive to the effects of lung overload than other species under similar dosing conditions. This is clearly the case with ABCI-003, where a NOAEL was established in the dog at a deposited dose of 1.23 mg/kg, whereas lung overload was still observed in the rat at a deposited dose about three-fold lower (0.47 mg/kg). Forbes and colleagues summarized species differences associated with macrophage overload, reporting that rats are more sensitive to this phenomenon than either mice or hamsters (Forbes et al. Adv Drug Deliv Rev. 2014, 71, 15-33). Despite having a higher fractional deposition and slower rate of clearance of poorly soluble particles (e.g., titanium dioxide, coal dust, silica), pulmonary overload is not common in humans. The decreased sensitivity appears to be related to anatomic differences (i.e., no respiratory bronchioles in rats) and physiological differences (i.e., greater particle uptake by interstitial macrophages and transport to lymphatics). Hence, the toxicity observed in the rat may not be predictive of toxicity in humans, and the dog is deemed to be a most appropriate species for assessing human risk.

While the rat is a sensitive species, it is believed that the dog is a more relevant species for assessing human risk. The NOAEL in the dog (4.9 mg/kg) provides a 12.6-fold safety margin relative to the maximum proposed nominal dose in Phase 1 single-ascending dose clinical study in healthy volunteers (i.e., 10 mg). The margin increases to 31.5-fold for the maximum proposed daily dose in a Phase 1 multiple ascending dose study in healthy volunteers.

An alternative way of estimating a safety margin is detailed below based on AmB exposure in lung tissue. The anticipated lung tissue concentrations in human subjects following 28 days of dosing of a 10 mg loading dose followed by a 4 mg daily maintenance dose in humans is 0.08 mg/g. This is 12.5-fold below the lung tissue concentration in rats that is known to cause lung overload. Moreover, it is less than the 0.1 mg/g lung tissue concentration below which only adaptive responses are observed in the rat.

Figure 13:
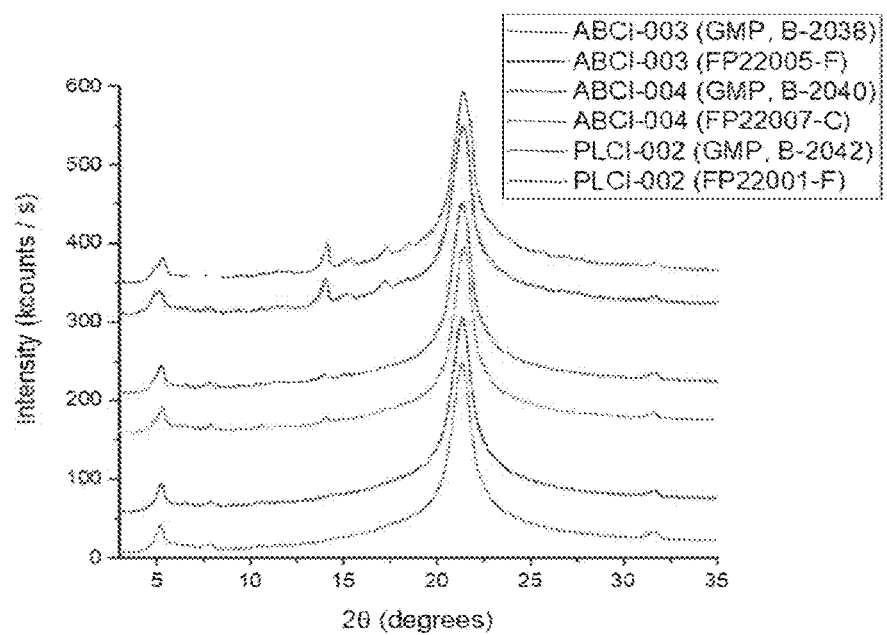
FIG. 13 displays an overlay of X-Ray Powder Diffraction Patterns of GMP and GLP Batches of ABCI-003, ABCI-004, and PLCI-002
Figure 14:
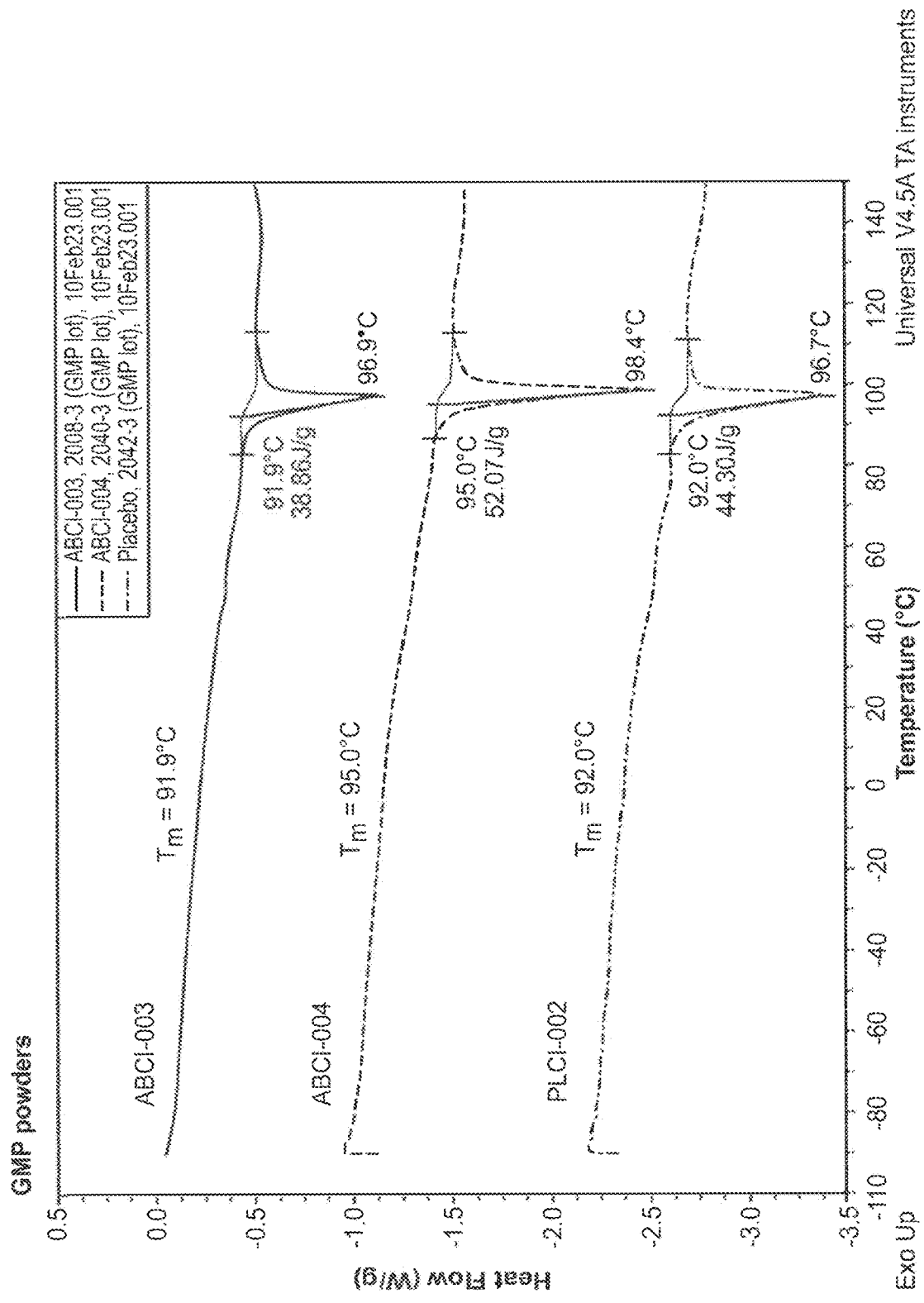
FIG. 14 displays an overlay of DSC Thermograms of GMP and GLP Batches of ABCI-003, ABCI-004, and PLCI-002
Figure 15:
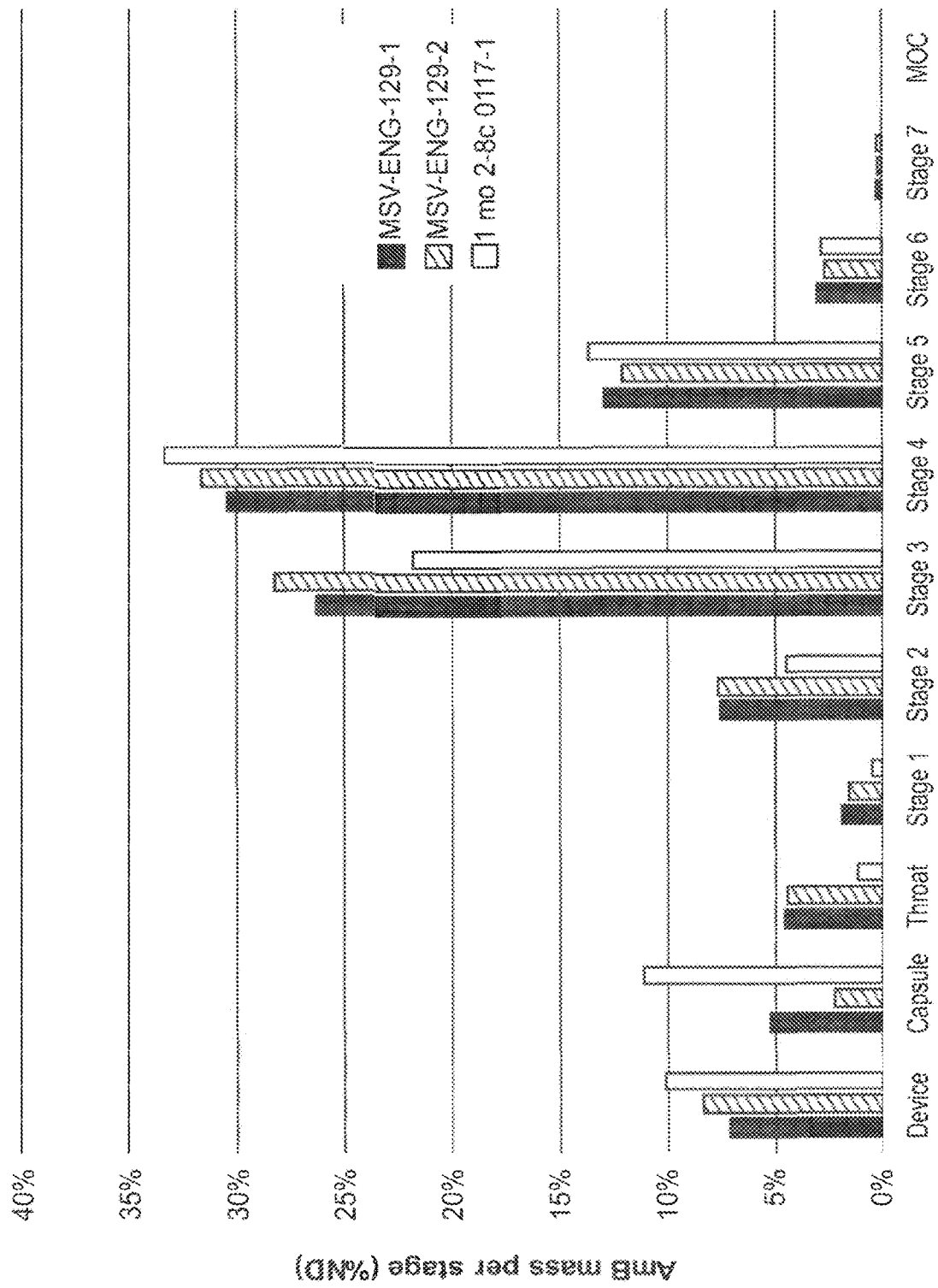
FIG. 15 displays the aerodynamic particle size distribution (APSD) of ABCI-003.

Example 21: Comparison of Solid State Properties of Development Batches of PLCI-002, ABCI-003 and ABCI-004 With GMP Batches for Early Clinical Development Comparable XRPD diffraction patterns (FIG. 13) and main transition temperatures, as determined by differential scanning calorimetry (FIG. 14) were observed for development batches used in GLP toxicology studies and GMP batches used for early clinical development. The results suggest that wet-milled amphotericin B crystals retain their crystallinity while being embedded within a shell comprising a mixture of phospholipids and cholesterol that have a main transition temperature (i.e., a gel to liquid crystal phase transition temperature) for the dehydrated powders in excess of 90° C.

Example 22: Aerosol Performance of GMP Batch of ABCI-003

Spray-dried ABCI-003 powders were filled with good precision (RSD <3%) and accuracy (2 mg dose) into size 3 HPMC capsules with a drum-filling process (Harro Höfliger).

Capsule retention, device retention and the delivered dose of AmB from the RS01 dry powder inhaler were determined at a pressure drop of 4 kPa with an inhaled volume of 4 L. The mean delivered dose was 83.1±2.4%, with capsule and device retention of 6.3±0.27% and 7.0±2.0%, respectively (N=5). Drug concentrations were quantitated with a RP-HPLC method.

The aerodynamic particle size distribution (APSD) of ABCI-003 was determined on a Next Generation Impactor operated under the same conditions as detailed above (FIG. 15). Batch MSV-ENG-129 represents a filling development run with the GMP spray-dried batch intended for use in Phase 1. Results for this batch are compared with a development lot following 1 month stability at refrigerated conditions.

Key features of the APSD include: less than 5% deposition in the USP throat and on Stage 1 in the impactor. The monomodal size distribution peaks on Stage 4 with significant deposition on Stages 3 and 5. The MMAD for the development batch is 2.5 μm, while the two runs with the clinical material yielded a MMAD of 2.8 μm. The fine particle dose less than 5 μm was 69.6% of the nominal dose for the development batch and 66.8% for the clinical batch. The fine particle dose on Stages 3 to filter, a surrogate for total lung dose, was 71.4% of the nominal dose for the development batch and 70.6% for the clinical batch. The development batch had greater deposition in the device and capsule. Overall, the clinical batch may be expected to achieve a total lung dose of 60-70% of the nominal dose, and upwards of 75-85% of the delivered dose.

INCORPORATION BY REFERENCE

All patents and published patent applications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

We claim:

1. A pharmaceutical composition, comprising:
(i) amphotericin B (AmB), or a pharmaceutically acceptable salt or hydrate thereof;
(ii) cholesterol (Chol);
(iii) phospholipids, comprising hydrogenated soy phosphatidylcholine (HSPC) and distearoylphosphatidylglycerol (DSPG); and
(iv) calcium chloride ($CaCl_2$);
wherein:
the AmB and Chol are not complexed; the AmB is not encapsulated in liposomes; and
the pharmaceutical composition is formulated as a dry powder.

2. The pharmaceutical composition of claim 1, wherein the amount of AmB is about 0.5% to about 25% w/w.

3. The pharmaceutical composition of claim 1, wherein the amount of Chol is about 0.1% to about 8% w/w.

4. The pharmaceutical composition of claim 1, wherein the amount of $CaCl_2$ is about 1% to about 10% w/w.

5. The pharmaceutical composition of claim 1, wherein the amount of phospholipids is about 60% to about 95% w/w.

6. The pharmaceutical composition of claim 1, wherein the weight ratio of Chol to phospholipids is about 0.001:1 to about 0.1:1.

7. The pharmaceutical composition of claim 1, wherein the weight ratio of soy phosphatidylcholine (HSPC) to distearoylphosphatidylglycerol (DSPG) is about 2:1 to about 19:1.

8. The pharmaceutical composition of claim 1, wherein the molar ratio of Chol to AmB is about 0.05:1 to about 1.2:1.

9. The pharmaceutical composition of claim 1, wherein the molar ratio of phospholipids to $CaCl_2$ is about 4:1 to about 2:1.

10. The pharmaceutical composition of claim 1, wherein the AmB has a crystallinity greater than about 75%.

11. The pharmaceutical composition of claim 1, comprising:
(i) about 14.0% w/w amphotericin B (AmB);
(ii) about 2.3% w/w cholesterol (Chol);
(iii-a) about 70.3% w/w hydrogenated soy phosphatidylcholine (HSPC);
(iii-b) about 7.8% w/w distearoylphosphatidylglycerol (DSPG); and
(iv) about 5.52% w/w calcium chloride ($CaCl_2$).

12. The pharmaceutical composition of claim 1, comprising:
(i) about 14.0% w/w amphotericin B (AmB);
(ii) about 6.81% w/w cholesterol (Chol);
(iii-a) about 51.2% w/w hydrogenated soy phosphatidylcholine (HSPC);
(iii-b) about 22.8% w/w distearoylphosphatidylglycerol (DSPG); and
(iv) about 5.2% w/w calcium chloride ($CaCl_2$).

13. The pharmaceutical composition of claim 1, comprising:
(i) about 3.4% w/w amphotericin B (AmB);
(ii) about 0.57% w/w cholesterol (Chol);
(iii-a) about 80.72% w/w hydrogenated soy phosphatidylcholine (HSPC);
(iii-b) about 8.97% w/w distearoylphosphatidylglycerol (DSPG); and
(iv) about 6.34% w/w calcium chloride ($CaCl_2$).

14. The pharmaceutical composition of claim 1, comprising:
(i) a Chol/AmB ratio of about 0.4 to 1.2 mol/mol;
(ii) a Chol/PL ratio of less than about 0.05 w/w;
(iii) a HSPC/DSPG ratio of about 2.3 to about 9.0 w/w; and
(iv) a PL/$Ca^{2+}$ratio of about 2:1 mol/mol.

15. The pharmaceutical composition of claim 1, wherein the AmB is coated with a porous shell of phospholipids and Chol.

16. The pharmaceutical composition of claim 1, wherein the mass median diameter, $X_{50}$, of the powder particles is about 1.0 to about 4.0 μm.

17. The pharmaceutical composition of claim 1, wherein the tapped density of the powder particles is about 0.03 to about 0.4 g/mL.

18. The pharmaceutical composition of claim 1, wherein the Carr's index of the powder particles is about 20 to about 32.

19. The pharmaceutical composition of claim 15, wherein the main transition temperature ($T_m$) of the shell is at least 80° C.

20. The pharmaceutical composition of claim 1, wherein the water content of the powder is about 1.5 to about 6% w/w.

21. The pharmaceutical composition of claim 1, wherein the composition is formulated for pulmonary administration or airway administration.

22. The pharmaceutical composition of claim 21, wherein the composition is formulated for aerosol administration.

23. The pharmaceutical composition of claim 22, wherein the mass median aerodynamic diameter of the powder particles is about 2.0 μm to about 3.5 μm.

24. A method of increasing the pH of airway surface liquid, comprising administering to a subject in need thereof an effective amount of the pharmaceutical composition of claim 1, thereby increasing the pH of airway surface liquid in the subject; wherein the administration is pulmonary.

25. A method of increasing bicarbonate secretion into airway surface liquid, comprising administering to a subject in need thereof an effective amount of the pharmaceutical composition of claim 1, thereby increasing bicarbonate secretion into airway surface liquid in the subject; wherein the administration is pulmonary.

26. A method of increasing expiratory volume in one second (FEV1), comprising administering to a subject in need thereof an effective amount of the pharmaceutical composition of claim 1, thereby increasing the subject's FEV1; wherein the administration is pulmonary.

* * * * *